US011466327B2

(12) United States Patent
Stefan et al.

(10) Patent No.: US 11,466,327 B2
(45) Date of Patent: Oct. 11, 2022

(54) USE OF THE EXPRESSION OF SPECIFIC GENES FOR THE PROGNOSIS OF PATIENTS WITH TRIPLE NEGATIVE BREAST CANCER

(71) Applicants: INSTITUT GUSTAVE ROUSSY, Villejuif (FR); ISTITUTO EUROPEO DI ONCOLOGIA (IEO), Milan (IT)

(72) Inventors: Michiels Stefan, Paris (FR); Mohamed Amine Bayar, Paris (FR); Fabrice Andre, Sceaux (FR); Carmen Criscitiello, Milan (IT); Giuseppe Curigliano, Milan (IT)

(73) Assignees: ISTITUTO EUROPEO DI ONCOLOGIA (IEO), Milan (IT); INSTITUT GUSTAVE ROUSSY, Villejuif (FR)

( * ) Notice: Subject to any disclaimer, the term of this patent is extended or adjusted under 35 U.S.C. 154(b) by 463 days.

(21) Appl. No.: 16/313,659

(22) PCT Filed: Jul. 3, 2017

(86) PCT No.: PCT/EP2017/066533
§ 371 (c)(1),
(2) Date: Dec. 27, 2018

(87) PCT Pub. No.: WO2018/002385
PCT Pub. Date: Jan. 4, 2018

(65) Prior Publication Data
US 2020/0071766 A1 Mar. 5, 2020

(30) Foreign Application Priority Data
Jul. 1, 2016 (EP) .................................. 16305838

(51) Int. Cl.
*C12Q 1/6886* (2018.01)
(52) U.S. Cl.
CPC ..... *C12Q 1/6886* (2013.01); *C12Q 2600/106* (2013.01); *C12Q 2600/118* (2013.01); *C12Q 2600/158* (2013.01)

(58) Field of Classification Search
CPC ............ C12Q 1/6886; C12Q 2600/118; C12Q 2600/158
See application file for complete search history.

(56) References Cited

FOREIGN PATENT DOCUMENTS

WO WO-2010/076322 A1 7/2010

OTHER PUBLICATIONS

International Report on Patentability for International Patent Application No. PCT/EP2017/066533 dated Jan. 1, 2019 (6 pages).

Chen et al., "The expression of CXCL13 and its relation to unfavorable clinical characteristics in young breast cancer," J Transl Med. 13:168 (2015) (13 pages).
Wang et al., "Common germline polymor-phisms in COMT, CYP19A1, ESR1, PGR, SULT1E1 and STS and survival after a diagnosis of breast cancer," Breast Diseases: A Year Book® Quarterly. 21(2):147-148 (2010).
Ring et al., "Generation of an algorithm based on minimal gene sets to clinically subtype triple negative breast cancer patients," BMC Cancer. 16:143 (2016) (8 pages).
Lehmann et al., "Refinement of Triple-Negative Breast Cancer Molecular Subtypes: Implications for Neoadjuvant Chemotherapy Selection," PLoS One. 11(6):e0157368 (2016) (22 pages).
Udler et al., "Common germline polymorphisms in COMT, CYP19A1, ESR1, PGR, SULT1E1 and STS and survival after a diagnosis of breast cancer," Int J Cancer. 125(11):2687-96 (2009).
Desmedt et al., "Multifactorial approach to predicting resistance to anthracyclines," J Clin Oncol. 29(12):1578-86 (2011).
Dieci et al., "Prognostic value of tumor-infiltrating lymphocytes on residual disease after primary chemotherapy for triple-negative breast cancer: a retrospective multicenter study," Ann Oncol. 25(3):611-8 (2014).
Dieci et al. "Prognostic and predictive value of tumor-infiltrating lymphocytes in two phase III randomized adjuvant breast cancer trials," Ann Oncol. 26(8):1698-704 (2015).
Hatzis et al., "A genomic predictor of response and survival following taxane-anthracycline chemotherapy for invasive breast cancer," JAMA. 305(18):1873-81 (2011).
Tibshirani, "The lasso method for variable selection in the Cox model," Stat Med. 16(4):385-95 (1997).
Shi et al., "The MicroArray Quality Control (MAQC)-II study of common practices for the development and validation of microarray-based predictive models," available in PMC Mar. 30, 2012, published in final edited form as: Nat Biotechnol. 28(8):827-38 (2010) (25 pages).
Benjamini et al. "Controlling the False Discovery Rate: A Practical and Powerful Approach to Multiple Testing," J R Statist Soc., Series B (Methodological). 57(1), 289-300 (1995).
Iwamoto et al., "Gene pathways associated with prognosis and chemotherapy sensitivity in molecular subtypes of breast cancer," J Natl Cancer Inst. 103(3):264-72 (2011).
Inaba et al., Fusion of the leucine zipper gene HLF to the E2A gene in human acute B-lineage leukemia. Science. 257(5069):531-4 (1992).
Tibshirani, "Regression Shrinkage and Selection via the Lasso," J R Statist Soc., Series B (Methodological). 58(1), 267-288 (1996).
Jabbour et al., "New insights into the pathophysiology and therapy of adult acute lymphoblastic leukemia," Cancer. 121(15):2517-28 (2015).
Waters et al., "Hepatic leukemia factor promotes resistance to cell death: implications for therapeutics and chronotherapy," Toxicol Appl Pharmacol. 268(2):141-8 (2013).

(Continued)

*Primary Examiner* — Teresa E Strzelecka
(74) *Attorney, Agent, or Firm* — Clark & Elbing LLP

(57) ABSTRACT

The present invention relates to the use of the value of the expression of at least one gene selected from the group comprising: GBP 1 gene, HLF gene, CXCL13 gene and SULT1E1 gene, for the estimation of prognosis of distant relapse-free survival or overall survival of a patient with triple negative breast cancer (TNBC) having received a neoadjuvant chemotherapy (NACT).

Figure 1A:
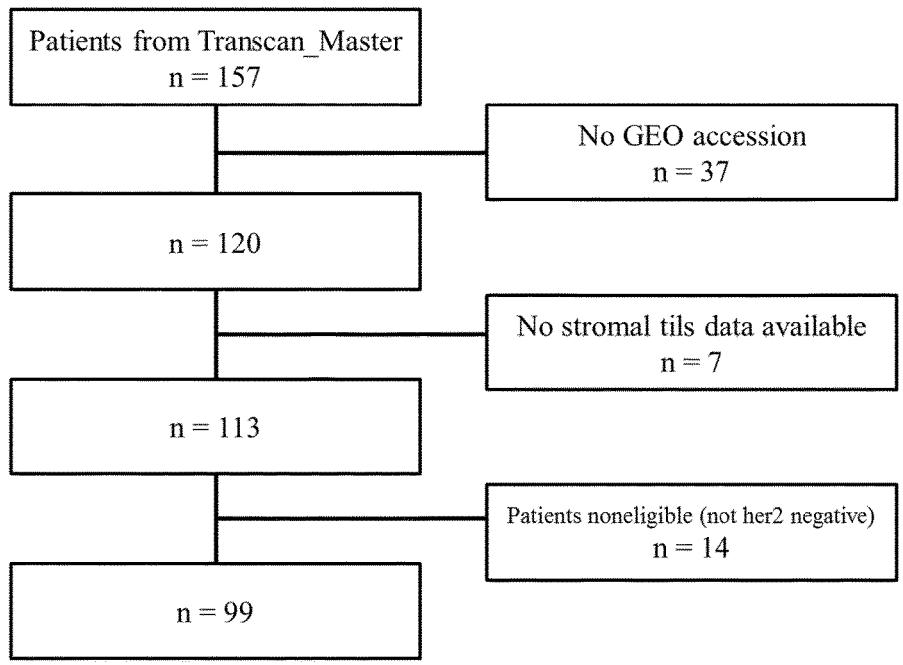

3 Claims, 36 Drawing Sheets
Specification includes a Sequence Listing.

(56) References Cited

OTHER PUBLICATIONS

Schernhammer et al., "Rotating night shifts and risk of breast cancer in women participating in the nurses' health study," J Natl Cancer Inst. 93(20):1563-8 (2001).

Lévi et al., "Chronotherapy of colorectal cancer metastases," Hepatogastroenterology. 48(38):320-2 (2001).

Gachon et al., "The circadian PAR-domain basic leucine zipper transcription factors DBP, TEF, and HLF modulate basal and inducible xenobiotic detoxification," Cell Metab. 4(1):25-36 (2006).

Kao et al., "Molecular profiling of breast cancer cell lines defines relevant tumor models and provides a resource for cancer gene discovery," PLoS One. 4(7):e6146 (2009) (16 pages).

Barrangou et al., "Advances in CRISPR-Cas9 genome engineering: lessons learned from RNA interference," Nucleic Acids Res. 43(7):3407-19 (2015).

Hsu et al., "Development and applications of CRISPR-Cas9 for genome engineering," Cell. 157(6):1262-78 (2014).

McCall et al., "Frozen robust multiarray analysis (fRMA)," Biostatistics. 11(2):242-53 (2010).

Komorowska et al., "Hepatic leukemia factor is essential for maintaining hematopoietic stem cell function," Experimental Hematology. 43(9):S73 (2015).

Figure 27

All trials (neoadj.complete.csv) N = 1001
- EORTC 10994    n = 160
- I-SPY-1    n = 83
- LBJ/INEN/GEICAM    n = 58
- MDACC Trial    n = 178
- TOP    n = 114
- MAQCII/MDACC    n = 265
- MAQCIII    n = 82
- USO-02103    n = 61

Available geo accession N = 963
- EORTC 10994    n = 160
- I-SPY-1    n = 83
- LBJ/INEN/GEICAM    n = 58
- MDACC Trial    n = 178
- TOP    n = 114
- MAQCII/MDACC    n = 227
- MAQCIII    n = 82
- USO-02103    n = 61

Publically available genomic data N = 865
- EORTC 10994    n = 160
- I-SPY-1    n = 83
- LBJ/INEN/GEICAM    n = 58
- MDACC Trial    n = 163
- TOP    n = 73
- MAQCII/MDACC    n = 186
- MAQCIII    n = 82
- USO-02103    n = 61

ER - , HER2- N = 373
- EORTC 10994    n = 92
- I-SPY-1    n = 36
- LBJ/INEN/GEICAM    n = 21
- MDACC Trial    n = 48
- TOP    n = 52
- MAQCII/MDACC    n = 55
- MAQCIII    n = 41
- USO-02103    n = 28

Available data drfs N = 185
- EORTC 10994    n = 0
- I-SPY-1    n = 36
- LBJ/INEN/GEICAM    n = 21
- MDACC Trial    n = 0
- TOP    n = 48
- MAQCII/MDACC    n = 55
- MAQCIII    n = 0
- USO-02103    n = 25

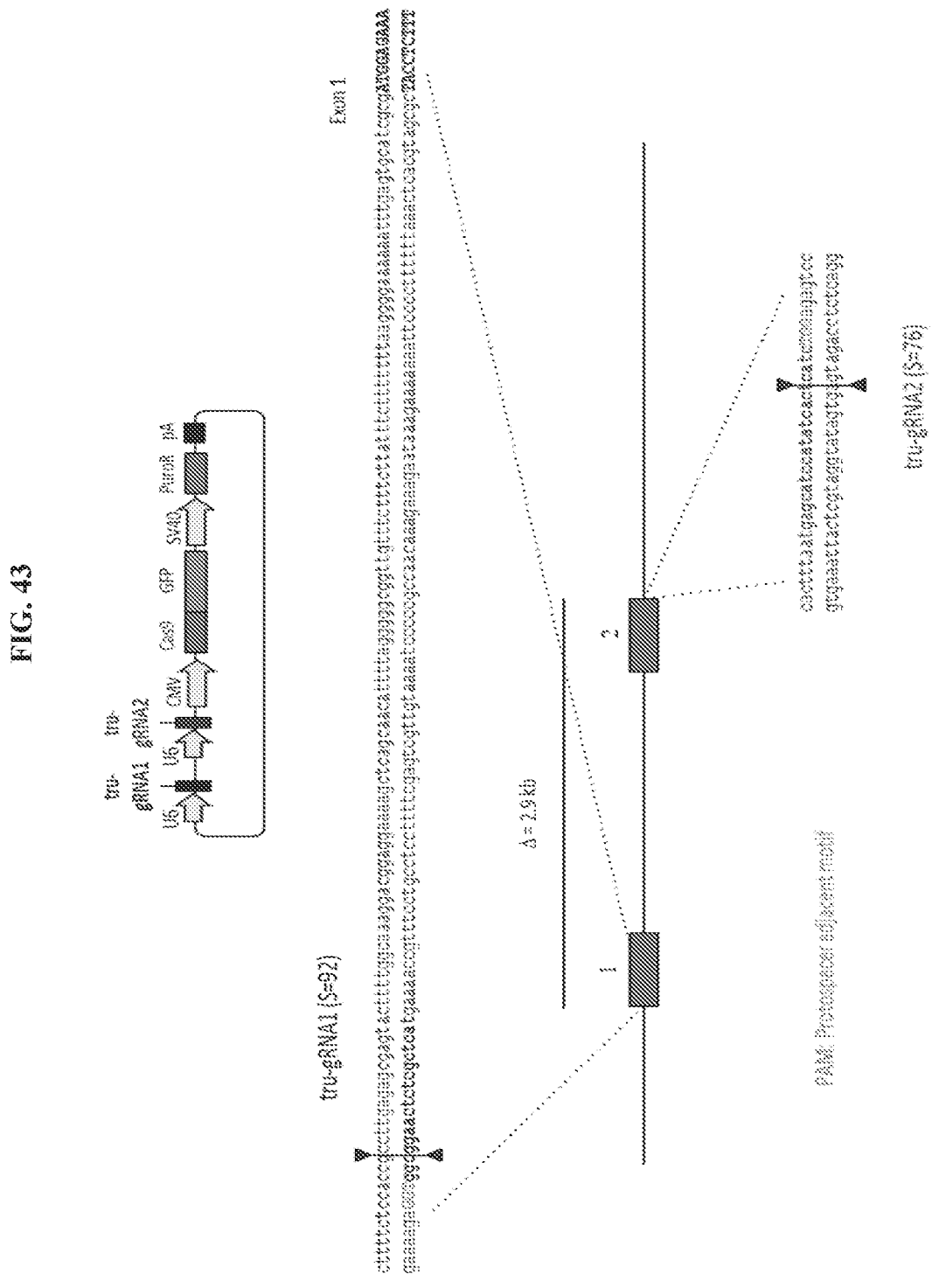

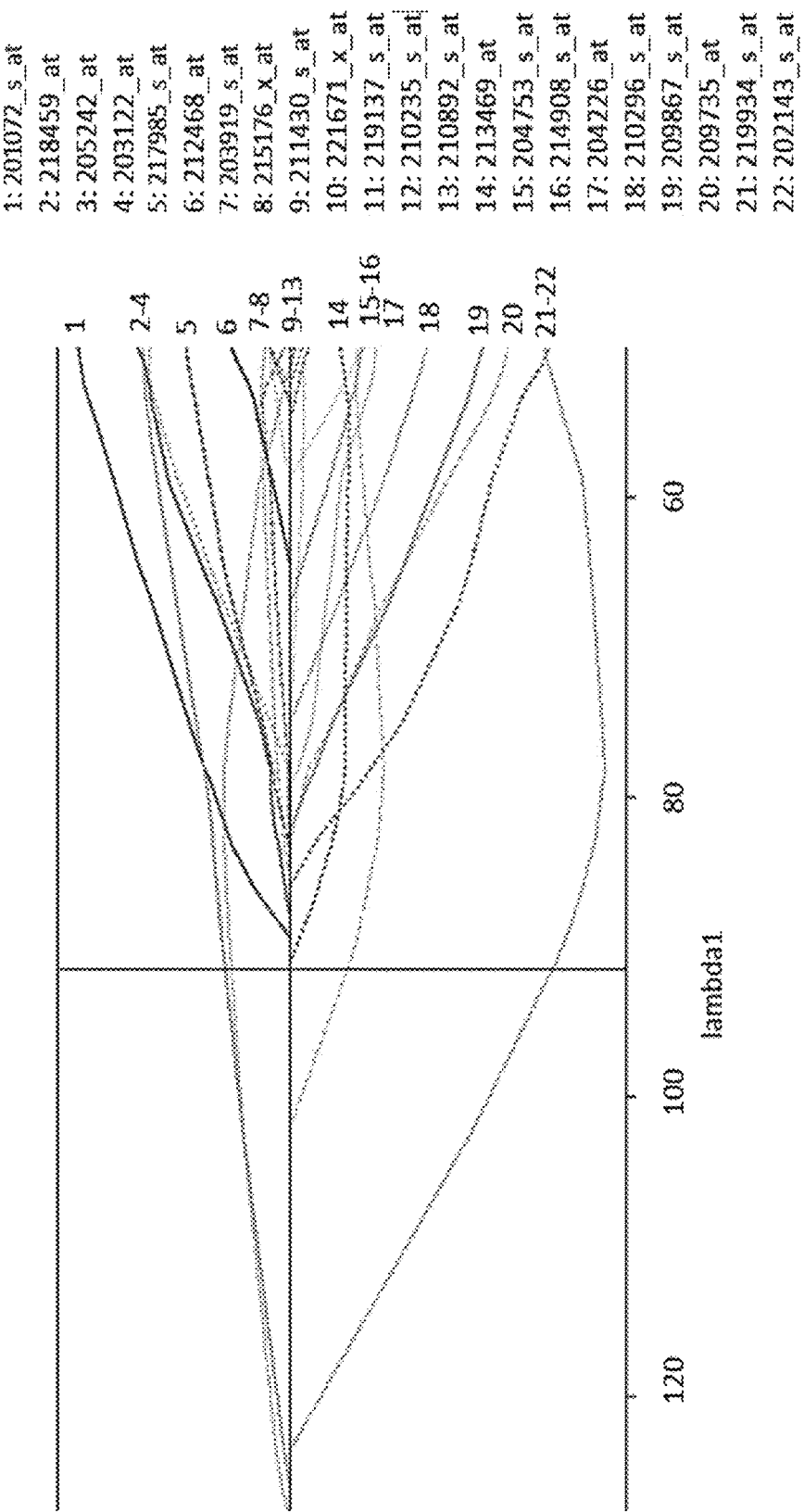

SEQUENCE LISTING

```
<160> NUMBER OF SEQ ID NOS: 6

<210> SEQ ID NO 1
<211> LENGTH: 3050
<212> TYPE: DNA
<213> ORGANISM: Homo sapiens

<400> SEQUENCE: 1
ggagtcagtg atttgaacga agtactttca gtttcatatt actctaaatc cattacaaat      60
ctgcttagct tctaaatatt tcatcaatga ggaaatccca gccctacaac ttcggaacag     120
tgaaatatta gtccagggat ccagtgagag acacagaagt gctagaagcc agtgctcgtg     180
aactaaggag aaaaagaaca gacaagggaa cagcctggac atggcatcag agatccacat     240
gacaggccca atgtgcctca ttgagaacac taatgggcga ctgatggcga atccagaagc     300
tctgaagatc ctttctgcca ttacacagcc tatggtggtg gtgcaattg tgggcctcta      360 ccgcacaggc aaatcctacc tgatgaacaa gctggctgga aagaaaaagg gcttctctct     420
gggctccacg gtgcagtctc acactaaagg aatctggatg tggtgtgtgc cccaccccaa     480
gaagccaggc cacatcctag ttctgctgga caccgagggt ctgggagatg tagagaaggg     540
tgacaaccag aatgactcct ggatcttcgc cctggccgtc ctcctgagca gcaccttcgt     600
gtacaatagc ataggaacca tcaaccagca ggctatggac caactgtact atgtgacaga     660
gctgacacat agaatccgat caaaatcctc acctgatgag aatgagaatg aggttgagga     720
ttcagctgac tttgtgagct tcttcccaga ctttgtgtgg acactgagag atttctccct     780
ggacttggaa gcagatggac aaccccctcac accagatgag tacctgacat actccctgaa     840
gctgaagaaa ggtaccagtc aaaaagatga aacttttaac ctgcccagac tctgtatccg     900
gaaattcttc ccaaagaaaa aatgctttgt ctttgatcgg cccgttcacc gcaggaagct     960
tgcccagctc gagaaactac aagatgaaga gctggacccc gaatttgtgc aacaagtagc    1020
agacttctgt tcctacatct ttagtaattc caaaactaaa actctttcag gaggcatcca    1080
ggtcaacggg cctcgtctag agagcctggt gctgacctac gtcaatgcca tcagcagtgg    1140
ggatctgccg tgcatggaga acgcagtcct ggccttggcc cagatagaga actcagctgc    1200
agtgcaaaag gctattgccc actatgaaca gcagatgggc cagaaggtgc agctgcccac    1260
agaaaccctc caggagctgc tggacctgca cagggacagt gagagagagg ccattgaagt    1320
cttcatcagg agttccttca aagatgtgga ccatctattt caaaaggagt tagcggccca    1380
gctagaaaaa aagcgggatg acttttgtaa acagaatcag gaagcatcat cagatcgttg    1440
ctcagcttta cttcaggtca ttttcagtcc tctagaagaa gaagtgaagg cgggaattta    1500
ttcgaaacca ggggctatc gtctctttgt tcagaagcta caagacctga agaaaaagta    1560
ctatgaggaa ccgaggaagg ggatacaggc tgaagagatt ctgcagacat acttgaaatc    1620
caaggagtct atgactgatg caattctcca gacagaccag actctcacag aaaaagaaaa    1680
```

```
ggagattgaa gtggaacgtg tgaaagctga gtctgcacag gcttcagcaa aaatgttgca    1740
ggaaatgcaa agaaagaatg agcagatgat ggaacagaag gagaggagtt atcaggaaca    1800
cttgaaacaa ctgactgaga agatggagaa cgacagggtc cagttgctga agagcaaga     1860 gaggaccctc gctcttaaac ttcaggaaca ggagcaacta ctaaaagagg gatttcaaaa    1920
agaaagcaga ataatgaaaa atgagataca ggatctccag acgaaaatga gacgacgaaa    1980
ggcatgtacc ataagctaaa gaccagagcc ttcctgtcac ccctaaccaa ggcataattg    2040
aaacaatttt agaatttgga acaagcgtca ctacatttga taataattag atcttgcatc    2100
ataacaccaa agtttataa aggcatgtgg tacaatgatc aaaatcatgt tttttcttaa     2160
aaaaaaaaaa agactgtaaa ttgtgcaaca aagatgcatt tacctctgta tcaactcagg    2220
aaatctcata agctggtacc actcaggaga agtttattct tccagatgac cagcagtaga    2280
caaatggata ctgagcagag tcttaggtaa aagtcttggg aaatatttgg gcattggtct    2340
ggccaagtct acaatgtccc aatatcaagg acaaccaccc tagcttctta gtgaagacaa    2400
tgtacagtta tccgttagat caagactaca cggtctatga gcaataatgt gatttctgga    2460
cattgcccat gtataatcct cactgatgat ttcaagctaa agcaaaccac cttatacaga    2520
gatctagaat ctctttatgt tctccagagg aaggtggaag aaaccatggg caggagtagg    2580
aattgagtga taaacaattg ggctaatgaa gaaaacttct cttattgttc agttcatcca    2640
gattataact tcaatgggac actttagacc attagacaat tgacactgga ttaaacaaat    2700
tcacataatg ccaaatacac aatgtattta tagcaacgta taatttgcaa agatggactt    2760
taaaagatgc tgtgtaacta aactgaaata attcaattac ttattattta gaatgttaaa    2820
gcttatgata gtcttttcta actcttaaca ctcatacttg aaaactttct gagtttcccc    2880
agaagagaat atgggatttt ttttgacatt tttgactcat ttaataatgc tcttgtgttt    2940
acctagtata tgtagacttt gtcttatgtg tgaaaagtcc taggaaagtg gttgatgttt    3000
cttatagcaa ttaaaaatta tttttgaact gaaaatacaa tgtatttcac                3050

<210> SEQ ID NO 2
<211> LENGTH: 5607
<212> TYPE: DNA
<213> ORGANISM: Homo sapiens

<400> SEQUENCE: 2
actcttgtca gggccgcggc acatgggcgg ccggatgcgc tgagcccggc gctgcggggc      60
cgcggagcgc tggggagcag cggccgccgg cgcggggagg ggggtggggt gggacggcgc     120
accgcctccg gtgctggcac tagggctgg ggtcggcgcg gtgtcttctg cccttctgca      180
gccgtcgaca ttttttttc tttctttttt tcaattttga acattttgca aaacgagggg      240
ttcgaggcag gtgagagcat cctgcacgtc gccggggagc ccgcgggcac ttggcgcgct     300
ctcctgggac cgtctgcact ggaaacccga agtttttttt taatatata ttttatgca       360 gatgtattta taaagatata agtaatttt ttcttccctt ttctccaccg ccttgagagc      420
gagtactttt ggcaaaggac ggaggaaaag ctcagcaaca ttttagggg cggttgtttc      480 tttcttattt ctttttttaa ggggaaaaaa tttgagtgca tcgcgatgga gaaaatgtcc     540
cgaccgctcc ccctgaatcc caccttatc ccgcctccct acggcgtgct caggtccctg      600
ctggagaacc cgctgaagct cccccttcac cacgaagacg catttagtaa agataaagac      660
aaggaaaaga agctgatga tgagagtaac agcccgacgg tccccagtc ggcattcctg       720 gggcctacct tatgggacaa aaccccttccc tatgacggag atactttcca gttggaatac    780
```

```
atggacctgg aggagttttt gtcagaaaat ggcattcccc ccagcccatc tcagcatgac    840
cacagccctc accctcctgg gctgcagcca gcttcctcgg ctgcccctc  ggtcatggac    900 ctcagcagcc gggcctctgc accccttcac cctggcatcc catctccgaa ctgtatgcag    960
agccccatca gaccaggtca gctgttgcca gcaaaccgca atacaccaag tcccattgat   1020
cctgacacca tccaggtccc agtgggttat gagccagacc cagcagatct tgccctttcc   1080
agcatccctg gccaggaaat gtttgaccct cgcaaacgca agttctctga ggaagaactg   1140
aagccacagc ccatgatcaa gaaagctcgc aaagtcttca tccctgatga cctgaaggat   1200
gacaagtact gggcaaggcg cagaaagaac aacatggcag ccaagcgctc ccgcgacgcc   1260
cggaggctga agagaaccag gatcgccatc cgggcctcgt tcctggagaa ggagaactcg   1320
gccctccgcc aggaggtggc tgacttgagg aaggagctgg gcaaatgcaa gaacatactt   1380
gccaagtatg aggccaggca cgggcccctg taggatggca ttttgcagg ctggctttgg    1440 aatagatgga cagtttgttt cctgtctgat agcaccacac gcaaaccaac ctttctgaca   1500
tcagcacttt accagaggca taaacacaac tgactcccat tttggtgtgc atctgtgtgt   1560
gtgtgcgtgt atatgtgctt gtgctcatgt gtgtggtcag cggtatgtgc gtgtgcgtgt   1620
tcctttgctc ttgccatttt aaggtagccc tctcatcgtc ttttagttcc aacaaagaaa   1680
ggtgccatgt ctttactaga ctgaggagcc ctctcgcggg tctcccatcc cctccctcct   1740
tcactcctgc ctcctcagct ttgcttcatg ttcgagctta cctactcttc caggactctc   1800
tgcttggatt cactaaaaag ggccctggta aaatagtgga tctcagtttt taagagtaca   1860
agctcttgtt tctgtttagt ccgtaagtta ccatgctaat gaggtgcaca caataactta   1920
gcactactcc gcagctctag tcctttataa gttgctttcc tcttactttc agttttggtg   1980
ataatcgtct tcaaattaaa gtgctgttta gatttattag atcccatatt tacttactgc   2040
tatctactaa gtttcctttt aattctacca accccagata agtaagagta ctattaatag   2100
aacacagagt gtgttttttgc actgtctgta cctaaagcaa taatcctatt gtacgctaga   2160
gcatgctgcc tgagtattac tagtggacgt aggatatttt ccctacctaa gaatttcact   2220
gtcttttaaa aaacaaaaag taaagtaatg catttgagca tggccagact attccctagg   2280
acaaggaagc agagggaaat gggaggtcta aggatgaggg gttaatttat cagtacatga   2340
gccaaaaact gcgtcttgga ttagcctttg acattgatgt gttcggtttt gttgttcccc   2400
ttccctcaca ccctgcctcg ccccacttt  tctagttaac ttttttccata tccctcttga   2460 cattcaaaac agttacttaa gattcagttt tcccacttt  tggtaatata tatatttttg    2520
tgaattatac tttgttgttt ttaaaagaa  aatcagttga ttaagttaat aagttgatgt    2580
tttctaaggc ccttttttcct agtggtgtca ttttgaatg  cctcataaat taatgattct    2640
gaagcttatg tttcttattc tctgtttgct tttgaacgta tgtgctctta taaagtggac   2700
ttctgaaaaa tgaatgtaaa agacactggt gtatctcaga aggggatggt gttgtcacaa   2760
actgtggtta atccaatcaa tttaaatgtt tactatagac caaaggaga  gattattaaa    2820 tcgtttaatg tttatacaga gtaattatag gaagttcttt tttgtacagt attttttcaga   2880 tataaatact gacaatgtat tttggaagac atatattata tatagaaaag aggagaggaa   2940
aactattcca tgttttaaaa ttatatagca aagatatata ttcaccaatg ttgtacagag   3000
aagaagtgct tggggggtttt tgaagtctttt aatattttaa gccctatcac tgacacatca   3060
gcatgttttc tgctttaaat taaaatttta tgacagtatc gaggcttgtg atgacgaatc   3120
```

-continued

```
ctgctctaaa atacacaagg agctttcttg tttcttatta ggcctcagaa agaagtcagt      3180
taacgtcacc caaaagcaca aaatggattt tagtcaaata tttattggat gatacagtgt      3240
tttttaggaa aagcatctgc cacaaaaatg ttcacttcga aattctgagt tcctggaatg      3300
gcacgttgct gccagtgccc cagacagttc ttttctaccc tgcgggcccg cacgttttat      3360
gaggttgata tcggtgctat gtgtttggtt tataatttga tagatgtttg actttaaaga      3420
tgattgttct tttgtttcat taagttgtaa aatgtcaaga aattctgctg ttacgacaaa      3480
gaaacatttt acgctagatt aaaatatcct ttcatcaatg ggattttcta gtttcctgcc      3540
ttcagagtat ctaatccttt aatgatctgg tggtctcctc gtcaatccat cagcaatgct      3600
tctctcatag tgtcatagac ttgggaaacc caaccagtag gatatttcta caaggtgttc      3660
attttgtcac aagctgtaga taacagcaag agatgggggt gtattggaat tgcaatacat      3720
tgttcaggtg aataataaaa tcaaaaactt ttgcaatctt aagcagagat aaataaaaga      3780
tagcaatatg agacacaggt ggacgtagag ttggcctttt tacaggcaaa gaggcgaatt      3840
gtagaattgt tagatggcaa tagtcattaa aaacatagaa aaatgatgtc tttaagtgga      3900
gaattgtgga aggattgtaa catggaccat ccaaatttat ggccgtatca aatggtagct      3960
gaaaaaacta tatttgagca ctggtctctc ttggaattag atgtttatat caaatgagca      4020
tctcaaatgt tttctgcaga aaaaaataaa aagattctaa taaatgtat tctcttgtgt       4080
gccaggagag gtttcagaaa cctacctcgt cttacaaatt taaacacttt ggagtctgta      4140
caggtgcctt atatgtaggt cattgtcacg atacacacac acgaacactc cctctggact      4200
ggctgcctct ccatccaggg cagttaacta gcaaacaagg cagatctgct tcatggagcg      4260
ggaggccatg gcttgactct gagtgatttg ggtcaaccgg agtcagacgc atgtctgcac      4320
gctgcagcta ttatgagagt ccctttgtca tttttcacct tttcatccta agcatctttc      4380
agagattaat tatttggcca ttaacaatga atccaaatca tatcatactg acatcatcta      4440
gacatgattt ggaaggaaca gcttaggacc tcctgatgag gtcacattgt tgtttctttt      4500
aactagactt ggcaaagaaa ggcaaaaatt gaccagccta tctttctgct ggtgctgcct      4560
taaggaggta gtttgttgag gggagggctg tagatcatta cttcttttctc ttcaggaagt      4620
ggccactttg aaccattcaa ataccacatt aggcaagact gtgataggcc ttttgtcttc      4680
aaatacaaca ggcctccact gacccatccc tcaaagcaga aggaccctt gaggagagta       4740
cagatgggat tccacagtgg ggtgggtgga atggaaacct gtactagacc acccagaggt      4800
tccttctaac ccactggttt ggtggggaac tcacagtaat tccaaatgta caatcagatg      4860
tctagggtct gttttcggaa gaagcaagaa ttatcagtgg caccctcccc actgccccca      4920
gtgtaaaaca atagacattc tgtgaaatgc aaagctattc tttggttttt ctagtagttt      4980
atctcatttt accctattct tcctttaagg aaaactcaat cttatcaca gtcaattaga       5040
gcgatcccaa ggcatgggac caggcctgct tgcctatgtg tgatggcaat tggagatctg      5100
gatttagcac tggggtctca gcaccctgca ggtgtctgag actaagtgat ctgccctcca      5160
ggtggcgatc accttctgct cctaggtacc cccactggca aggccaaggt ctcctccacg      5220
tttttttctgc aattaataat gtcatttaaa aaatgagcaa agccttatcc gaatcggata     5280
tagcaactaa agtcaataca ttttgcagga ggctaagtgt aagagtgtgt gtgtgtgtgt      5340
gtgcgtgcat gtgtgtgtgt gtgtatgtgt gtgaataagt cgacataaag tctttaatttt    5400
tgagcacctt accaaacata acaataatcc attatccttt tggcaacacc acaaagatcg      5460
catctgttaa acaggtacaa gttgacatga ggttagttta attgtacacc atgatattgg      5520
```

| | | |
|---|---|---|
| tggtatttat gctgttaagt ccaaacctttt atctgtctgt tattcttaat gttgaataaa | 5580 | |
| ctttgaattt tttcctttca aaaaaaa | 5607 | |

<210> SEQ ID NO 3
<211> LENGTH: 1219
<212> TYPE: DNA
<213> ORGANISM: Homo sapiens

<400> SEQUENCE: 3

| | |
|---|---|
| gagaagatgt ttgaaaaaac tgactctgct aatgagcctg gactcagagc tcaagtctga | 60 |
| actctacctc cagacagaat gaagttcatc tcgacatctc tgcttctcat gctgctggtc | 120 |
| agcagcctct ctccagtcca aggtgttctg gaggtctatt acacaagctt gaggtgtaga | 180 |
| tgtgtccaag agagctcagt ctttatccct agacgcttca ttgatcgaat tcaaatcttg | 240 |
| ccccgtggga atggttgtcc aagaaaagaa atcatagtct ggaagaagaa caagtcaatt | 300 |
| gtgtgtgtgg accctcaagc tgaatggata caaagaatga tggaagtatt gagaaaaaga | 360 |
| agttcttcaa ctctaccagt tccagtgttt aagagaaaga ttccctgatg ctgatatttc | 420 |
| cactaagaac acctgcattc ttcccttatc cctgctctgg attttagttt tgtgcttagt | 480 |
| taaatctttt ccaggaaaaa gaacttcccc atacaaataa gcatgagact atgtaaaaat | 540 |
| aaccttgcag aagctgatgg ggcaaactca agcttcttca ctcacagcac cctatataca | 600 |
| cttggagttt gcattcttat tcatcaggga ggaaagtttc tttgaaaata gttattcagt | 660 |
| tataagtaat acaggattat tttgattata tacttgttgt ttaatgttta aaatttctta | 720 |
| gaaaacaatg gaatgagaat ttaagcctca aatttgaaca tgtggcttga attaagaaga | 780 |
| aaattatggc atatattaaa agcaggcttc tatgaaagac tcaaaaagct gcctgggagg | 840 |
| cagatggaac ttgagcctgt caagaggcaa aggaatccat gtagtagata tcctctgctt | 900 |
| aaaaactcac tacggaggag aattaagtcc tacttttaaa gaatttcttt ataaaattta | 960 |
| ctgtctaaga ttaatagcat tcgaagatcc ccagacttca tagaatactc agggaaagca | 1020 |
| tttaaagggt gatgtacaca tgtatccttt cacacatttg ccttgacaaa cttctttcac | 1080 |
| tcacatcttt ttcactgact ttttttgtgg ggggcggggc cggggggact ctggtatcta | 1140 |
| attctttaat gattcctata aatctaatga cattcaataa agttgagcaa acattttact | 1200 |
| taaaaaaaaa aaaaaaaa | 1219 |

<210> SEQ ID NO 4
<211> LENGTH: 1805
<212> TYPE: DNA
<213> ORGANISM: Homo sapiens

<400> SEQUENCE: 4

| | |
|---|---|
| caaatgcaga agtggttctc atctttttt gcagcttaag atctgccttg gtatttgaag | 60 |
| agatataaac tagatcaatt tctttcacag gatcaactaa acagtgtacc acaatgaatt | 120 |
| ctgaacttga ctattatgaa aagtttgaag aagtccatgg gattctaatg tataaagatt | 180 |
| ttgtcaaata ttgggataat gtggaagcgt tccaggcaag accagatgat cttgtcattg | 240 |
| ccacctaccc taaatctggt acaacctggg ttagtgaaat tgtgtatatg atctataaag | 300 |
| agggtgatgt ggaaaagtgc aaagaagatg taatttttaa tcgaataccc ttcctggaat | 360 |
| gcagaaaaga aaacctcatg aatggagtaa acaattaga tgagatgaat tctcctagaa | 420 |
| ttgtgaagac tcatttgcca cctgaacttc ttcctgcctc attttgggaa aaggattgta | 480 |

```
agataatcta tctttgccgg aatgcaaagg atgtggctgt ttccttttat tatttctttc      540
taatggtggc tggtcatcca aatcctggat cctttccaga gtttgtggag aaattcatgc      600
aaggacaggt tccttatggt tcctggtata aacatgtaaa atcttggtgg gaaaagggaa      660
agagtccacg tgtactattt cttttctacg aagacctgaa agaggatatc agaaaagagg      720
tgataaaatt gatacatttc ctggaaagga agccatcaga ggagcttgtg gacaggatta      780
tacatcatac ttcgttccaa gagatgaaga acaatccatc cacaaattac acaacactgc      840
cagacgaaat tatgaaccag aaattgtcgc ccttcatgag aaagggaatt acaggagact      900
ggaaaaatca ctttacagta gccctgaatg aaaaatttga taaacattat gagcagcaaa      960
tgaaggaatc tacactgaag tttcgaactg agatctaaga aggtctttct ttacttaaca     1020
tatctgatat taaagatttc ttttcattat tctccacttt ttcttatttt agattgctag     1080
aaaagacata atcatggatt atgttgacat tttcttttta aattttgtt taactttttt     1140 tttttttttt tgagacagag tctcactctg ttgcctaggc tggaggacag tggcacaatc     1200
atggctgatt gcagccttga cctccttgac tcaattgatc ctcccatctc agcctcccaa     1260
gtagctagga ctacagacat gtgcaaccat gtttggctaa ttttttttaat gtttttttgt     1320 agagatgagg tcttattata ttgtccaggc tggtcttgaa ttcctgggct caagcttccc     1380
aagtagctgc aacaacaggc acacaccacc atgctcaact aattttattt ctatttttg     1440 tatagacagg ggcttgctat agtgtccagg ctggtctgaa acccttgagc tcaagtgatc     1500
ttcccacacc agcctcccaa aatactggga ttacaggctt gagcctccat gcctggccca     1560
ggtaacatgt ttattgagct gtacatgcat atgagaaata agaaactttt ttttcctact     1620
atcatctctt aaattttgtt ttcttttct tttgcttcct cttcttcttt tctattttt     1680 ataaatatca tgcacaacta taacctatgg gaatgatgta gtaacacaga ttattcatct     1740
tgttagagtt gtattaaaaa taaacaagca tttcaaatta aaaaaaaaaa aaaaaaaaa     1800 aaaaa                                                                1805

<210> SEQ ID NO 5
<211> LENGTH: 137
<212> TYPE: DNA
<213> ORGANISM: Homo sapiens

<400> SEQUENCE: 5
cttttctcca ccgccttgag agcgagtact tttggcaaag gacggaggaa aagctcagca       60
acattttagg gggcggttgt ttctttctta tttcttttt taagggggaaa aaatttgagt      120 gcatcgcgat ggagaaa                                                     137

<210> SEQ ID NO 6
<211> LENGTH: 39
<212> TYPE: DNA
<213> ORGANISM: Homo sapiens

<400> SEQUENCE: 6
cactttaatg agcatccata tcactcatct ggagagtcc                              39
```

USE OF THE EXPRESSION OF SPECIFIC GENES FOR THE PROGNOSIS OF PATIENTS WITH TRIPLE NEGATIVE BREAST CANCER

SEQUENCE LISTING

The instant application contains a Sequence Listing which has been submitted in ASCII format via EFS-Web and is hereby incorporated by reference in its entirety. Said ASCII copy, created on Apr. 1, 2018, is named "50376_009001_Sequence Listing.txt" and is 16,463 bytes in size.

Recent advances in medical treatments have dramatically improved the outcome of triple negative breast cancers. As illustration, after a median follow-up of 36 months, only 12% of the patients included in the adjuvant bevacizumab-containing therapy in triple-negative breast cancer (BEATRICE) trial had presented a metastatic relapse. This data emphasizes the need to develop predictors of outcome in a patient with triple negative breast cancer (TNBC) who have received optimal adjuvant therapy, in order to identify those who are eligible to adjuvant trials, and need new investigational drugs.

It has been previously shown that the presence of tumor infiltration by lymphocytes after neoadjuvant chemotherapy is associated with an excellent outcome. In this study that included 304 patients, the presence of TILs>60% after neoadjuvant chemotherapy was observed in 10% of the patients and was associated with a 91% overall survival rate at 5 years. Interestingly, 85% of the samples with post-chemotherapy TIL+ were TIL− at baseline before chemotherapy (Dieci M V, Criscitiello C, Goubar A, et al. (2014) Prognostic value of tumorinfiltrating lymphocytes on residual disease after primary chemotherapy for triplenegative breast cancer: a retrospective multicenter study. Ann Oncol Off J Eur Soc Med Oncol ESMO 25:611-618. doi: 10.1093/annonc/mdt556).

1. Purpose

The Study Purpose is to Develop a Genomic Predictor of TIL after Chemotherapy and to Test its Prognostic Value in TNBC.

The strategy consists in developing a genomic predictor of TIL after neoadjuvant chemotherapy using only information obtained before the start of the neoadjuvant treatment (biopsies), and then to test whether this predictor could identify a subset of TNBC patients who do not have a systemic relapse.

One of the Aims is to Develop a Genomic Predictor of TIL after Neoadjuvant Chemotherapy in TNBC Using Only Information Before the Start of Chemotherapy.

In order to address this question, we will quantify post-chemotherapy TIL in series of TNBC treated with neoadjuvant chemotherapy and for which a genomic profile has already been generated. TIL will be assessed in post-chemotherapy samples from MDACC neoadjuvant series and TOP (Trial of Principle) trial.

The histopathologic evaluation of the percentage of intratumoral (It) and stromal (Str) TILs will be performed on Hematoxilyn and eosin-stained (HES) slides from surgical specimens and will be done according to criteria previously described and published by Denkert and colleagues. For each case, all the slides containing residual invasive breast disease will be evaluated.

The goal will be to collect information on post-chemotherapy TIL in a large series patients with TNBC treated with neoadjuvant chemotherapy that did not achieved pCR after surgery. There is a lot of discussion on the most appropriate cut-off and in the absence of a reliable gold standard; we modeled the continuous level of stromal TILS in the post chemotherapy sample as a function of gene expression. This model is more powerful than logistic models and will allow us to predict which patients would have stromal TILS superior to currently discussed cutoffs (40%, 50% or 60%). A RT-PCR based assay will then be developed on FFPE samples matched to their frozen counterparts.

The predictive value of the RT-PCR based assay for TIL-infiltration will be then validated on FFPE samples from IEO and GBG neoadjuvant studies.

Another Aim is to Validate the Prognostic Value of the Genomic Predictor in TNBC Treated with Neoadjuvant Chemotherapy Once the genomic predictor has been generated, we will test its prognostic value in patients with TNBC treated with adjuvant chemotherapy. Several series of samples will be used. First, the ACIS validation dataset will be used where both outcome and gene expression arrays are available. Second, we will perform gene expression profilings in the IBCSG study 22 and PACS08 in order to test the prognostic value of TIL-predictor in >300 TNBC treated with adjuvant therapy.

The Primary Analysis was Performed on TNBC Patients (ER-/HER2-). Description of all the Studies Included in the Present Analysis is Shown in Table 31.

Tumors were identified as ER-/HER2—based on ER assessment by IHC and HER2 assessment by IHC and fluorescent in situ hybridization, as originally reported. When unavailable, ER and HER2 status was assigned according to ESR1 and ERBB2 gene expression.

2. Invention

The present invention relates to the use of the value of the expression of at least one gene selected from the group comprising: GBP1 gene, HLF gene, CXCL13 gene and SULT1E1 gene, for the estimation of prognosis of distant relapse-free survival or overall survival of a patient with triple negative breast cancer (TNBC) having received a neoadjuvant chemotherapy (NACT).

In a particular embodiment, the present invention relates to said use of the value of the expression of the four genes: GBP1 gene, HLF gene, CXCL13 gene and SULT1E1 gene, for the estimation of prognosis of distant relapse-free survival or overall survival of a patient with triple negative breast cancer (TNBC) having received a neoadjuvant chemotherapy (NACT).

In a particular embodiment, the present invention relates to said use of the value of the expression of the four genes: GBP1 gene, HLF gene, CXCL13 gene and SULT1E1 gene, wherein a low value of the expression of the genes SULT1E1 and HLF, and a high value of the expression of the genes GBP1 and CXCL13, measured in a biopsy taken from a patient tumor before neoadjuvant chemotherapy corresponds to an high stromal tumor-infiltrating lymphocytes (Str-TIL) after neoadjuvant chemotherapy, corresponding to a good distant relapse free-survival or overall survival of said patient.

In a particular embodiment, the present invention relates to said use of the value of the expression of the four genes: GBP1 gene, HLF gene, CXCL13 gene and SULT1E1 gene, wherein a high value of the expression of the genes SULT1E1 and HLF, and a low value of the expression of the genes GBP1 and CXCL13, measured in a biopsy taken from a patient tumor before neoadjuvant chemotherapy corresponds to an low stromal tumor-infiltrating lymphocytes (Str-TIL) after neoadjuvant chemotherapy, corresponding to a short distant relapse free-survival or overall survival of said patient.

In a particular embodiment, the present invention relates to said use of the value of the expression of the four genes: GBP1 gene, HLF gene, CXCL13 gene and SULT1E1 gene for determining a genomic predictor of formula:

Genomic predictor=0.288*GBP1 expression+ 0.392*CXCL13 expression−1.027*HLF expression−1.726*SULT1E1 expression, and wherein the expression of the four genes corresponds respectively to the value of the mRNA of each one, for the estimation of prognosis of distant relapse-free survival or overall survival of a patient with triple negative breast cancer (TNBC) having received a neoadjuvant chemotherapy (NACT).

In a particular embodiment, the present invention relates to said use of the value of the expression of the four genes: GBP1 gene, HLF gene, CXCL13 gene and SULT1E1 gene wherein when the genomic predictor for a patient is more than or equal to 0.51, the patient has a good prognosis corresponding to a good distant relapse free-survival or overall survival of said patient.

In a particular embodiment, the present invention relates to sais use of the value of the expression of the four genes: GBP1 gene, HLF gene, CXCL13 gene and SULT1E1 gene wherein when the genomic predictor for a patient is strictly less than 0.51, the patient has a poor prognosis corresponding to a short distant relapse free-survival or overall survival of said patient.

The present invention also relates to an in vitro prognostic method of the distant relapse-free survival or overall survival in a patient with triple negative breast cancer (TNBC) having received a neoadjuvant chemotherapy (NACT) comprising the determination of the value of the expression of at least one gene selected from the group comprising: GBP1 gene, HLF gene, CXCL13 gene and SULT1E1 gene.

In a particular embodiment, the present invention relates to said in vitro prognostic method of the distant relapse-free survival or overall survival in a patient with triple negative breast cancer (TNBC) having received a neoadjuvant chemotherapy (NACT), comprising the determination of the value of the expression of the four following genes: GBP1 gene, HLF gene, CXCL13 gene and SULT1E1 gene.

In a particular embodiment, the present invention relates to said in vitro prognostic method of the distant relapse survival or overall survival of a patient with triple negative breast cancer (TNBC) having received a neoadjuvant chemotherapy (NACT) wherein said gene expression is determined from mRNA or proteins, in particular from mRNA.

In a particular embodiment, the present invention relates to said in vitro prognostic method of the distant relapse survival or overall survival of a patient with triple negative breast cancer (TNBC) having received a neoadjuvant chemotherapy (NACT), wherein said gene expression is determined by a method allowing to measure mRNA quantity such as micro array, PCR or RT-PCR.

In a particular embodiment, the present invention relates to said in vitro prognostic method of the distant relapse survival or overall survival of a patient with triple negative breast cancer (TNBC) having received a neoadjuvant chemotherapy (NACT), wherein said gene expression is determined by an Affymetrix gene array.

In a particular embodiment, the present invention relates to said in vitro prognostic method of the distant relapse survival or overall survival of with triple negative breast cancer (TNBC) having received a neoadjuvant chemotherapy (NACT), wherein said value of the expression of the four following genes GBP1 gene, HLF gene, CXCL13 gene and SULT1E1 gene, is determined in a sample from a biopsy taken from a patient tumor before neoadjuvant chemotherapy.

In a particular embodiment, the present invention relates to said in vitro prognostic method of the distant relapse survival or overall survival of a patient with triple negative breast cancer (TNBC) having received a neoadjuvant chemotherapy (NACT) wherein the four gene corresponding toGBP1 gene, HLF gene, CXCL13 gene and SULT1E1 gene, are respectively represented by the nucleotide sequences SEQ ID NO: 1, SEQ ID NO: 2, SEQ ID NO: 3, and SEQ ID NO: 4.

In a particular embodiment, the present invention relates to said in vitro prognostic method of the distant relapse survival or overall survival of a patient with triple negative breast cancer (TNBC) having received a neoadjuvant chemotherapy (NACT), wherein said value of the expression of the four genes: GBP1 gene, HLF gene, CXCL13 gene and SULT1E1 gene, corresponds to a low value of the expression of the genes SULT1E1 and HLF, and a high value of the expression of the genes GBP1 and CXCL13, measured in a biopsy taken from a patient tumor before neoadjuvant chemotherapy corresponds to an high stromal tumor-infiltrating lymphocytes (Str-TIL) after neoadjuvant chemotherapy, corresponding to a good distant relapse free-survival or overall survival of said patient.

In a particular embodiment, the present invention relates to said in vitro prognostic method of the distant relapse survival or overall survival of a patient with triple negative breast cancer (TNBC) having received a neoadjuvant chemotherapy (NACT), wherein said value of the expression of the four genes: GBP1 gene, HLF gene, CXCL13 gene and SULT1E1 gene, corresponds to a high value of the expression of the genes SULT1E1 and HLF, and a low value of the expression of the genes GBP1 and CXCL13, measured in a biopsy taken from a patient tumor before neoadjuvant chemotherapy corresponds to an low stromal tumor-infiltrating lymphocytes (Str-TIL) after neoadjuvant chemotherapy, corresponding to a short distant relapse free-survival or overall survival of said patient.

In a particular embodiment, the present invention relates to said in vitro prognostic method of the distant relapse survival or overall survival of a patient with triple negative breast cancer (TNBC) having received a neoadjuvant chemotherapy (NACT), comprising the determination of a genomic predictor according to formula:

Genomic predictor=0.288*GBP1 expression+ 0.392*CXCL13 expression−1.027*HLF expression−1.726*SULT1E1 expression, for the estimation of prognosis of distant relapse-free survival or overall survival of a patient with triple negative breast cancer (TNBC) having received a neoadjuvant chemotherapy (NACT).

In a particular embodiment, the present invention relates to an in vitro prognostic method of the distant relapse survival or overall survival of a patient with triple negative breast cancer (TNBC) having received a neoadjuvant chemotherapy (NACT), wherein when the genomic predictor for a patient is strictly less than 0.51, the patient has a poor prognosis.

In a particular embodiment, the present invention relates to said in vitro prognostic method of the distant relapse survival or overall survival of a patient with triple negative breast cancer (TNBC) having received a neoadjuvant chemotherapy (NACT), wherein when the genomic predictor for a patient is more than or equal to 0.51, the patient has a good prognosis.

The present invention also relates to a kit for the in vitro prognostic method of the distant relapse survival or overall survival of a patient with triple negative breast cancer (TNBC) having received a neoadjuvant chemotherapy (NACT) according to claim, comprising:
- 4 pairs of primers corresponding to the 4 genes GBP1, HLF, CXCL13 and SULT1E1,
- at least one pair of primers corresponding to a housekeeping gene selected from the group comprising 18S rRNA, ACTB, HPRT1, HSPCB, PPIA, PUM1, RPS13, SDHA and TBP,
- a reverse transcriptase,
- oligonucleotides,
- a polymerase
- and suitable buffer solutions.

The present invention also relates to an use of the value of the expression of the four genes: GBP1 gene, HLF gene, CXCL13 gene and SULT1E1 gene measured in a biopsy taken before a neoadjuvant chemotherapy (NACT), for predicting the level of stromal tumor-infiltrating lymphocytes (Str-TIL) in a patient with triple negative breast cancer (TNBC) after a NACT.

3. Training Phase
3.1 Materiel
3.1.1 Description of the Training Population

Figure 1B:
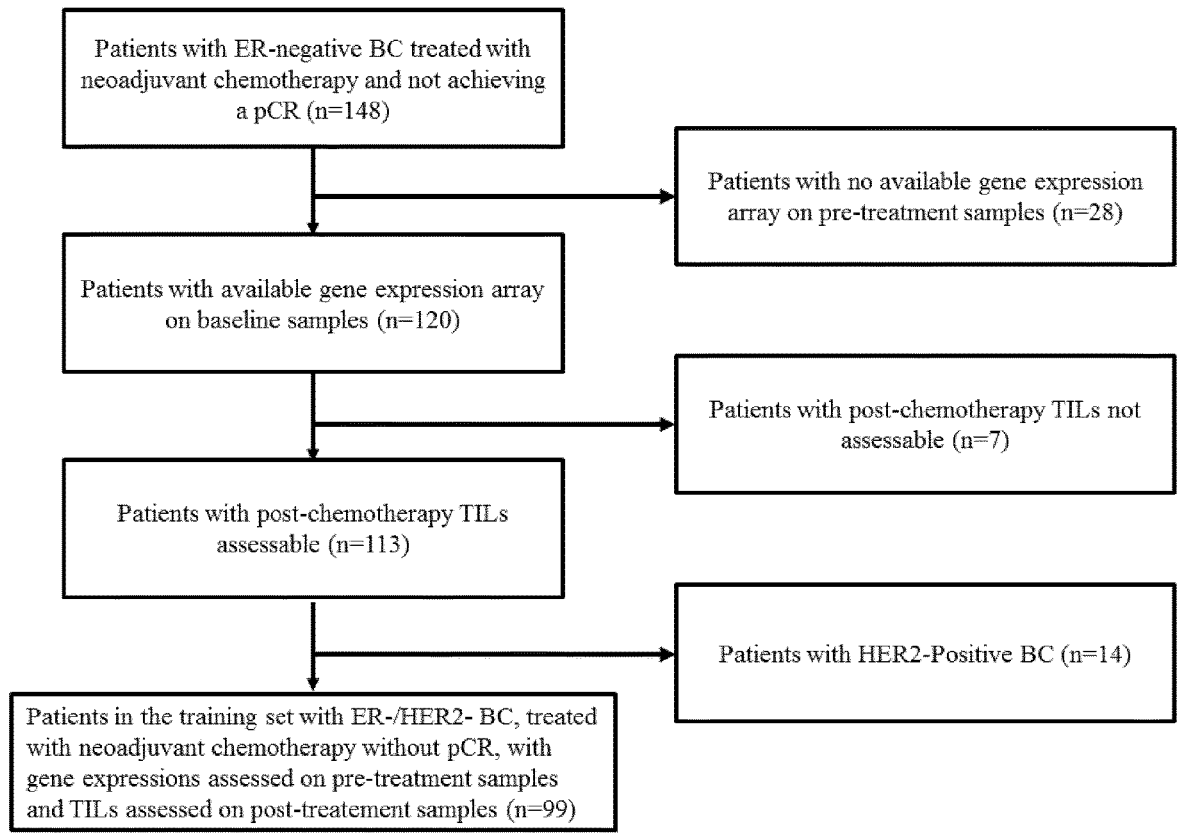

The participants' flow chart of the training dataset is shown in FIGS. 1a and 1b.

The baseline characteristics of the 99 eligible patients (ER-/HER2-) in the training dataset are presented in Table 1. The baseline characteristics of patients included in the training dataset are shown in Table 32 (n=113).

TABLE 1

| | Baseline characteristics of eligible patients in the training dataset | | |
|---|---|---|---|
| | TOP<br>n = 30 | MDACC<br>n = 69 | All trials<br>n = 99 |
| Age, years | | | |
| Mean (SD) | 47 (11.7) | 50 (11.1) | 49 (11.3) |
| Median (Q1-Q3) | 44 (38-56) | 50 (40-59) | 47 (40-59) |
| Min-Max | 27-67 | 31-75 | 27-75 |
| cT | | | |
| T1 | 3 (10%) | 2 (3%) | 5 (5%) |
| T2 | 22 (73%) | 38 (55%) | 60 (61%) |
| T3 | 3 (10%) | 16 (23%) | 19 (19%) |
| T4 | 2 (7%) | 13 (19%) | 15 (15%) |
| cN | | | |
| N0 | 16 (53%) | 19 (28%) | 35 (35%) |
| N+ | 14 (47%) | 50 (72%) | 64 (65%) |
| ER status | | | |
| Negative | 30 (100%) | 69 (100%) | 99 (100%) |
| Positive | 0 (0%) | 0 (0%) | 0 (0%) |
| PR status | | | |
| Negative | 18 (100%) | 69 (100%) | 87 (100%) |
| Positive | 0 (0%) | 0 (0%) | 0 (0%) |
| Missing | 12 | 0 | 12 |
| Histologic grade | | | |
| 1-2 | 5 (17%) | 12 (18%) | 17 (17%) |
| 3 | 25 (83%) | 56 (82%) | 81 (83%) |
| Missing | 0 | 1 | 1 |
| Post-chemo Stromal TILs | | | |
| Mean (SD) | 24 (21.0) | 20 (21.6) | 21 (21.4) |
| Median (Q1-Q3) | 20 (10-29) | 10 (5-30) | 10 (5-30) |
| Min-Max | 0-80 | 0-90 | 0-90 |
| No. of relapses | 9 (31%) | 36 (52%) | 45 (46%) |

TABLE 1-continued

Baseline characteristics of eligible patients in the training dataset

|  | TOP<br>n = 30 | MDACC<br>n = 69 | All trials<br>n = 99 |
| --- | --- | --- | --- |
| No. of deaths | 7 (24%) | 36 (52%) | 43 (44%) |
| Median follow-up in years (Q1-Q3) | 3.15 (2.12-3.85) | 8.13 (7.46-9.61) | 7.59 (3.74-8.82) |
| GEO | GSE16446 | GSE25066<br>GSE20271 |  |
| References | Desmedt et al[8] | Hatzis et al[7] |  |

Data are mean (SD), median (Q1-Q3), min-max, or n (%).
Patients of the training set were from MDACC neoadjuvant series and TOP study.
[7,8]SD, standard deviation;
Q1, 25th percentile;
Q3, 75th percentile;
Min, Minimum;
Max, Maximum;
cT, clinical tumor size;
cN, clinical nodal status;
ER, estrogen receptor;
PR, progesterone receptor;
HER2, human epidermal growth factor receptor 2;
TILs, tumor-infiltrating lymphocytes;
GEO, gene expression omnibus;
TOP, Trial of Principle;
MDACC, MD Anderson Cancer Center.

3.1.2 Genomic Data

The complete genomic data are publically available on the Gene Expression Omnibus (GEO, http://www.ncbi.nlm.nih.gov/geo/) in the series GSE16446 for TOP samples; in the series GSE25066 and GSE20271 for MDACC samples. We performed data processing on the 113 patients with stromal TIL data available (99 patients were TNBC and 14 were HER2+, see FIGS. 1a and 1b, GEO accessions of the 14 HER2+ patients are shown in Table 32).

3.1.2.1 Quality checks before normalization.

Figure 2:
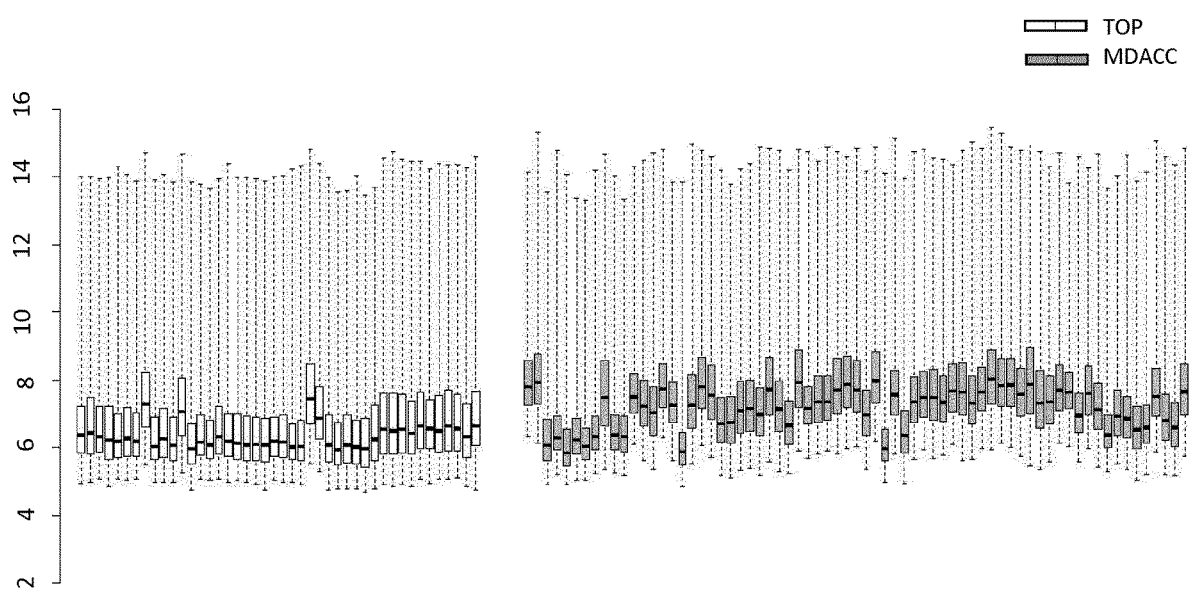
Figure 3:
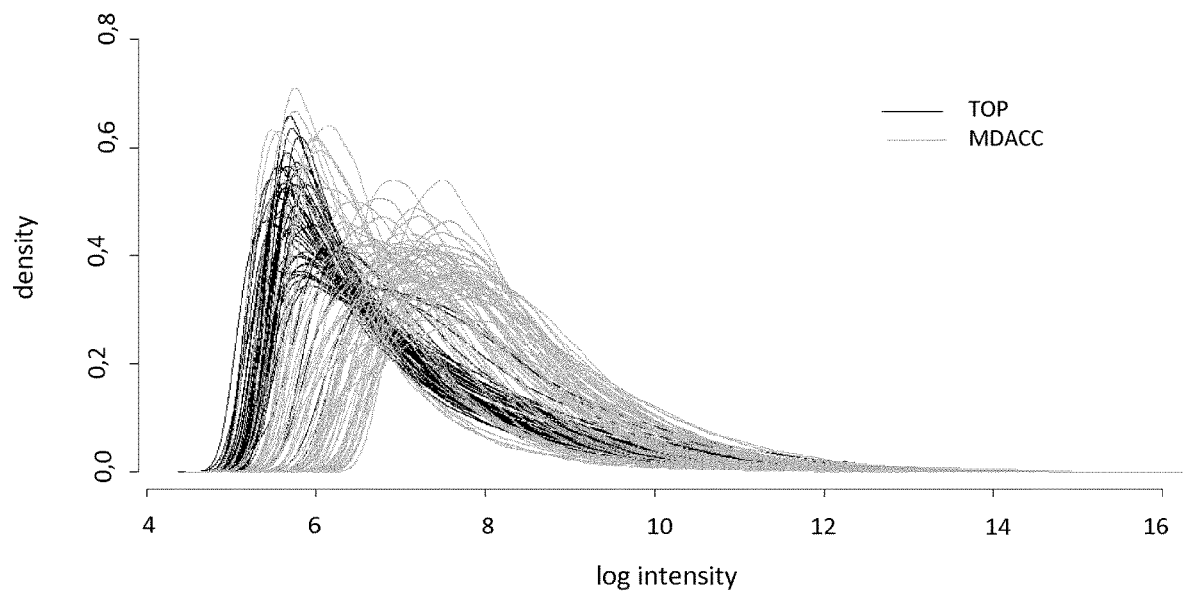

For quality checks before normalization, we used boxplots and plots of the density estimates of the raw probe level data comparing all arrays. Plots are shown in FIG. 2 and FIG. 3.

3.1.2.2 Separate Data Normalization Using fRMA

Figure 4:
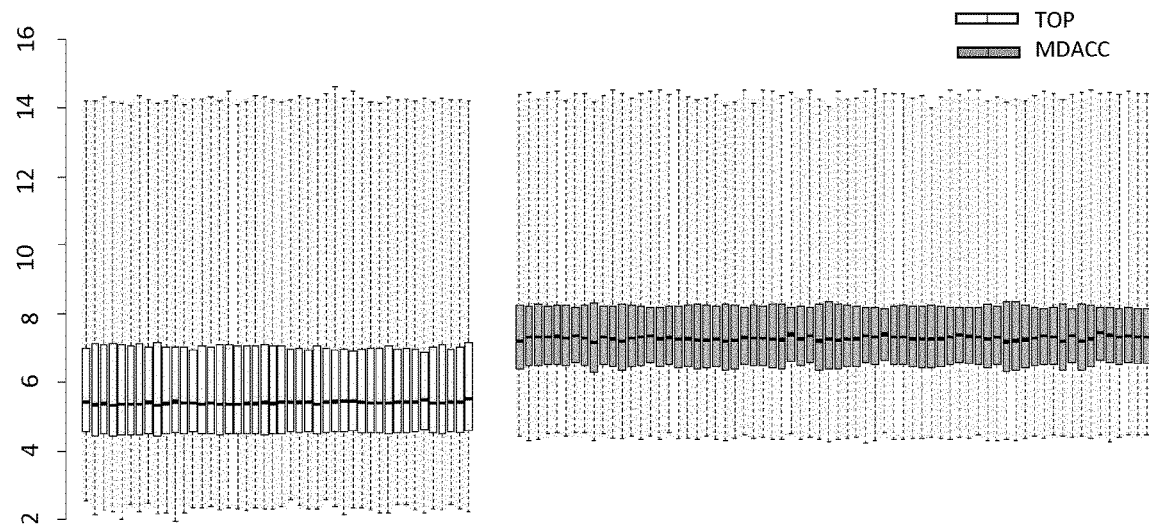
Figure 5:
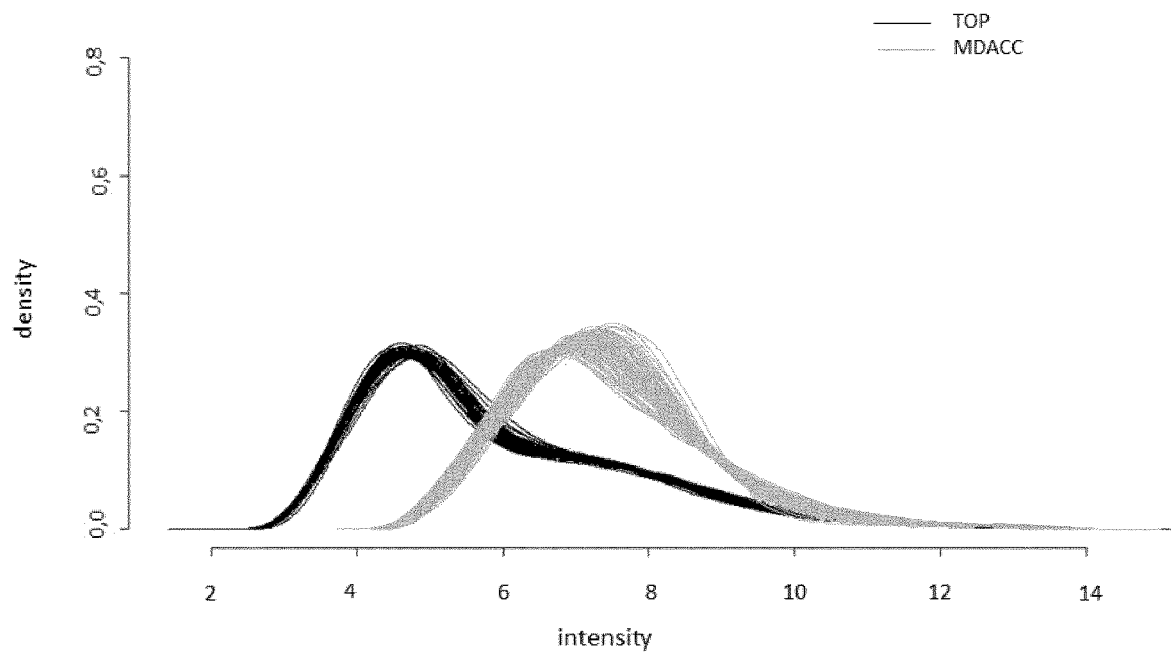

We applied frozen robust multiarray analysis (fRMA) preprocessing algorithm to normalize the two datasets separately. This method is implemented in the R package 'frma'. For quality checks after fRMA, we used boxplots and plots of the density estimates of the normalized data comparing all arrays. Plots are shown in FIG. 4 and FIG. 5.

3.1.2.3 Cross-Platform Normalization

Figure 6:
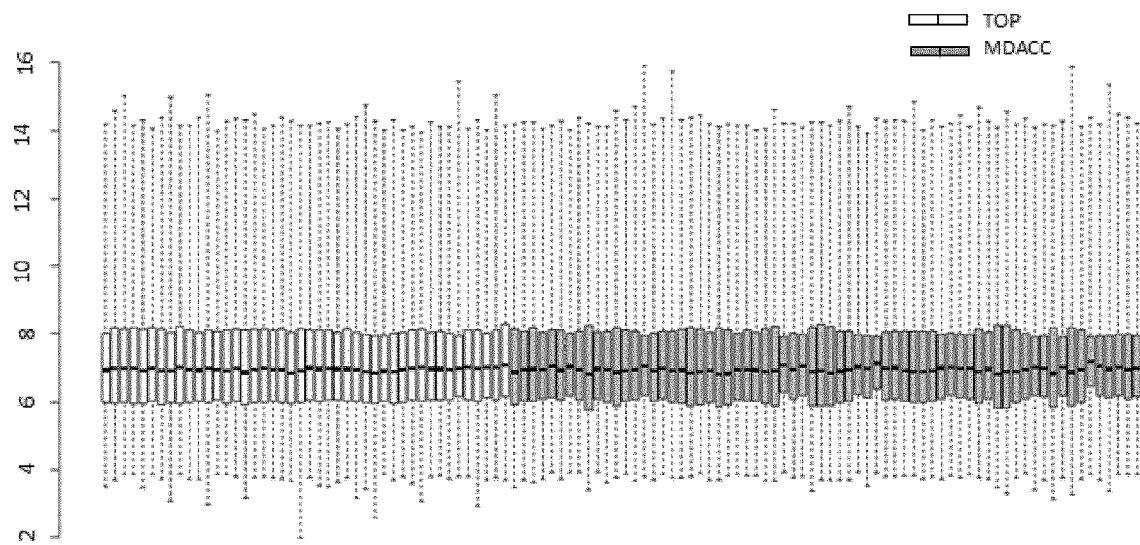
Figure 7:
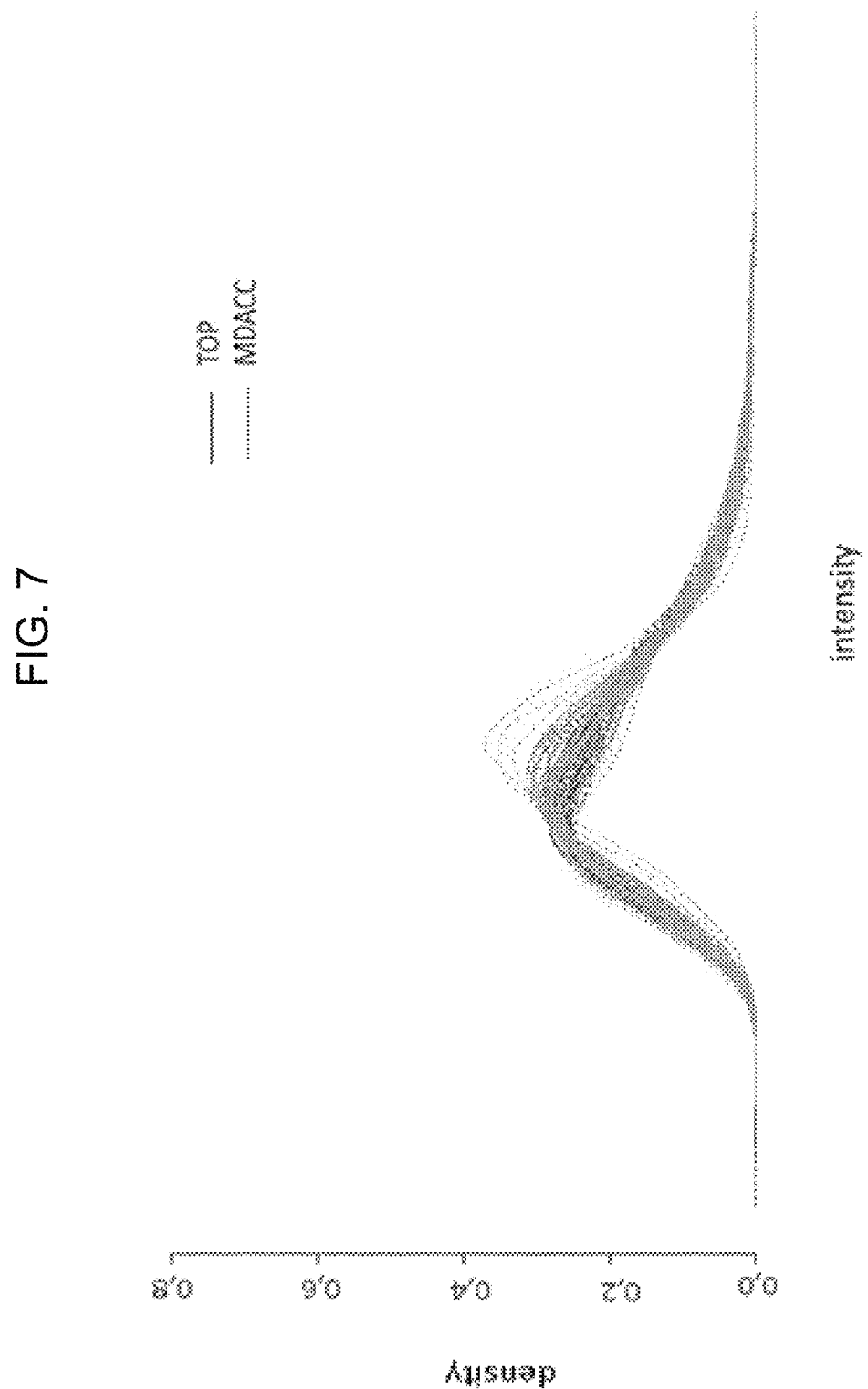

We merged the two datasets using Cross-platform normalization (XPN) methods for batch effect removal [3]. This method is implemented in the R package 'inSilicoMerging'. For quality checks after cross-platform normalization, we used boxplots and plots of the density estimates of the normalized data comparing all arrays. Plots are shown in FIG. 6 and FIG. 7.

3.1.2.4 Unspecified Filtering

Unspecified filtering consists in including only the 10 000 most variable genes (standard deviation) for further analysis. It was performed once and for all, using gene expressions from 113 samples: the 10 000 genes selected will be used for all the further analysis.

3.2 Methods and Results 3.2.1 Difference in Stromal TIL after Chemotherapy Between MDACC Samples and TOP Samples TILs were quantified on RD after NACT in H&E slides from surgical samples from MDACC neoadjuvant series and TOP trial (training set). All mononuclear cells (i.e., lymphocytes and plasma cells) in the stromal compartment within the borders of the invasive tumor were evaluated and reported as a percentage (TILs score). TILs outside of the tumor border, around DCIS and normal breast tissue, as well as in areas of necrosis, if any, were not included in the scoring. TILs were assessed as a continuous measure (score). For each surgical specimen, all the slides containing invasive RD have been evaluated. The reproducibility of this method has been described 12. H&E slides from TOP samples have been sent to IEO, where they have been independently read for TIL-infiltration by two investigators (CC and GP). MDACC H&E slides have been read on-site by two investigators (CC and BS).

Figure 8:
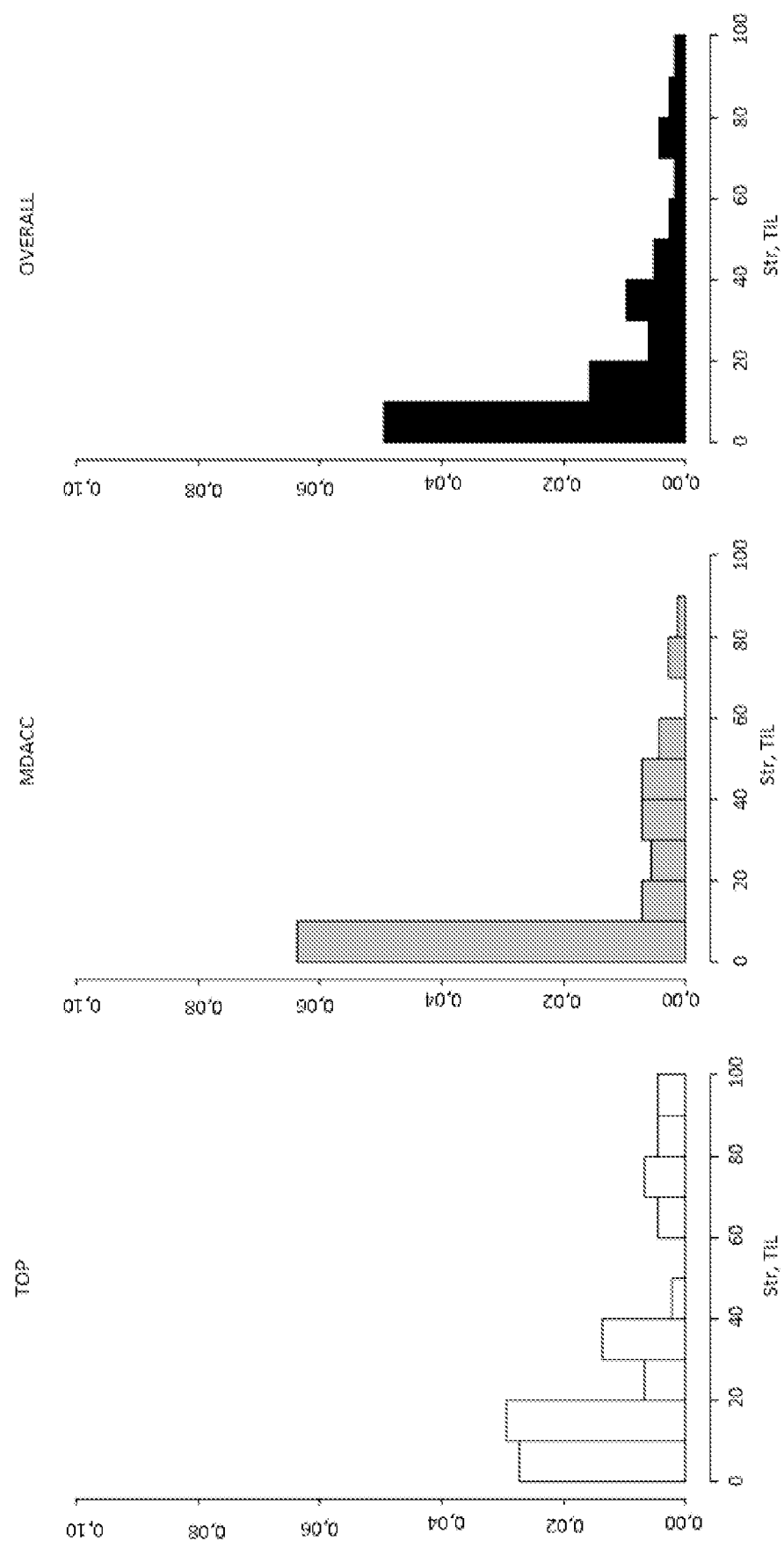

Difference in stromal TIL after chemotherapy between MDACC samples and TOP samples was assessed on the 113 patients in the training dataset. Stromal TIL significantly deviates from normality (Shapiro-Wilk normality test p-value=9.771e-11). There is a statistically significant difference in stromal TIL between MDACC samples and TOP samples (Wilcoxon rank sum test with continuity correction p-value=0.005027). Summary statistics of stromal TIL in TOP samples, MDACC samples and overall are given in Table 2. Histograms of stromal TIL in TOP samples, MDACC samples and overall are shown in FIG. 8.

TABLE 2

Summary statistics of stromal TIL in TOP samples, MDACC samples and overall

|  | TOP<br>N = 44 | MDACC<br>N = 69 | Overall<br>N = 113 |
| --- | --- | --- | --- |
| Mean | 32 | 20 | 25 |
| SD | 28.5 | 21.6 | 25.1 |
| Median | 20 | 10 | 15 |
| Q1-Q3 | 10-40 | 5-30 | 5-40 |
| Min-Max | 0-95 | 0-90 | 0-95 |

3.2.2 Box-Cox Transformation

The Box-Cox transformation is a useful data transformation technique used to stabilize variance and make the data more normal distribution-like. Box-Cox transformation applies only to positive variables, so we applied it on (Stromal TIl+1).

The univariate generalized linear model on which the Box-Cox transformation was applied included one at a time of the 10 000 most varying genes (see 3.1.2.4), center (Bordet vs. MDACC) and HER2 status (− vs. +). The model was applied on data from the 113 patients of the training dataset.

The multivariate generalized linear model on which the Box-Cox transformation was applied on 113 patients from the training dataset and included one at a time of the 10 000 most varying genes and center (Bordet vs. MDACC), age (continuous), cT (0-1-2 vs. 3-4), cN (0 vs. +), grade (1-2 vs. 3) and HER2 status (− vs. +). The model was applied on data from the 113 patients of the training dataset.

The Box-Cox transformation formula is given below:

$$y^{(\alpha)} = \begin{cases} \dfrac{y^\alpha - 1}{\alpha} & \text{if } \alpha \neq 0 \\ \ln(y) & \text{if } \alpha = 0 \end{cases}$$

Summary statistics of α values derived from 10 000 Box-Cox transformations are given in Table 3. We chose to set α at the median value for all the genes (10 000) in the multivariate analysis; consequently α=0.2000 for all the following models.

TABLE 3

Summary statistics of α values derived from 10 000 Box-Cox transformations

|  | Univariate | Multivariate |
|---|---|---|
| Mean | 0.1932 | 0.1987 |
| SD | 0.00641 | 0.00586 |
| Median | 0.1900 | 0.2000 |
| Q1-Q3 | 0.1900-0.2000 | 0.2000-0.2000 |
| Min-Max | 0.1400-0.2200 | 0.1400-0.2300 |

3.2.3 Procedure 1: Univariate Selection with Adjustment
Procedure 1 steps:
1. To fit a general linear model to model the continuous level of stromal TIL in the post chemotherapy samples using complete cases. Stromal TIL is transformed using Box-Cox transformation.
2. To correct for multiple comparisons using False Discovery Rate (FDR) method [Benjamini Y, Hochberg Y (1995) Controlling the False Discovery Rate: A Practical and Powerful Approach to Multiple Testing. J R Stat Soc Ser B Methodol 57:289-300.] (Bonferroni p-values are reported for information purposes only).
3. To report genes that achieved the selection criterion of a corrected p-value <0.05.

3.2.3.1 Univariate Analysis
3.2.3.1.1 Triple Negative Patients
There were 99 patients identified as triple negative. We fitted a general linear model to model the continuous level of stromal TIL in the post chemotherapy sample as a function of gene expression while controlling for the effect of a potential confounder that is the center (Bordet vs. MDACC). Summary of the 79 genes achieving selection criterion (corrected p-value <0.05) are shown in Table 33.

3.2.3.1.2 all Patients Stratified on HER2 Status
There were 113 patients used to build the model. We fitted a general linear model to model the continuous level of stromal TIL in the post chemotherapy sample as a function of gene expression while controlling for the effect of potential confounders that are center (Bordet vs. MDACC), and HER2 status (− vs. +). Summary of the 114 genes achieving selection criterion (corrected p-value <0.05) are shown in Table 34.

3.2.3.2 Multivariate Analysis
3.2.3.2.1 Triple Negative Patients
There were 99 patients identified as triple negative. We fitted a general linear model to model the continuous level of stromal TIL in the post chemotherapy sample as a function of gene expression while controlling for the effect of potential confounders that are center (Bordet vs. MDACC), age (continuous), cT (0-1-2 vs. 3-4), cN (0 vs. +) and grade (1-2 vs. 3). Summary of the 41 genes achieving selection criterion (corrected p-value <0.05) are shown in Table 35.

3.2.3.2.2 all Patients Stratified on HER2 Status
There were 113 patients used to build the model. We fitted a general linear model to model the continuous level of stromal TIL in the post chemotherapy sample as a function of gene expression while controlling for the effect of a potential confounder that are center (Bordet vs. MDACC), age (continuous), cT (0-1-2 vs. 3-4), cN (0 vs. +) and grade (1-2 vs. 3) and HER2 status (− vs. +). Summary of the 60 genes achieving selection criterion (corrected p-value <0.05) are shown in Table 36.

3.2.4 Procedure 2: Model Selection Using Penalization
The purpose of the shrinkage is to prevent overfit arising due to either collinearity of the covariates or high-dimensionality.

We chose to apply L1 absolute value ("lasso") penalty as described by Tibshirani et al. [Tibshirani R (1996) Regression Shrinkage and Selection via the Lasso. J R Stat Soc Ser B Methodol 58:267-288] [Tibshirani R, others (1997) The lasso method for variable selection in the Cox model. Stat Med 16:385-395.].

Appling an L1 penalty tends to results in many regression coefficients shrunk to zero and few other regression coefficients with comparatively little shrinkage hence this method allows selection of the most significant genes.

The amount of shrinkage is determined by the tuning parameter λ. A value of zero means no shrinkage, in this case, the method is identical to maximum likelihood estimation. A value of infinity means infinite shrinkage, in this case, all regression coefficients are set to zero. It is important to note that shrinkage methods are generally not invariant to the relative scaling of the covariates. We standardized the covariates before fitting the model. This standardization makes sure that each covariate is affected more or less equally by the penalization. Note that the regression coefficients reported here have been scaled back and correspond to the original scale of the covariates.

We included only the 10 000 most variable genes (standard deviation) in this analysis (see 3.1.2.4).

The appropriate generalized linear model for the response variable stromal TIL is linear. We penalized all the gene expressions covariates. Additional clinical covariates included are center (Bordet vs. MDACC), age (continuous), cT (0-1-2 vs. 3-4), cN (0 vs. +) and grade (1-2 vs. 3). Those variables were not penalized. The penalization procedure was performed on 98 patients among the 99 eligible patients in the training dataset (one missing grade).
Stromal TIL is Transformed Using Box-Cox Transformation.
3.2.4.1 the Choice of Tuning Parameter λ
Model Selection Using Penalization
The purpose of the shrinkage is to prevent overfit arising due to either collinearity of the covariates or high-dimensionality. We chose to apply L1 absolute value ("lasso")

penalty as described by Tibshirani et al. Appling an L1 penalty tends to results in many regression coefficients shrunk to zero and few other regression coefficients with comparatively little shrinkage hence this method allows selection of the most significant genes. The amount of shrinkage is determined by the tuning parameter $\lambda$. A value of zero means no shrinkage, in this case, the method is identical to maximum likelihood estimation. A value of infinity means infinite shrinkage; in this case, all regression coefficients are set to zero (FIG. 44). It is important to note that shrinkage methods are generally not invariant to the relative scaling of the covariates. We standardized the covariates before fitting the model. This standardization makes sure that each covariate is affected more or less equally by the penalization. Note that the regression coefficients reported have been scaled back and correspond to the original scale of the covariates. We included only the 10 000 most variable genes (standard deviation) in this analysis. Stromal TILs was transformed using Box-Cox transformation. We penalized all the gene expressions covariates. Additional clinicopathologic covariates included are series (TOP vs. MDACC), age (continuous), cT (0-1-2 vs. 3-4), cN (0 vs. +) and grade (1-2 vs. 3). Those variables were not penalized. The penalization procedure was performed on 98 patients among the 99 eligible patients in the training dataset (one missing grade).

Cross-validation was used to assess the predictive ability of the model described above with different values of the tuning parameter. 10-fold cross-validation was chosen to determine the optimal value of the tuning parameter $\lambda$. The allocation of the subjects to the folds is random. When using L1 optimization, the cross validated likelihood as a function of $\lambda$ very often has several maxima hence it is important to cover a wide range of values (see FIG. 9). The optimal value of $\lambda$ was found equal to 91.5 (see FIG. 10).

3.2.4.2 Genes Selection

Penalization was performed with the optimal value of the tuning parameter $\lambda$. The clinical covariates: center (Bordet vs. MDACC), age (continuous), cT (0-1-2 vs. 3-4), cN (0 vs. +) and grade (1-2 vs. 3) were included in the model but they were not penalized. The 4 selected genes are shown in Table 4.

TABLE 4

Genes selected using penalization

| PROBEID | ENTREZID | Gene name | Symbol | Sign |
|---|---|---|---|---|
| 202269_x_at | 2633 | guanylate binding protein 1, interferon-inducible | GBP1 | +1 |
| 204753_s_at | 3131 | hepatic leukemia factor | HLF | −1 |
| 205242_at | 10563 | chemokine (C—X—C motif) ligand 13 | CXCL13 | +1 |
| 219934_s_at | 6783 | sulfotransferase family 1E, estrogen-preferring, member 1 | SULT1E1 | −1 |

+1 indicates that an increasing gene expression increases the stromal TIL value.
−1 indicates that an increasing gene expression decreases the stromal TIL value.

3.2.5 Genomic Predictor of Post-Chemo TIL 3.2.5.1 Building the Genomic Predictor After model selection and in order to determine the coefficients of the 4 selected genes in the construction of the genomic predictor, we applied a generalized linear model for the response variable stromal TIL on the 4 selected genes and the clinical covariates center (Bordet vs. MDACC), age (continuous), cT (0-1-2 vs. 3-4), cN (0 vs. +) and grade (1-2 vs. 3). The genomic predictor is the linear combination of the genes expressions weighted by the regression coefficients shown in Table 5.

Stromal TIL is Transformed Using Box-Cox Transformation.

TABLE 5

Genes associated with stromal TIL after chemotherapy

| PROBEID | Gene | Description | Coefficient |
|---|---|---|---|
| 202269_x_at | GBP1 | guanylate binding protein 1, interferon-inducible | 0.288 |
| 204753_s_at | HLF | hepatic leukemia factor | −1.027 |
| 205242_at | CXCL13 | chemokine (C—X—C motif) ligand 13 | 0.392 |
| 219934_s_at | SULT1E1 | sulfotransferase family 1E, estrogen-preferring, member 1 | −1.726 |

A positive coefficient indicates that an increasing gene expression increases the stromal TIL value.
A negative coefficient indicates that an increasing gene expression decreases the stromal TIL value.

3.2.5.2 Description of the Genomic Predictor

Figure 11:
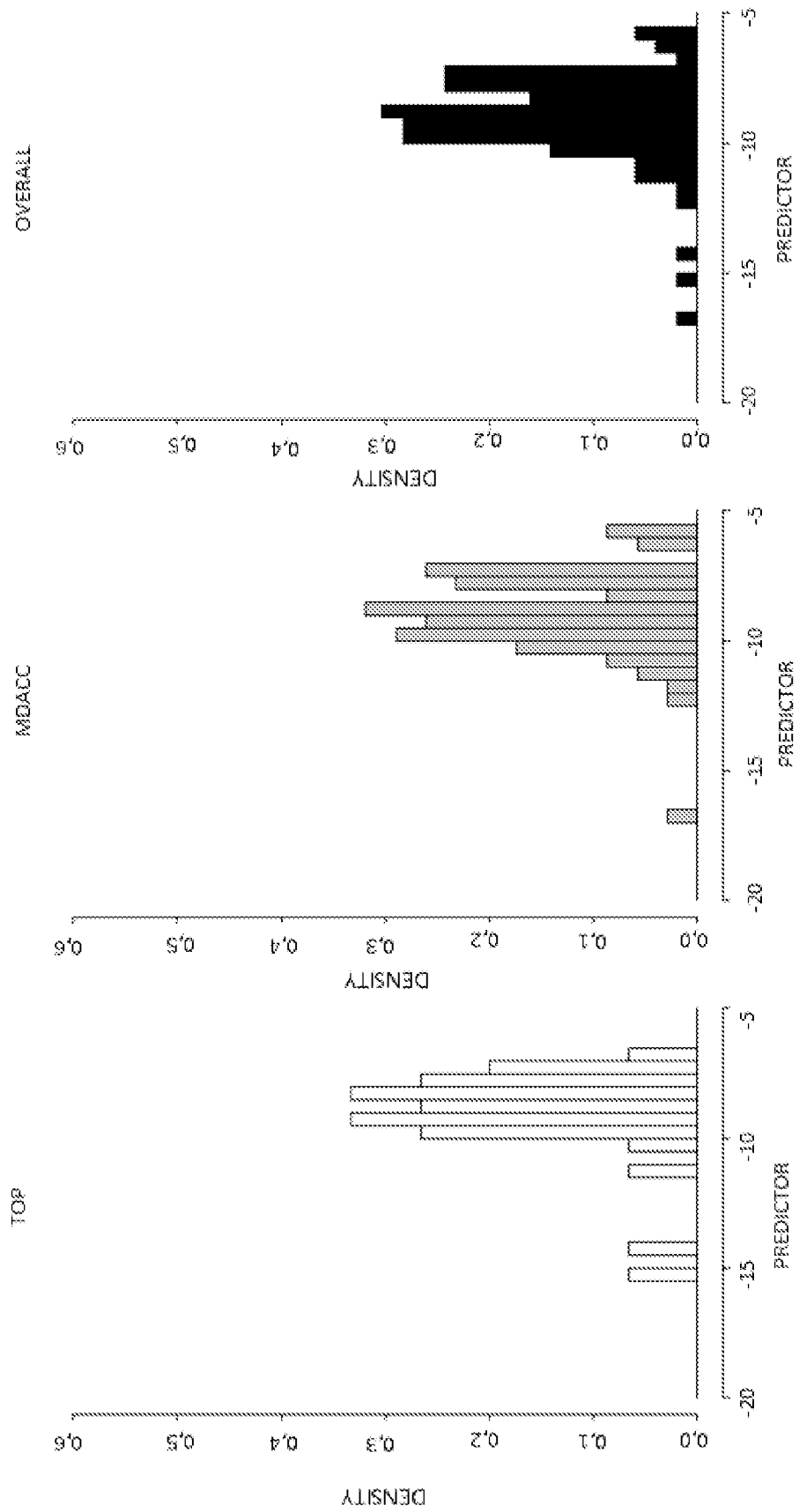

The genomic predictor significantly deviates from normality (Shapiro-Wilk normality test pvalue=1.518e-06). There was no statistically significant difference in the genomic predictor between MDACC samples and TOP samples (Wilcoxon rank sum test with continuity correction p-value=0.888). Summary statistics of the genomic predictor for the 99 TNBC patients in the training dataset are given in Table 6. Histograms of the genomic predictor are shown in FIG. 11.

TABLE 6

Summary statistics of the genomic predictor in TOP samples, MDACC samples and overall

|  | TOP N = 30 | MDACC N = 69 | Overall N = 99 |
|---|---|---|---|
| Mean | −9.06 | −8.92 | −8.96 |
| SD | 1.898 | 1.718 | 1.766 |
| Median | −8.85 | −8.88 | −8.88 |
| Q1-Q3 | −9.50--−7.78 | −9.78--−7.76 | −9.77--−7.73 |
| IQR | 1.71 | 2.02 | 2.03 |
| Min-Max | −15.19--−6.54 | −16.75--−5.82 | −16.75--−5.82 |

To facilitate interpretation of the values of the genomic predictor, we used a transformation to make the genomic predictor lie approximately between 0 (low value) and 1 (high value). The transformation has no effect on the prognostic value of the genomic predictor and is shown in the formula below, where i is the patient's index, $Q_{0.05}$ is the 5% quantile of the genomic predictor in the training samples (99 patients, $Q_{0.05}$=−11.35669) and $Q_{0.95}$ is 95% quantile of the genomic predictor in the training samples (99 patients, $Q_{0.95}$=−6.511546):

$$\text{transformed genomic } predictor_i = \frac{\text{genomic } predictor_i - Q_{0.05}}{Q_{0.95} - Q_{0.05}}$$

Figure 12:
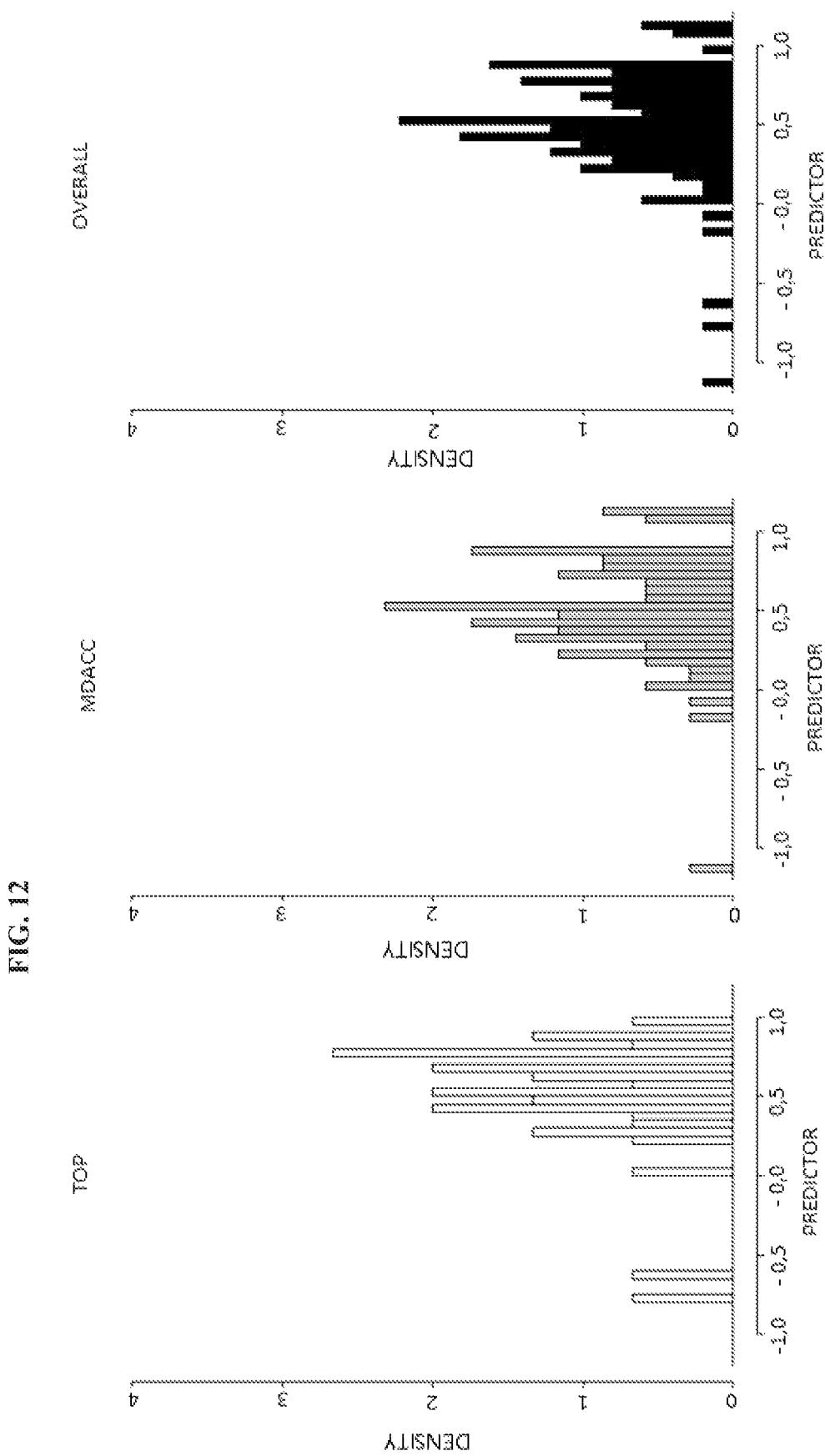

Summary statistics of the transformed genomic predictor in the training dataset are given in Table 7. Histograms of the transformed genomic predictor are shown in FIG. 12.

TABLE 7

Summary statistics of the transformed genomic predictor in TOP samples, MDACC samples and Overall

|  | TOP<br>N = 30 | MDACC<br>N = 69 | Overall<br>N = 99 |
|---|---|---|---|
| Mean | 0.47 | 0.50 | 0.49 |
| SD | 0.392 | 0.355 | 0.364 |
| Median | 0.52 | 0.51 | 0.51 |
| Q1-Q3 | 0.38-0.74 | 0.33-0.74 | 0.33-0.75 |
| IQR | 0.35 | 0.42 | 0.42 |
| Min-Max | −0.79-0.99 | −1.11-1.14 | −1.11-1.14 |

We Used the Transformed Value of the Genomic Predictor within the Rest of the Training Phase, Referring to it as Genomic Predictor.

3.2.5.3 Assessing the Prognostic Value of the Genomic Predictor on Survival

The median follow-up (years) in the training dataset was computed using inverse Kaplan-Meier method applied on distant relapse-free survival (Table 8). There is a statistically significant difference in follow-up between the two cohorts (Logrank p-value=1.68e-13).

TABLE 8

| Follow-up<br>in years | TOP<br>N = 26 | MDACC<br>N = 69 | Overall<br>N = 95 |
|---|---|---|---|
| Median | 3.15 | 8.13 | 7.59 |
| Q1-Q3 | 2.12-3.85 | 7.46-9.61 | 3.74-8.82 |

3.2.5.3.1 Distant Relapse-Free Survival

We assessed the prognostic value of the predictor on distant relapse-free survival (DRFS). In the training dataset, 94 patients had available data. We observed 43 events. Results of the Cox model are shown in Table 9. The Cox model is stratified on center.

TABLE 9

Multivariate cox model - Distant relapse-free survival

|  | HR | 95% IC | P |
|---|---|---|---|
| Age | 1.01 | 0.98-1.03 | 0.6954 |
| cT |  |  | 0.3098 |
| T0-1-2 | 1 |  |  |
| T3-4 | 1.39 | 0.74-2.62 |  |
| cN |  |  | 0.5585 |
| N0 | 1 |  |  |
| N+ | 1.23 | 0.61-2.47 |  |
| Grade |  |  | 0.9996 |
| 1-2 | 1 |  |  |
| 3 | 1.00 | 0.48-2.10 |  |
| Genomic predictor | 0.28 | 0.13-0.63 | 0.0018 |

Figure 13:
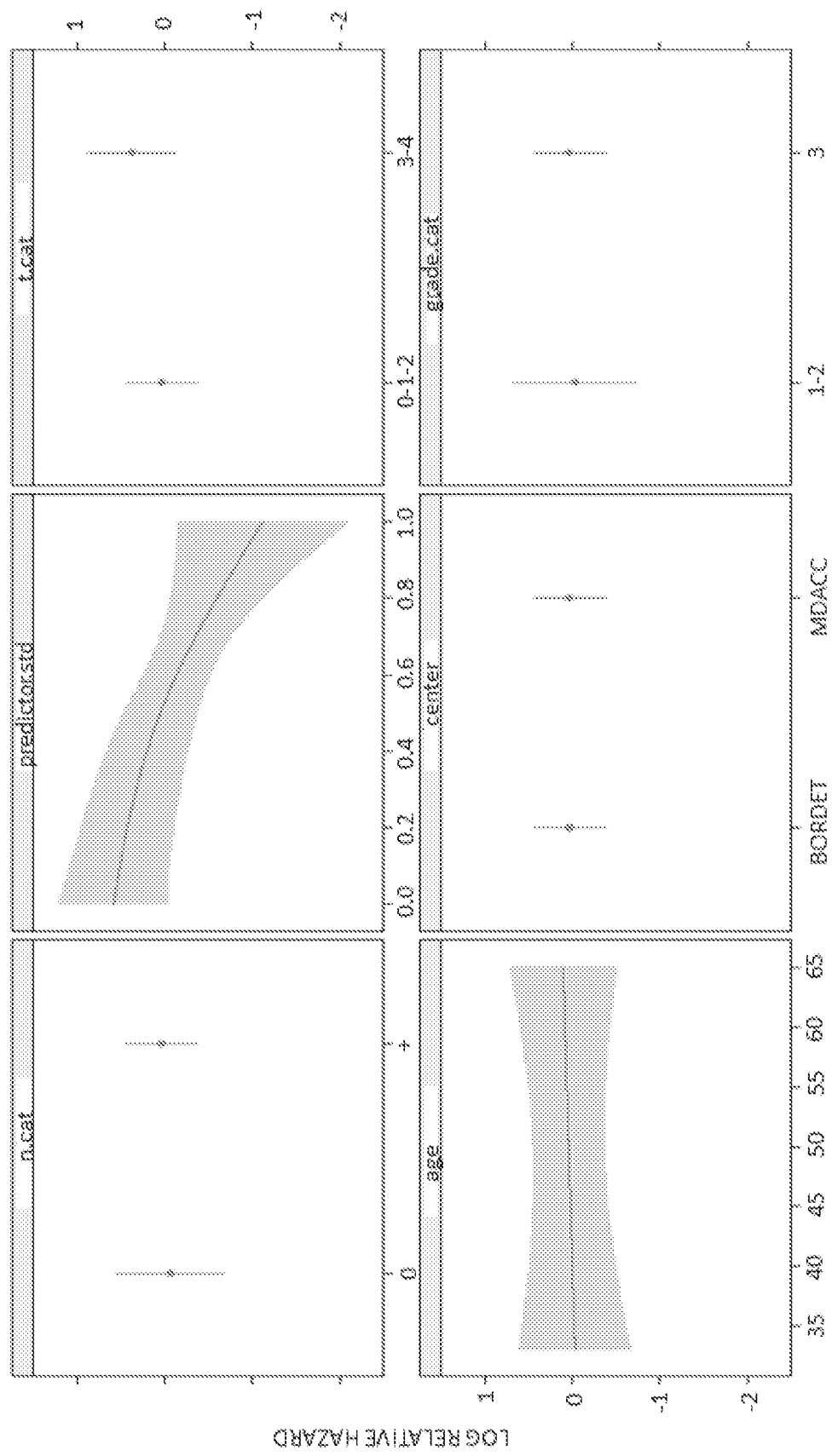

We used restricted cubic splines with 2 degrees of freedom to investigate the non-linear association between distant relapse-free survival and the genomic predictor. There was no significant non-linear effect (p=0.2874). Log-relative hazard profiles are shown in FIG. 13.

3.2.5.3.2 Overall Survival

We assessed the prognostic value of the predictor on overall survival. In the training dataset, 94 patients had available data. We observed 41 events. Results of the Cox model are shown in Table 10. The Cox model is stratified on center.

TABLE 10

Multivariate cox model - Overall survival

|  | HR | 95% IC | p |
|---|---|---|---|
| Age | 1.02 | 0.99-1.05 | 0.2806 |
| cT |  |  | 0.2025 |
| T0-1-2 | 1 |  |  |
| T3-4 | 1.54 | 0.79-2.97 |  |
| cN |  |  | 0.5544 |
| N0 | 1 |  |  |
| N+ | 1.24 | 0.61-2.54 |  |
| Grade |  |  | 0.5033 |
| 1-2 | 1 |  |  |
| 3 | 0.78 | 0.38-1.61 |  |
| Genomic predictor | 0.35 | 0.16-0.75 | 0.0072 |

Figure 14:
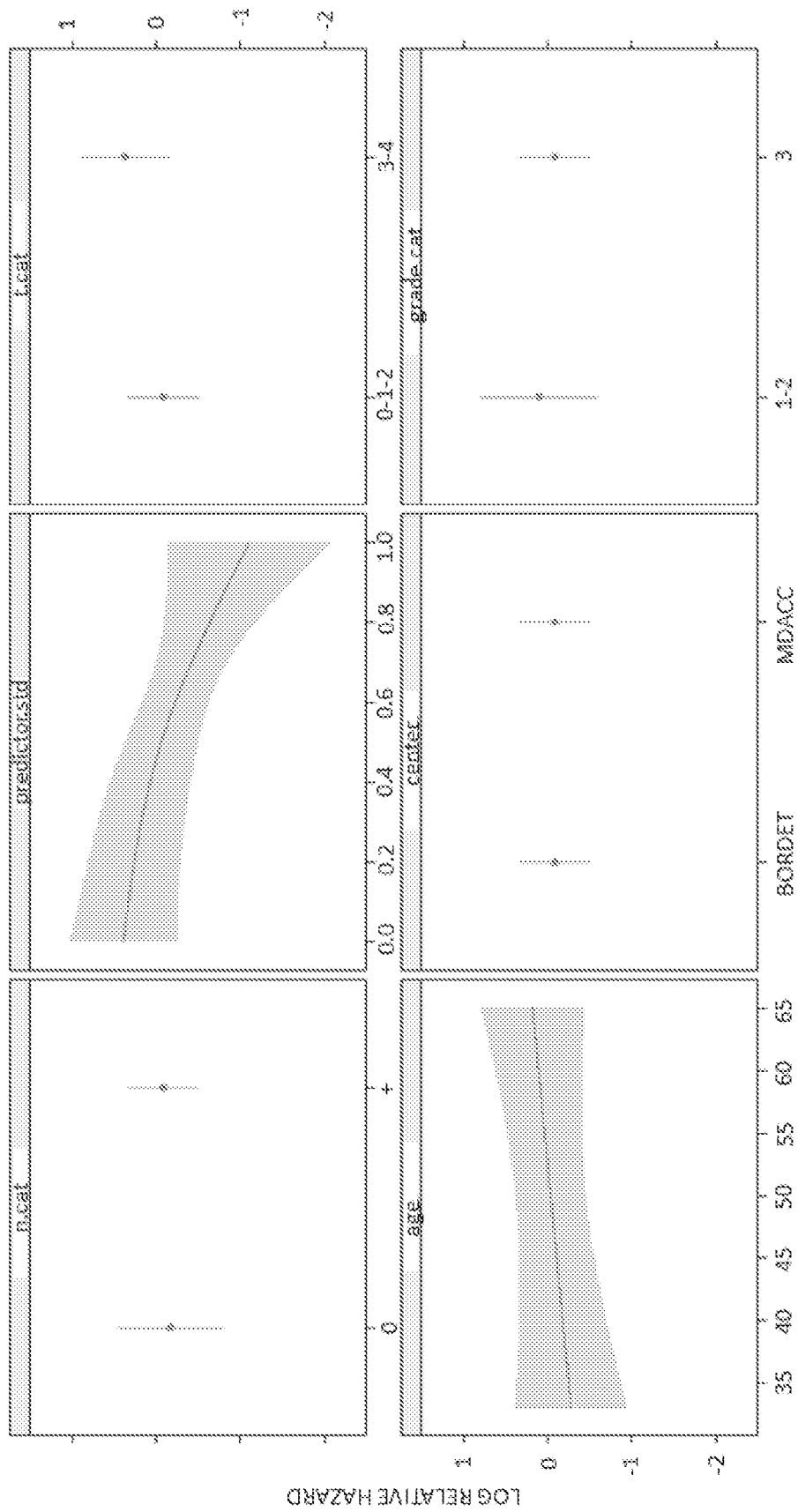

We used restricted cubic splines with 2 degrees of freedom to investigate the non-linear association between overall survival and the genomic predictor. There was no significant nonlinear effect (p=0.3057). Log-relative hazard profiles are shown in FIG. 14.

3.2.5.4 Building Risk Groups
3.2.5.4.1 Cut-Offs
We build risk groups based on:
1. Tertiles (33.33%, 66.66%), referred to hereafter as TER $$\begin{cases} \text{Genomic predictor} < 0.40 & \text{poor prognosis} \\ 0.40 \leq \text{Genomic predictor} < 0.67 & \text{intermediate prognosis} \\ \text{Genomic predictor} \geq 0.67 & \text{good prognosis} \end{cases}$$

2. Median (50%), referred to hereafter as MED $$\begin{cases} \text{Genomic predictor} < 0.51 & \text{poor prognosis} \\ \text{Genomic predictor} \geq 0.51 & \text{good prognosis} \end{cases}$$

3. Quantiles (27%, 73%) [Cox DR (1957) Note on Grouping. J Am Stat Assoc 52:543-547. doi:10.2307/2281704], referred to hereafter as COX $$\begin{cases} \text{Genomic predictor} < 0.35 & \text{very poor prognosis} \\ 0.35 \leq \text{Genomic predictor} < 0.74 & \text{intermediate prognosis} \\ \text{Genomic predictor} \geq 0.74 & \text{very good prognosis} \end{cases}$$

The Cut-Offs Defined Above are Frozen for all the Study.

3.2.5.4.2 Distant Relapse-Free Survival

Figure 15:
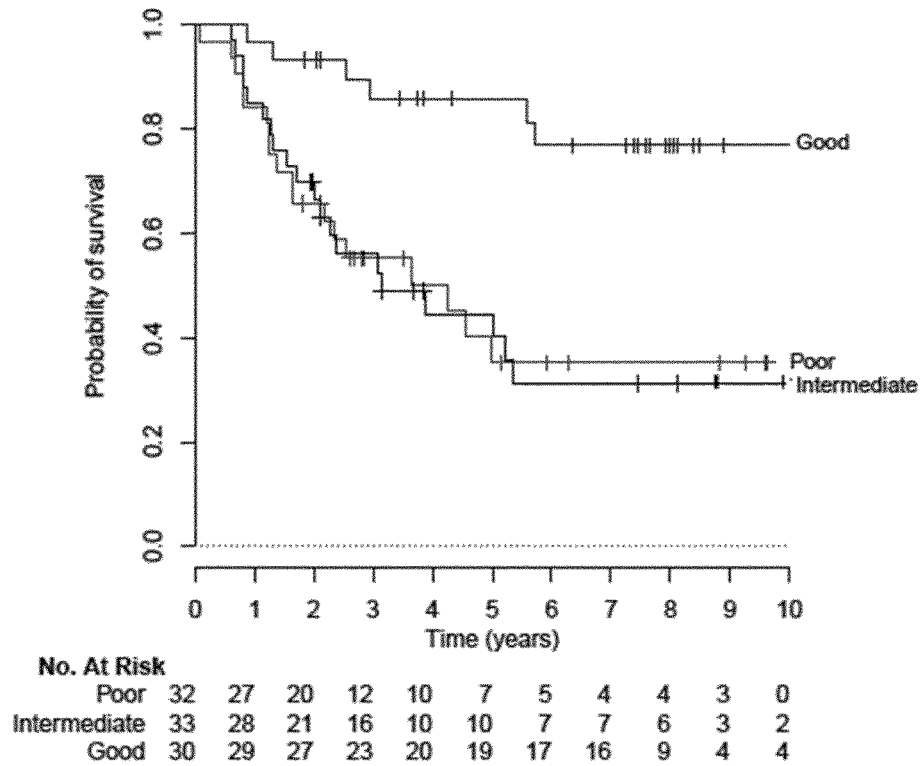
Figure 16:
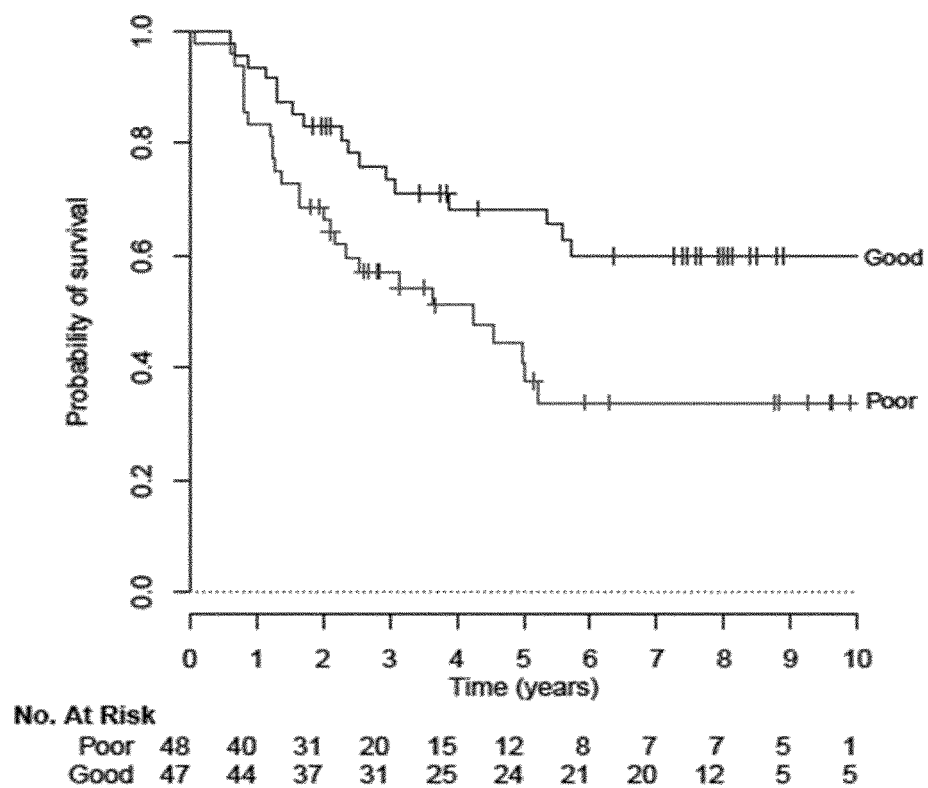
Figure 17:
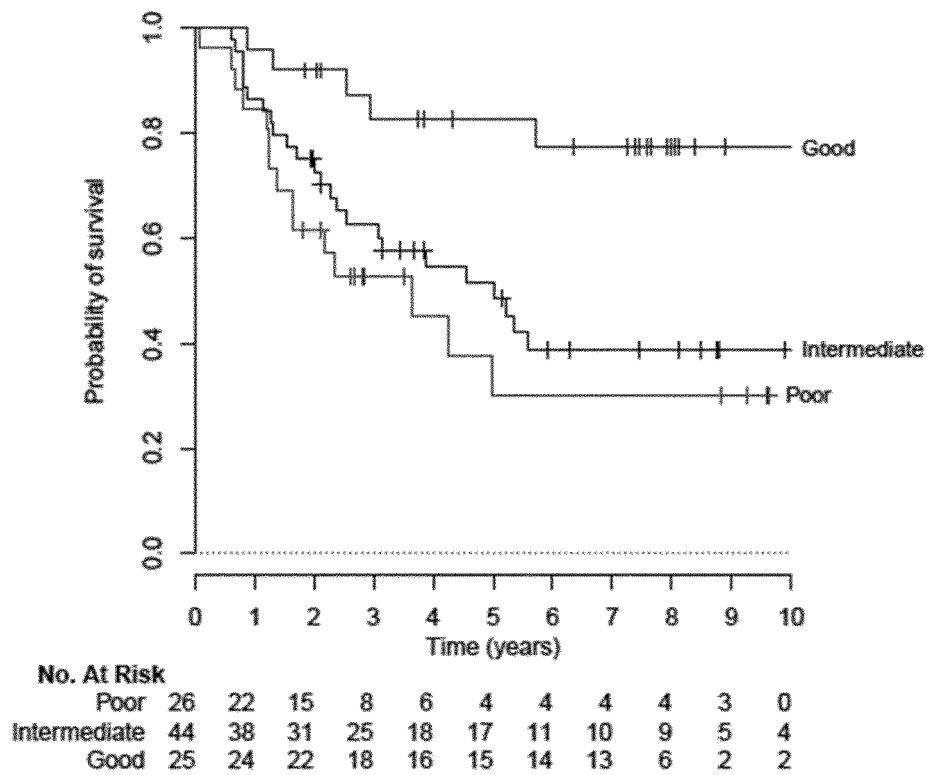

Kaplan-Meier distant relapse-free survival curves of the three risk groups according to the different cut-offs are shown in FIG. 15, FIG. 16 and FIG. 17.

3.2.5.4.3 Overall Survival

Figure 18:
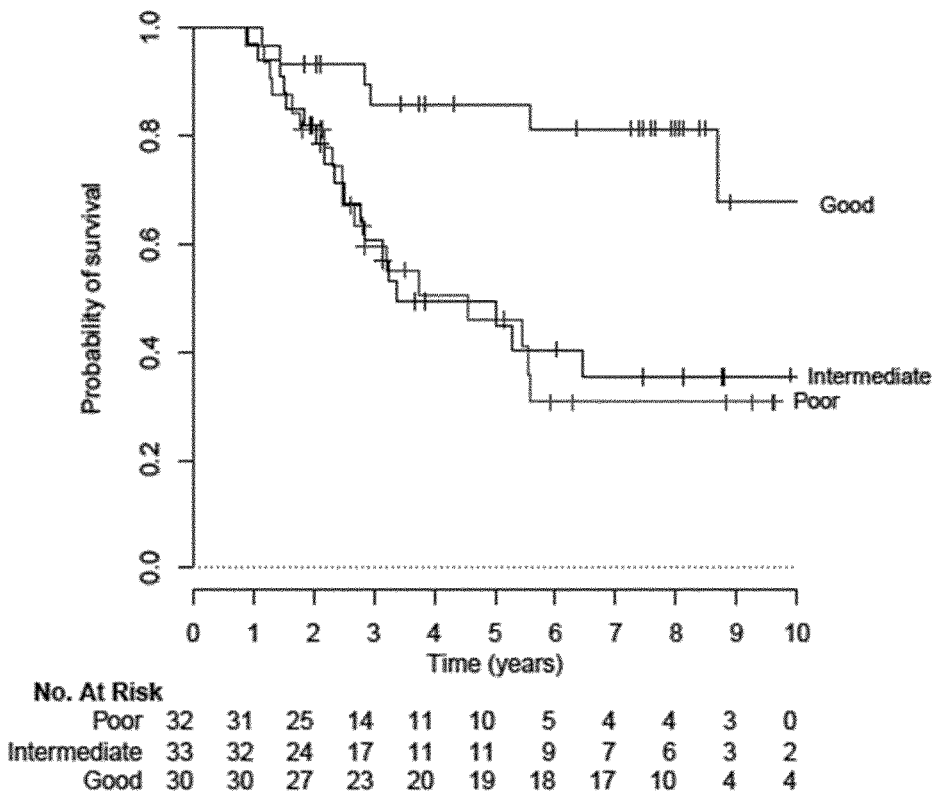
Figure 19:
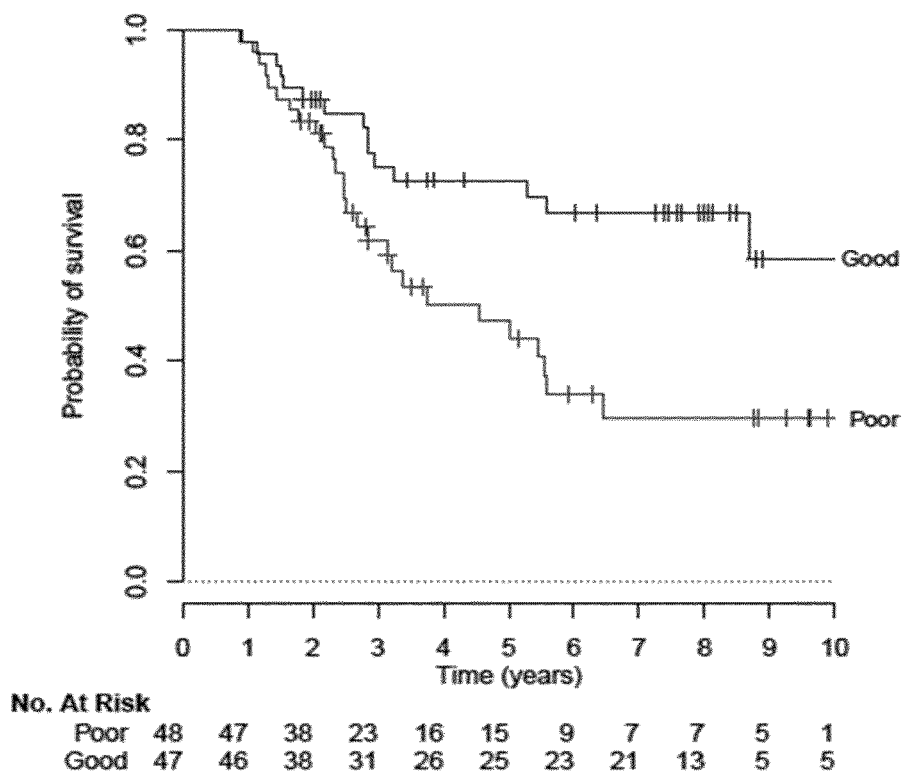
Figure 20:
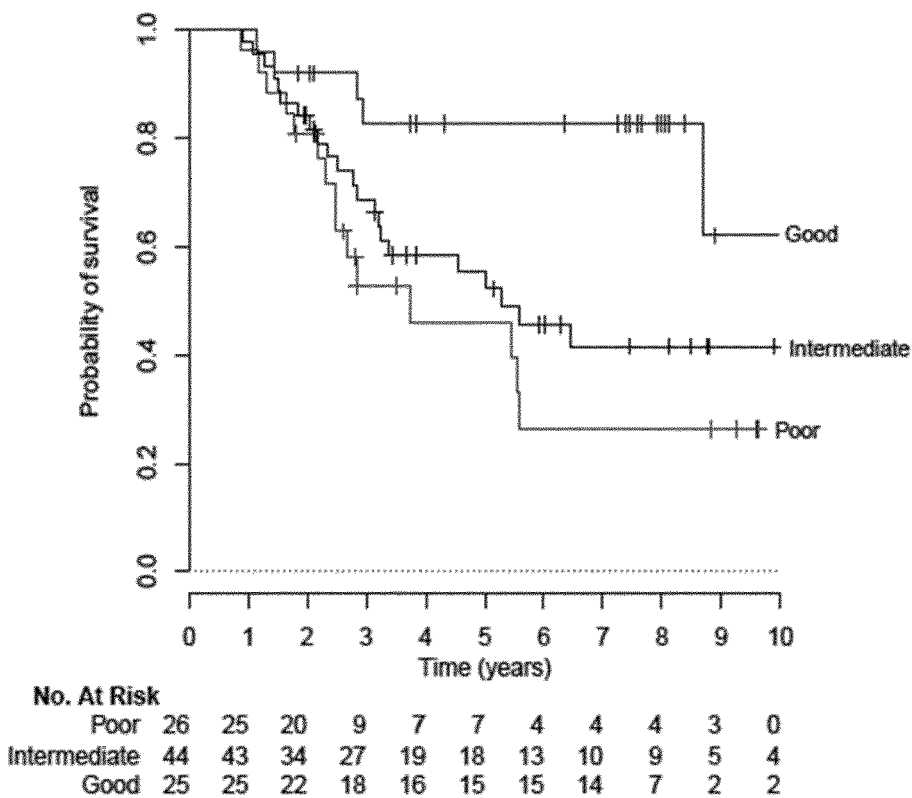

Kaplan-Meier overall survival curves of the three risk groups according to the different cutoffs are shown in FIG. 18, FIG. 19 and FIG. 20.

3.2.5.5 Testing for Correlations
3.2.5.5.1 Gene—Gene Correlation

Figure 21:
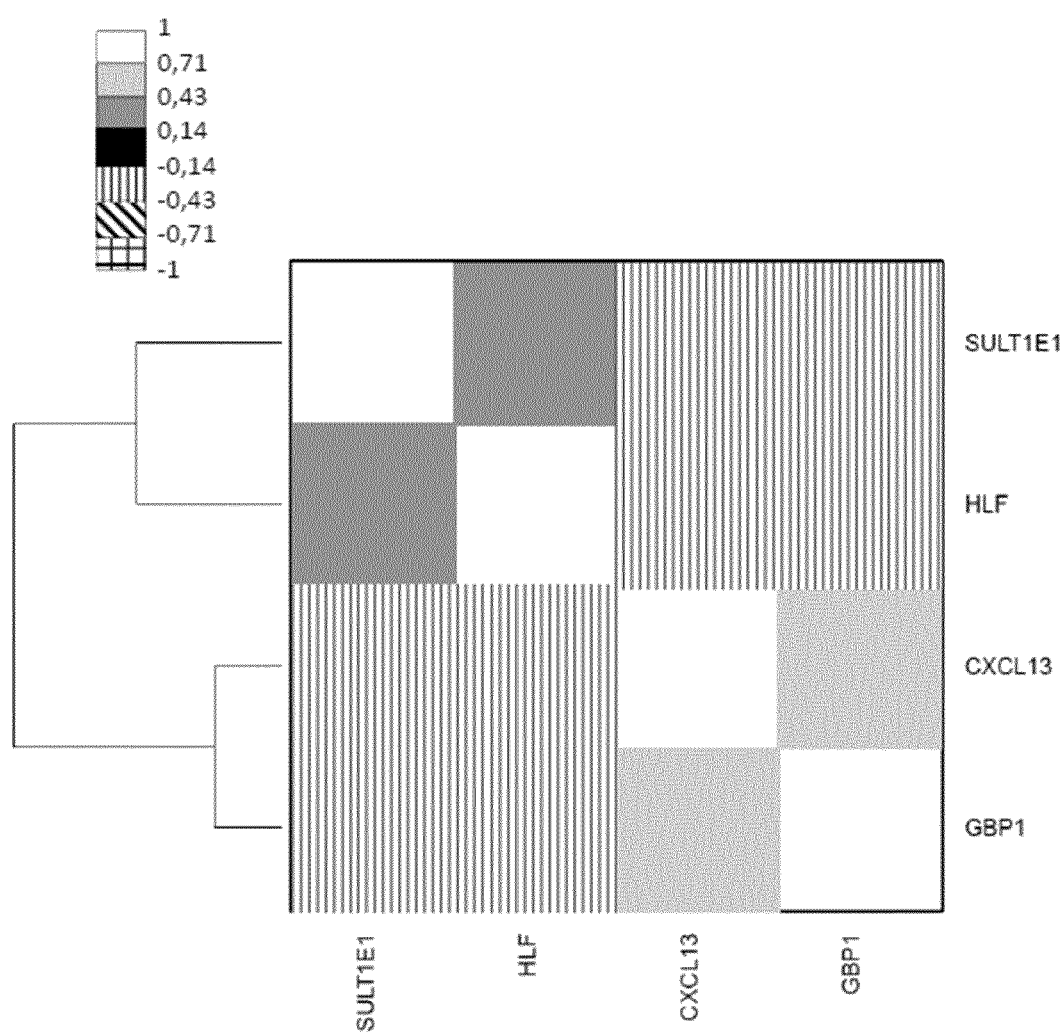

We performed pairwise correlation between the different genes included in the predictor using Spearman correlation. The correlation was assessed on 99 patients. Correlation coefficients values and 95% confidence intervals obtained using 1000 bootstrap repetitions are given in Table 11. Heat map shown in FIG. 21 reflects hierarchic clustering of pairwise correlation between the 4 genes. The cells are colored according to Spearman's correlation coefficient values with red indicating positive correlations and green indicating negative correlations.

TABLE 11

| Correlation coefficients and p-values of Spearman correlation | | | | |
|---|---|---|---|---|
| | SULT1E1 | HLF | CXCL13 | GBP1 |
| SULT1E1 | 1 | 0.19 [−0.02-0.38] | −0.28 [−0.46−−0.09] | −0.34 [−0.52−−0.12] |
| HLF | | 1 | −0.27 [−0.47−−0.06] | −0.20 [−0.42−−0.01] |
| CXCL13 | | | 1 | 0.62 [0.47-0.74] |
| GBP1 | | | | 1 |

3.2.5.5.2 Correlation Between the Genomic Predictor and Validated Gene Modules (Immune1 and Immune2)

Among 99 patients in the training dataset, only 85 had all genes expression to generate the genomic predictor and available immune1 and immune2 gene modules expressions [9]. We performed pairwise correlation using Spearman correlation. Correlation coefficients values and 95% confidence intervals obtained using 1000 bootstrap repetitions are given in Table 12.

TABLE 12

| Correlation between the genomic predictor and gene modules | | | |
|---|---|---|---|
| | Predictor | Immune1 | Immune2 |
| Predictor | 1 | 0.47 [0.25-0.63] | 0.64 [0.50-0.76] |
| Immune1 | | 1 | 0.43 [0.17-0.63] |
| Immune2 | | | 1 |

Figure 22:
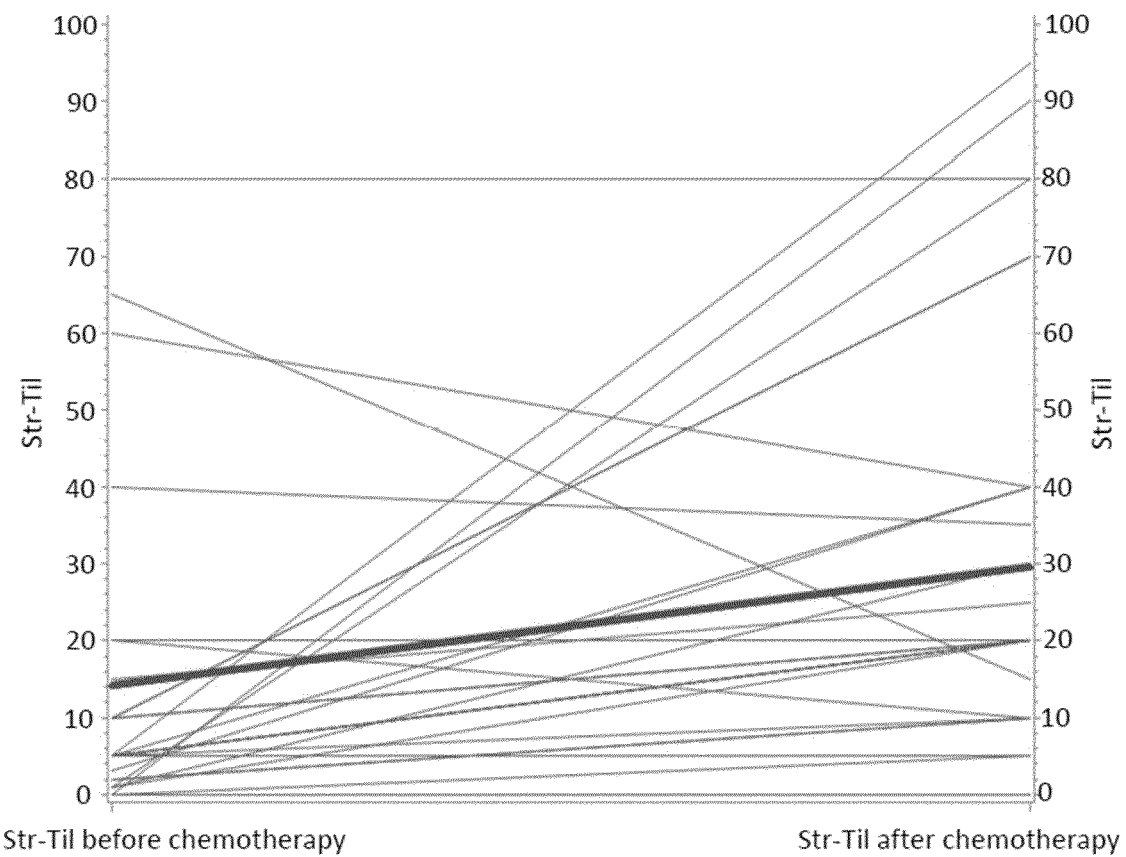

3.2.5.5.3 Change in Stromal TIL after Chemotherapy as Compared to Before Chemotherapy From TOP samples, 36 patients had a GEO accession and available value of stromal TIL before chemotherapy (34 from the training dataset +2 from the validation dataset). 29 of the 34 patients in the training dataset had both information about stromal TIL before chemotherapy and stromal TIL after chemotherapy. Spearman correlation coefficient value between stromal TIL before chemotherapy and stromal TIL after chemotherapy was 0.17 (p-value=0.384). There is a significant absolute increase in stromal TIL after chemotherapy as compared to before chemotherapy (18.28, [CI95% 6.21–30.34], paired t-test p-value=0.004). Individual profiles (Grey lines) and the mean profile (Dark grey line) are shown in FIG. 22.

3.2.5.5.4 Correlation Between the Genomic Predictor and Stromal TIL Before Chemotherapy From TOP samples, 22 had a GEO accession and available value of stromal TIL before chemotherapy. Spearman correlation coefficient value between stromal TIL before chemotherapy and the genomic predictor was 0.41 [−0.06–0.77]. 95% confidence intervals were obtained using 1000 bootstrap repetitions.

3.2.6 Prognostic Value of Stromal TIL after Chemotherapy on Survival

The Cox models are stratified on center. For illustrative purposes only, we show Kaplan-Meier survival curves, considering a cut-off value of 50% for stromal TIL.

3.2.6.1 Distant Relapse-Free Survival 3.2.6.1.1 Univariate Analysis

In the training dataset, 95 patients had available data. We observed 44 events. (Table 13).

TABLE 13

| | HR | 95% IC | P |
|---|---|---|---|
| Stromal TIL after chemotherapy | 0.98 | 0.96-1.00 | 0.023 |

3.2.6.1.2 Multivariate Analysis

In the training dataset, 94 patients had available data. We observed 43 events. Results of the Cox model are shown in Table 14.

TABLE 14

| Multivariate Cox model - Stromal TIL on distant relapse-free survival | | | |
|---|---|---|---|
| | HR | 95% IC | P |
| Age | 1.01 | 0.98-1.04 | 0.664 |
| cT | | | 0.312 |
| T0-1-2 | 1 | | |
| T3-4 | 1.39 | 0.74-2.61 | |
| cN | | | 0.816 |
| N0 | 1 | | |
| N+ | 1.09 | 0.54-2.17 | |
| Grade | | | 0.816 |
| 1-2 | 1 | | |
| 3 | 1.09 | 0.52-2.32 | |
| Stromal TIL after chemotherapy | 0.98 | 0.96-1.00 | 0.043 |

We used restricted cubic splines with 2 degrees of freedom to investigate the non-linear association between distant relapse-free survival and the stromal TIL after chemotherapy.

Figure 23:
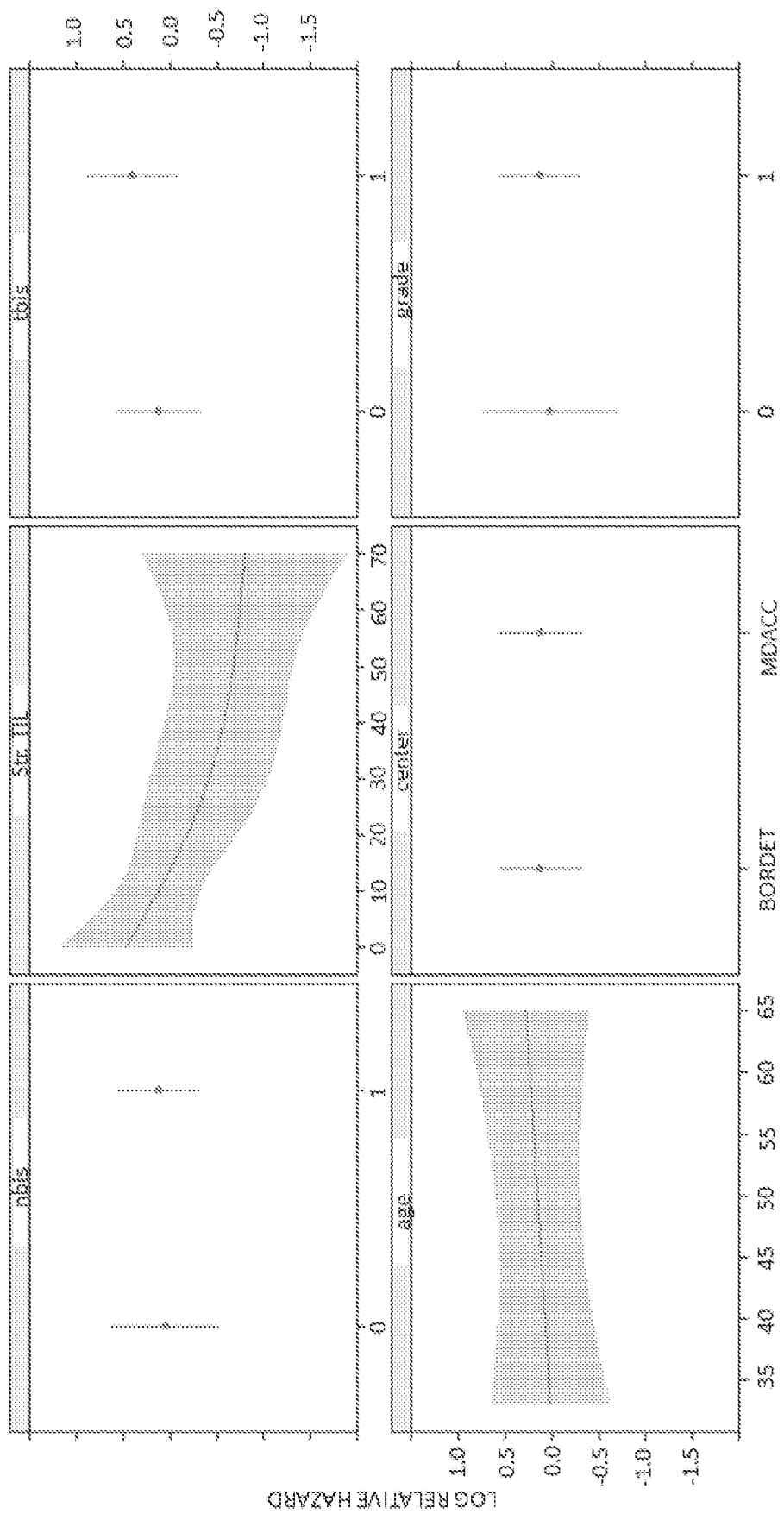

There was no significant non-linear effect (p=0.501). Log-relative hazard profiles are shown in FIG. 23.

3.2.6.2 Overall Survival 3.2.6.2.1 Univariate Analysis

In the training dataset, 95 patients had available data. We observed 42 events. (Table 15).

TABLE 15

| | HR | 95% IC | P |
|---|---|---|---|
| Stromal TIL after chemotherapy | 0.98 | 0.96-1.00 | 0.027 |

3.2.6.2.2 Multivariate Analysis

In the training dataset, 94 patients had available data. We observed 41 events. Results of the Cox model are shown in Table 16.

TABLE 16

Multivariate Cox model - Stromal TIL on overall survival

| | HR | 95% IC | P |
|---|---|---|---|
| Age | 1.02 | 0.99-1.05 | 0.317 |
| cT | | | 0.179 |
| T0-1-2 | 1 | | |
| T3-4 | 1.57 | 0.81-3.02 | |
| cN | | | 0.880 |
| N0 | 1 | | |
| N+ | 1.06 | 0.52-2.15 | |
| Grade | | | 0.859 |
| 1-2 | 1 | | |
| 3 | 0.93 | 0.44-1.97 | |
| Stromal TIL after chemotherapy | 0.98 | 0.96-1.00 | 0.063 |

Figure 25:
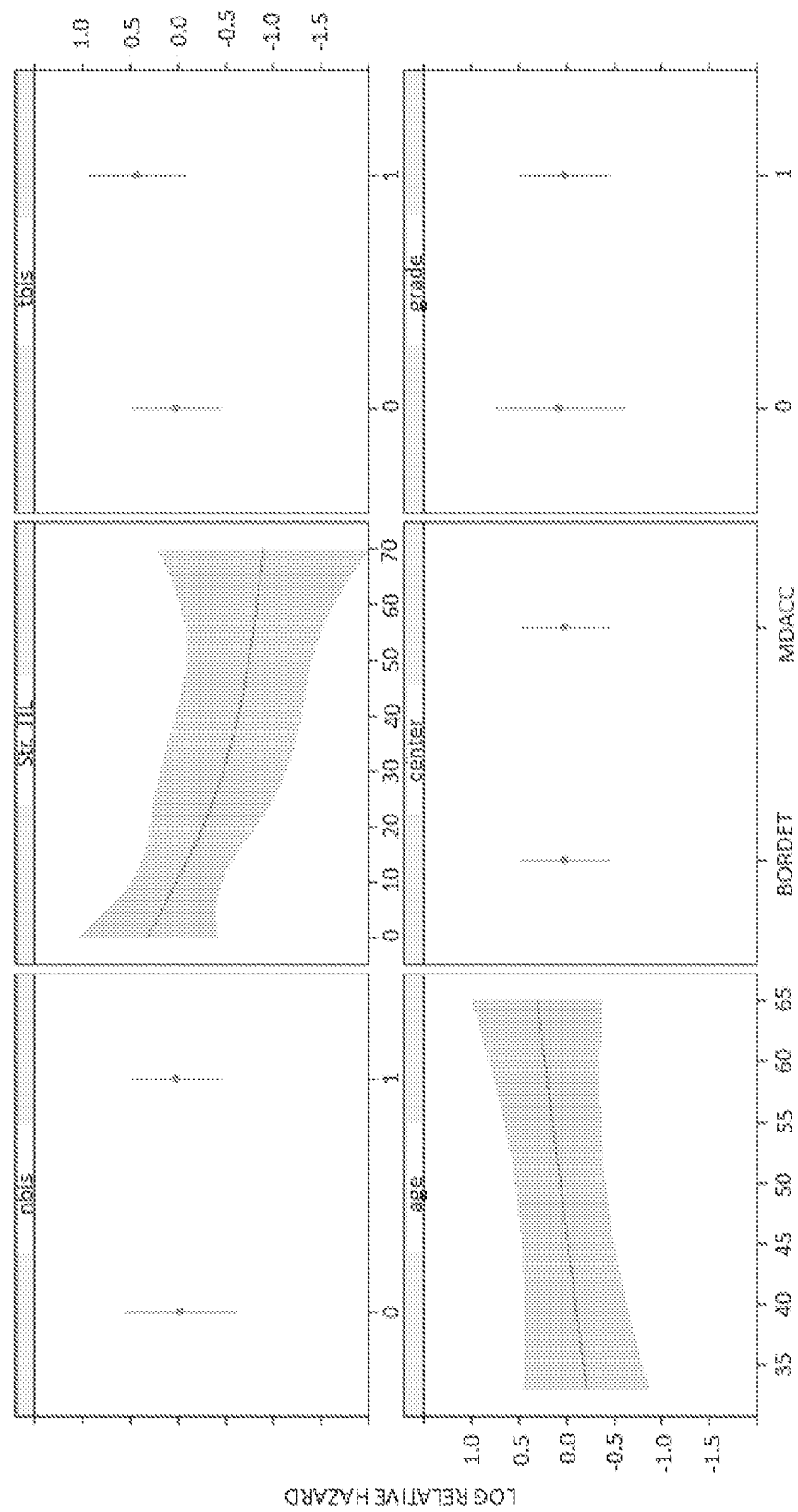

We used restricted cubic splines with 2 degrees of freedom to investigate the non-linear association between overall survival and stromal TIL after chemotherapy. There was no significant non-linear effect (p=0.594). Log-relative hazard profiles are shown in FIG. 25.

4 Validation Phase 4.1 Materiel 4.1.1 Description of the Validation Population

The participants' flow chart of the validation dataset is shown in FIG. 27.

In the validation dataset, 373 patients were TNBC (ER-, HER-). Among them, 185 had available survival data. The baseline characteristics of the patients in the validation dataset are presented Table 17.

TABLE 17

Baseline characteristics of patients in the validation dataset

| | I-SPY-1 n = 36 | LBJ/INEN/ GEICAM n = 21 | MAQCII/MDACC n = 55 | TOP n = 48 | USO-02103 n = 25 | All trials n = 185 |
|---|---|---|---|---|---|---|
| Age, years | | | | | | |
| Mean (SD) | 46 (8·2) | 51 (10·2) | 50 (10·9) | 47 (10·3) | 48 (10·5) | 48 (10·1) |
| Median (Q1-Q3) | 44 (40-53) | 46 (44-58) | 50 (42-57) | 48 (38-56) | 48 (40-55) | 48 (40-57) |
| Min-Max | 34-63 | 35-71 | 28-75 | 27-67 | 26-66 | 26-75 |
| cT | | | | | | |
| T1 | 0 (0%) | 0 (0%) | 9 (16%) | 8 (17%) | 1 (4%) | 18 (10%) |
| T2 | 17 (47%) | 6 (29%) | 26 (47%) | 31 (65%) | 10 (40%) | 90 (49%) |
| T3 | 16 (44%) | 8 (38%) | 7 (13%) | 1 (2%) | 14 (56%) | 46 (25%) |
| T4 | 3 (8%) | 7 (33%) | 13 (24%) | 8 (17%) | 0 (0%) | 31 (17%) |
| cN | | | | | | |
| N0 | 8 (22%) | 5 (24%) | 10 (18%) | 20 (42%) | 8 (32%) | 51 (28%) |
| N+ | 28 (78%) | 16 (76%) | 45 (82%) | 28 (58%) | 17 (68%) | 134 (72%) |
| ER status | | | | | | |
| Negative | 36 (100%) | 21 (100%) | 55 (100%) | 48 (100%) | 25 (100%) | 185 (100%) |
| Positive | 0 (0%) | 0 (0%) | 0 (0%) | 0 (0%) | 0 (0%) | 0 (0%) |
| PR status | | | | | | |
| Negative | 30 (91%) | 20 (95%) | 46 (84%) | 0 (0%) | 21 (84%) | 117 (87%) |
| Positive | 3 (9%) | 1 (5%) | 9 (16%) | 0 (0%) | 4 (16%) | 17 (13%) |
| Missing | 3 | 0 | 0 | 48 | 0 | 51 |
| HER2 status | | | | | | |
| Negative | 36 (100%) | 21 (100%) | 55 (100%) | 48 (100%) | 25 (100%) | 185 (100%) |
| Positive | 0 (0%) | 0 (0%) | 0 (0%) | 0 (0%) | 0 (0%) | 0 (0%) |
| Histologic grade | | | | | | |
| 1 | 0 (0%) | 2 (12%) | 0 (0%) | 2 (4%) | 0 (0%) | 4 (2%) |
| 2 | 3 (9%) | 3 (19%) | 5 (9%) | 6 (13%) | 3 (14%) | 20 (12%) |
| 3 | 21 (62%) | 11 (69%) | 50 (91%) | 37 (82%) | 19 (86%) | 138 (80%) |
| Unknown | 10 (29%) | 0 (0%) | 0 (0%) | 0 (0%) | 0 (0%) | 10 (6%) |
| Missing | 2 | 5 | 0 | 3 | 3 | 13 |
| Response | | | | | | |
| pCR | 10 (29%) | 5 (24%) | 35 (64%) | 7 (15%) | 11 (44%) | 68 (37%) |
| RD | 24 (71%) | 16 (76%) | 20 (36%) | 41 (85%) | 14 (56%) | 115 (63%) |
| Missing | 2 | 0 | 0 | 0 | 0 | 2 |
| No. of relapses | 12 (33%) | 10 (48%) | 15 (27%) | 12 (25%) | 8 (32%) | 57 (31%) |
| Median follow-up in years (Q1-Q3) | 2·53 (2·03-3·84) | 3·20 (3·13-3·70) | 2·60 (1·86-4·62) | 3·59 (2·57-4·73) | 4·12 (3·70-4·46) | 3·24 (2·26-4·46) |

TABLE 17-continued

Baseline characteristics of patients in the validation dataset

|  | I-SPY-1 n = 36 | LBJ/INEN/ GEICAM n = 21 | MAQCII/MDACC n = 55 | TOP n = 48 | USO-02103 n = 25 | All trials n = 185 |
| --- | --- | --- | --- | --- | --- | --- |
| GEO | GSE25066 | GSE25066 | GSE20194 GSE25066 | GSE16446 | GSE23988 GSE25066 |  |
| References | Hatzis et al[7] | Hatzis et al[7] | Shi et al[10] Hatzis et al[7] | Desmedt et al[8] | Hatzis et al[7] Iwamoto et al[11] |  |

Data are mean (SD), median (Q1-Q3), min-max, or n (%).
Patients of the validation set were from five different cohorts.
Patients included in the training set from MDACC neoadjuvant series and TOP study were excluded from the validation set.
SD, standard deviation;
Q1, 25th percentile;
Q3, 75th percentile;
Min, Minimum;
Max, Maximum;
cT, clinical tumor size;
cN, clinical nodal status;
ER, estrogen receptor;
PR, progesterone receptor;
HER2, human epidermal growth factor receptor 2;
pCR, pathological complete response;
RD, recurrent disease;
GEO, gene expression omnibus;
I-SPY-1, Investigation of Serial Studies to Predict Your Therapeutic Response With Imaging and Molecular Analysis;
LBJ, Lyndon B. Johnson hospital;
INEN, Instituto Nacional de Enfermedades Neoplasicas;
GEICAM, Grupo Espanol de Investigacion en Cancer de Mama;
MAQCII, MicroArray Quality Control Consortium II;
MDACC, MD Anderson Cancer Center;
TOP, Trial of Principle;
USO, US Oncology.

4.1.2 Genomic Data

The complete genomic data are available at the Gene Expression Omnibus (GEO, http://www.ncbi.nlm.nih.gov/geo/). We applied frozen robust multiarray analysis (fRMA) [McCall M N, Bolstad B M, Irizarry R A (2010) Frozen robust multiarray analysis (fRMA). Biostat Oxf Engl 11:242-253. doi: 10.1093/biostatistics/kxp059] preprocessing algorithm to normalize data separately on each series.

4.2 Methods and Results

4.2.1 Description of the Genomic Predictor

Figure 28:
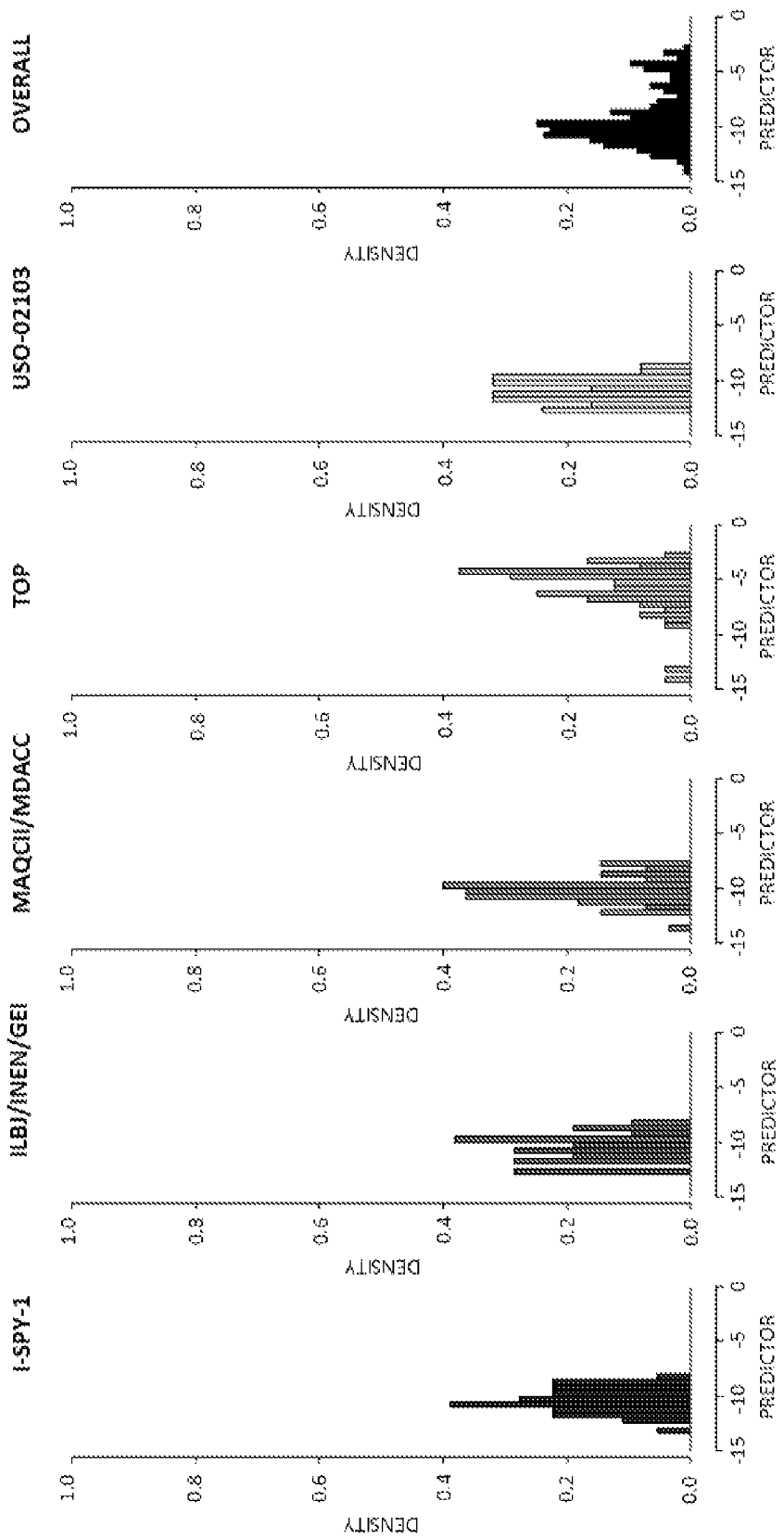

The genomic Predictor significantly deviates from normality (Shapiro-Wilk normality test pvalue=1.444e-08). There is a statistically significant difference in the genomic Predictor between the five cohorts' samples (Kruskal-Wallis rank sum test p-value <2.2e-16). Summary statistics of the genomic predictor in the validation dataset are given in Table 18. Histograms of the genomic predictor are shown in FIG. 28. TOP samples are different Affymetrix platform from all other samples (see Table 37).

TABLE 18

Summary statistics of the genomic predictor in the validation dataset

|  | I-SPY-1 N = 36 | LBJ/INEN/GEICAM N = 21 | MAQCII/MDACC N = 55 | TOP N = 48 | USO-02103 N = 25 | Overall N = 185 |
| --- | --- | --- | --- | --- | --- | --- |
| Mean | −10.38 | −10.64 | −10.20 | −5.72 | −10.98 | −9.23 |
| SD | 1.183 | 1.361 | 1.260 | 2.271 | 1.099 | 2.608 |
| Median | −10.48 | −10.74 | −10.24 | −5.07 | −11.23 | −9.95 |
| Q1-Q3 | −11.33--−9.49 | −11.54--−9.58 | −10.91--−9.59 | −6.55--−4.28 | −11.64--−10.05 | −10.98--−8.03 |
| IQR | 1.85 | 1.95 | 1.33 | 2.27 | 1.60 | 2.96 |
| Min-Max | −13.02--−8.03 | −12.90--−8.35 | −13.77--−7.74 | −14.30--−2.81 | −12.72--−8.96 | −14.30--−2.81 |

Figure 29:
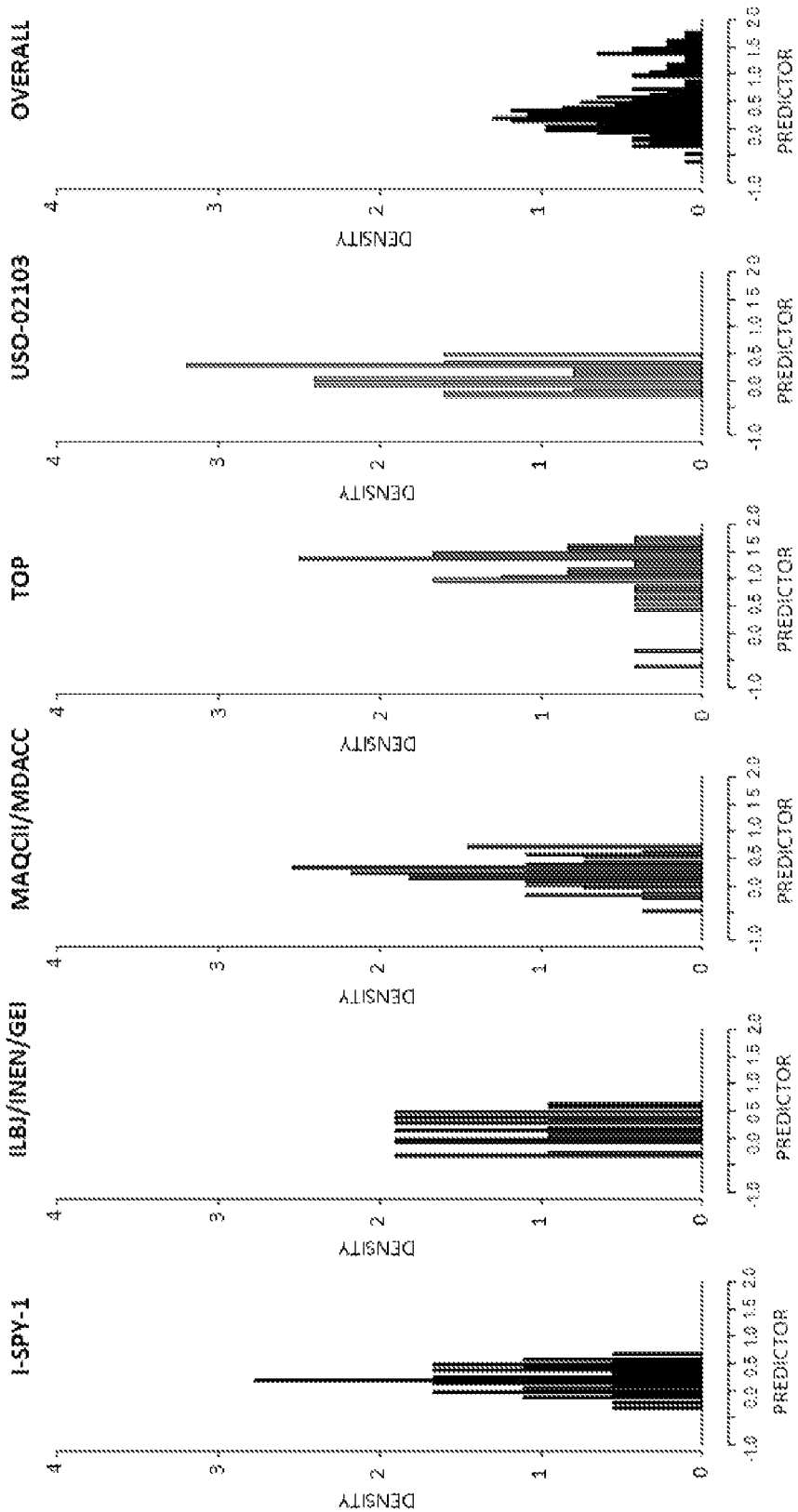

We performed the same transformation on the genomic predictor of the validation dataset as in the training dataset (see 3.2.5.2) using the 5% quantile of the genomic predictor in the training samples (99 patients, $Q_{0.05}=-11.35669$) and the 95% quantile of the genomic predictor in the training samples (99 patients, $Q_{0.95}=-6.511546$). Summary statistics of the transformed genomic predictor in the training dataset are given in Table 19. Histograms of the transformed genomic predictor are shown in FIG. 29.

TABLE 19

Summary statistics of the transformed genomic predictor in the validation dataset

|         | I-SPY-1<br>N = 36 | LBJ/INEN/GEICAM<br>N = 21 | MAQCII/MDACC<br>N = 55 | TOP<br>N = 48 | USO-02103<br>N = 25 | Overall<br>N = 185 |
|---|---|---|---|---|---|---|
| Mean    | 0.20       | 0.15        | 0.24       | 1.16      | 0.08        | 0.44      |
| SD      | 0.244      | 0.281       | 0.260      | 0.469     | 0.227       | 0.538     |
| Median  | 0.18       | 0.13        | 0.23       | 1.30      | 0.03        | 0.29      |
| Q1-Q3   | 0.00-0.39  | −0.04-0.37  | 0.09-0.36  | 0.99-1.46 | −0.06-0.27  | 0.08-0.69 |
| IQR     | 0.38       | 0.40        | 0.27       | 0.47      | 0.33        | 0.61      |
| Min-Max | −0.34-0.69 | −0.32-0.62  | −0.50-0.75 | −0.61-1.76| −0.28-0.49  | −0.61-176 |

We Used the Transformed Value of the Genomic Predictor within the Rest of the Validation Phase, Referring to it as Genomic Predictor.

4.2.2 Validation of the Prognostic Value of the Genomic Predictor on Distant Relapse-Free Survival The median follow-up (years) in the validation dataset was computed using inverse Kaplan-Meier method applied on distant relapse-free survival. There is no statistically significant difference in follow-up between the five cohorts (Logrank p-value=0.556). (Table 20).

TABLE 20

| Follow-up in years | I-SPY-1<br>N = 36 | LBJ/INEN/GEICAM<br>N = 21 | MAQCII/MDACC<br>N = 55 | TOP<br>N = 48 | USO-02103<br>N = 25 | Overall<br>N = 185 |
|---|---|---|---|---|---|---|
| Median | 2.53      | 3.20      | 2.60      | 3.59      | 4.12      | 3.24      |
| Q1-Q3  | 2.03-3.84 | 3.13-3.70 | 1.86-4.62 | 2.57-4.73 | 3.70-4.46 | 2.26-4.46 |

In the validation dataset, data were available only on distant relapse-free survival. 185 patients had available data. We observed 57 events. The Cox model is stratified on center.

4.2.2.1 Patients with No pCR (RD)

4.2.2.1.1 Univariate Analysis 115 patients were not in pCR. We observed 49 events among them. (Table 21).

TABLE 21

|                   | HR   | 95% IC    | P      |
|---|---|---|---|
| Genomic predictor | 0.36 | 0.18-0.75 | 0.0057 |

4.2.2.1.2 Multivariate Analysis 98 patients were not in pCR and had complete data. We observed 39 events among them. Results of the Cox model are shown in Table 22.

TABLE 22

Multivariate Cox model - Genomic Predictor on distant relapse-free survival - Validation dataset - Prognostic value of the four-gene signature on survival in a multivariate Cox model

|       | Training set - DRFS<br>(n = 94) | | | Validation set - DRFS<br>(n = 160) | | | Training set - OS<br>(n = 94) | | |
|---|---|---|---|---|---|---|---|---|---|
|       | HR   | 95% CI    | p     | HR   | 95% CI    | p     | HR   | 95% CI    | p     |
| Age   | 1.01 | 0.98-1.03 | 0.695 | 1.00 | 0.97-1.03 | 0.880 | 1.02 | 0.99-1.05 | 0.281 |
| cT    |      |           | 0.310 |      |           | 0.001 |      |           | 0.203 |
| T0-1-2| 1    |           |       | 1    |           |       | 1    |           |       |
| T3-4  | 1.39 | 0.74-2.62 |       | 2.96 | 1.54-6.67 |       | 1.54 | 0.79-2.97 |       |
| cN    |      |           | 0.559 |      |           | 0.011 |      |           | 0.554 |
| N0    | 1    |           |       | 1    |           |       | 1    |           |       |
| N+    | 1.23 | 0.61-2.47 |       | 3.19 | 1.30-7.83 |       | 1.24 | 0.61-2.54 |       |
| Grade |      |           | 0.100 |      |           | 0.981 |      |           | 0.503 |
| 1-2   | 1    |           |       | 1    |           |       | 1    |           |       |

TABLE 22-continued

Multivariate Cox model - Genomic Predictor on distant relapse-free survival - Validation dataset - Prognostic value of the four-gene signature on survival in a multivariate Cox model

|  | Training set - DRFS (n = 94) | | | Validation set - DRFS (n = 160) | | | Training set - OS (n = 94) | | |
| --- | --- | --- | --- | --- | --- | --- | --- | --- | --- |
|  | HR | 95% CI | p | HR | 95% CI | p | HR | 95% CI | p |
| 3 | 1.00 | 0.48-2.10 |  | 1.01 | 0.43-2.37 |  | 0.78 | 0.38-1.61 |  |
| 1-unit increase in the four-gene signature | 0.28 | 0.13-0.63 | 0.002 | 0.29 | 0.13-0.67 | 0.004 | 0.35 | 0.16-0.75 | 0.007 |

Figure 30:
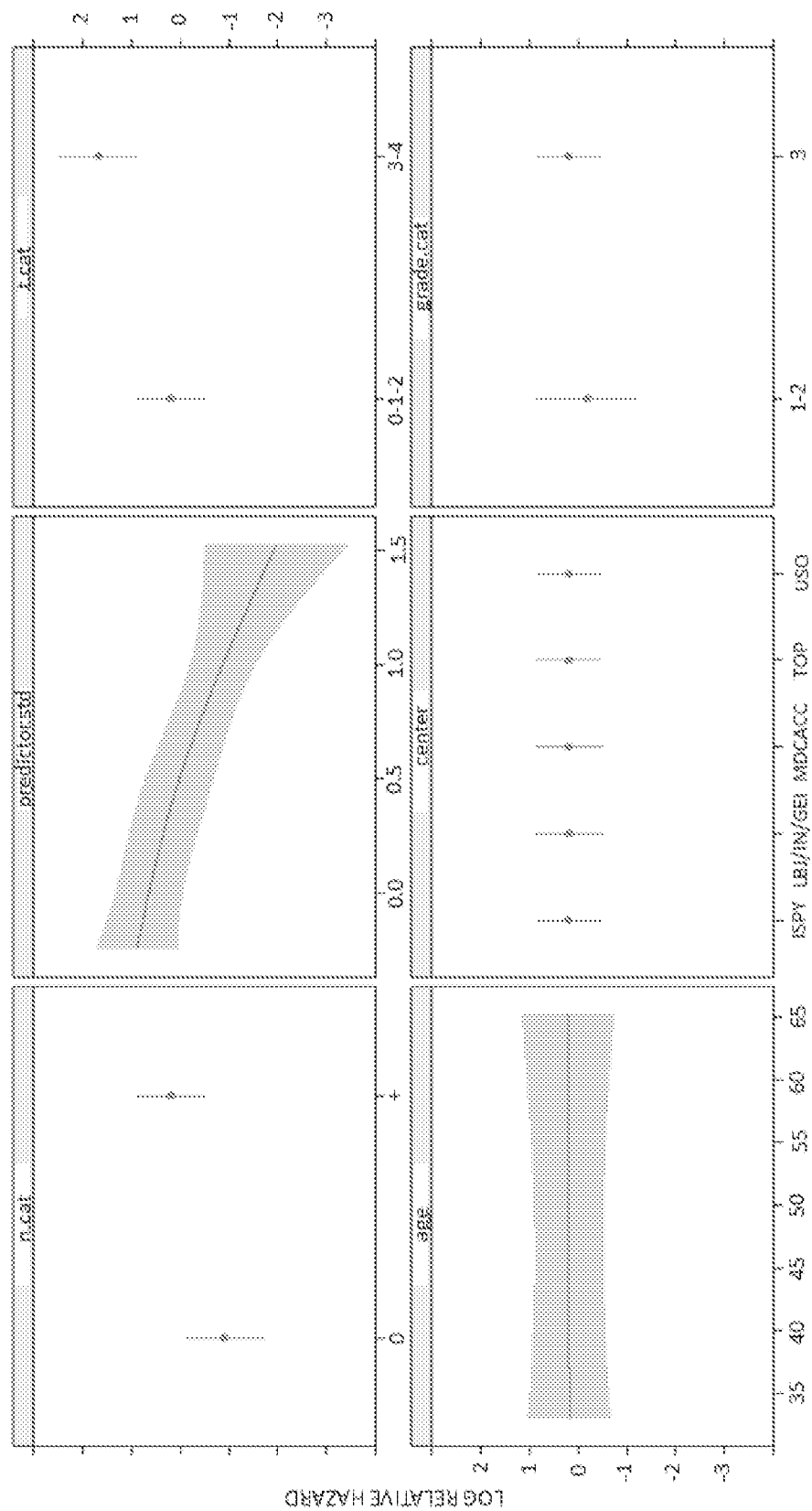

DRFS, distant relapse-free survival;
OS, overall survival;
cT, clinical tumor size;
cN, clinical nodal status;
HR, Hazard ratio;
CI, confidence interval;
P, p-value We used restricted cubic splines with 2 degrees of freedom to investigate the non-linear association between distant relapse-free survival and the genomic predictor in the validation dataset for patients achieving pCR. There was no significant non-linear effect (p=0.5240). Log-relative hazard profiles are shown in FIG. 30.

4.2.2.2 All patients (pCR and RD)
4.2.2.2.1 Univariate Analysis 185 patients had available data. We observed 57 events among them. (Table 23).

TABLE 23

|  | HR | 95% IC | P |
| --- | --- | --- | --- |
| Predictor | 0.36 | 0.18-0.74 | 0.0055 |

4.2.2.2.2 Multivariate Analysis 160 patients had complete data. We observed 45 events among them. Results of the Cox model are shown in Table 24.

Figure 31:

We used restricted cubic splines with 2 degrees of freedom to investigate the non-linear association between distant relapse-free survival and the genomic predictor in the validation dataset. There was no significant non-linear effect (p=0.4504). Log-relative hazard profiles are shown in FIG. 31.

4.2.3 Validation of Risk Groups

We used cut-off points assessed on the training dataset for building risk groups in the validation dataset (TER, MED, COX).

4.2.3.1 Patients with No pCR (RD)

Figure 32:
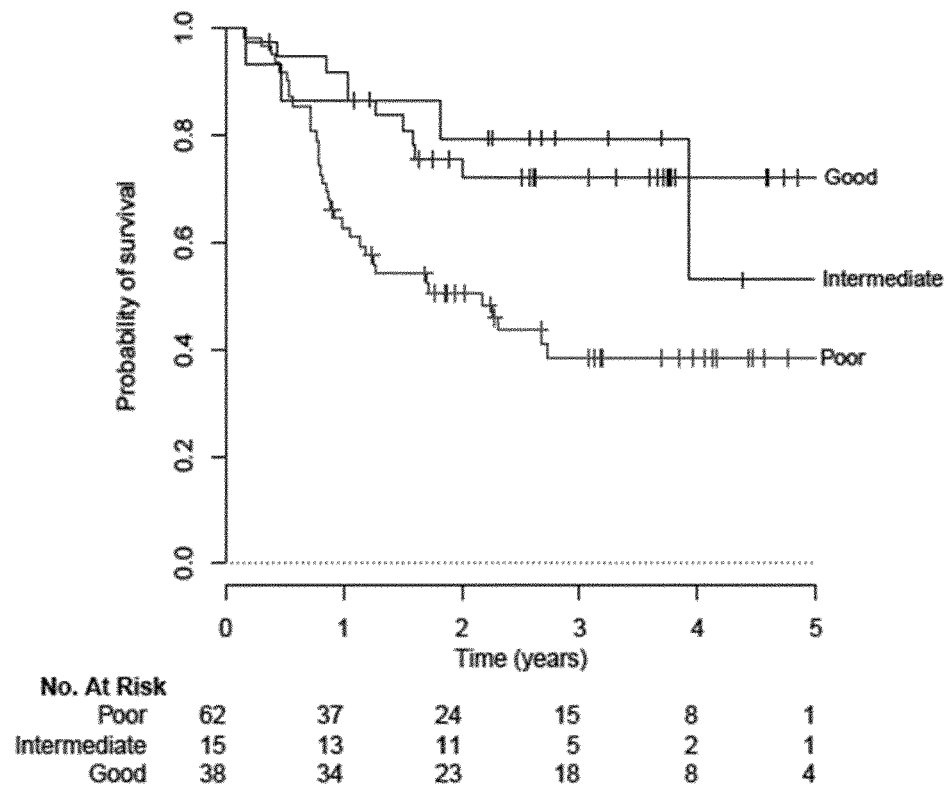
Figure 33:
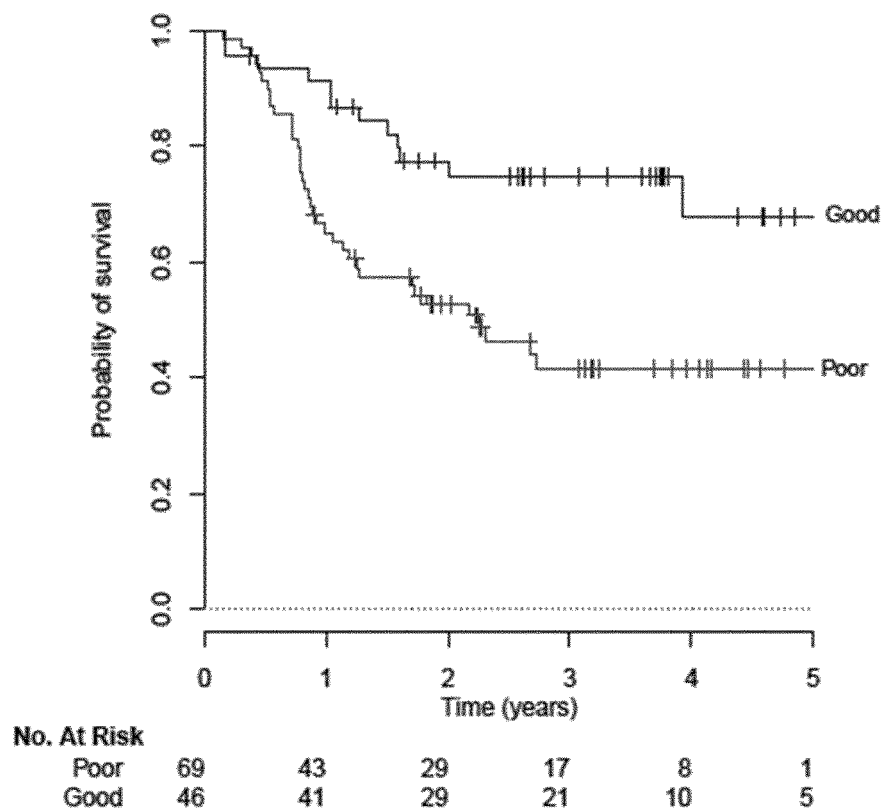
Figure 34:
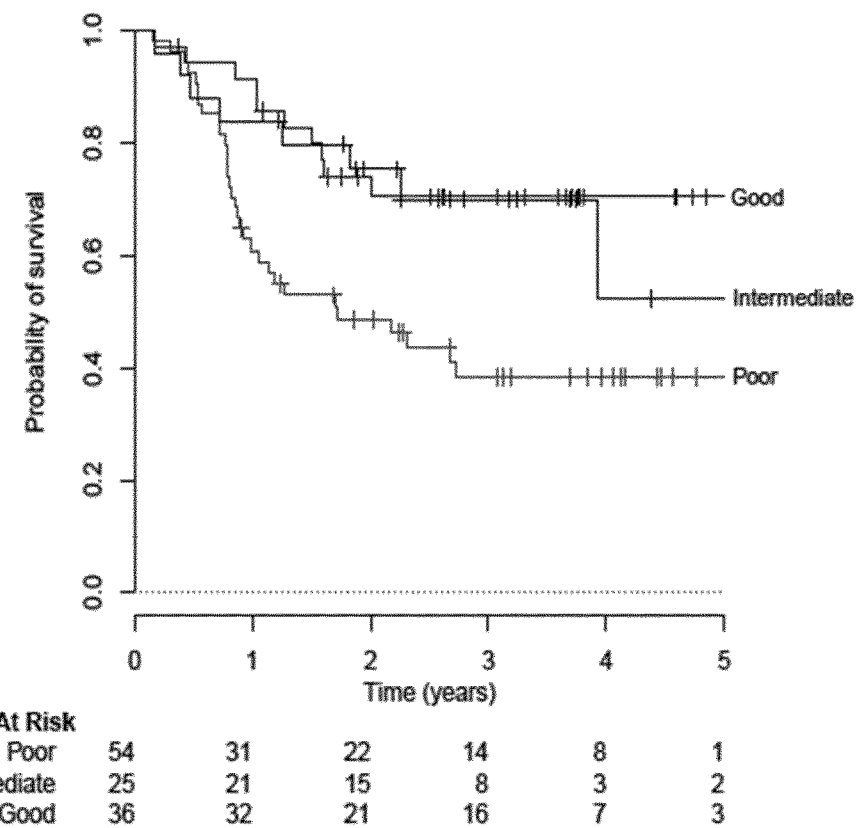

Kaplan-Meier distant relapse-free survival curves of the three risk groups according to the different cut-offs and for patients that did not achieved pCR are shown in FIG. 32, FIG. 33 and FIG. 34.

4.2.3.2 All patients (pCR and RD)

Figure 35:
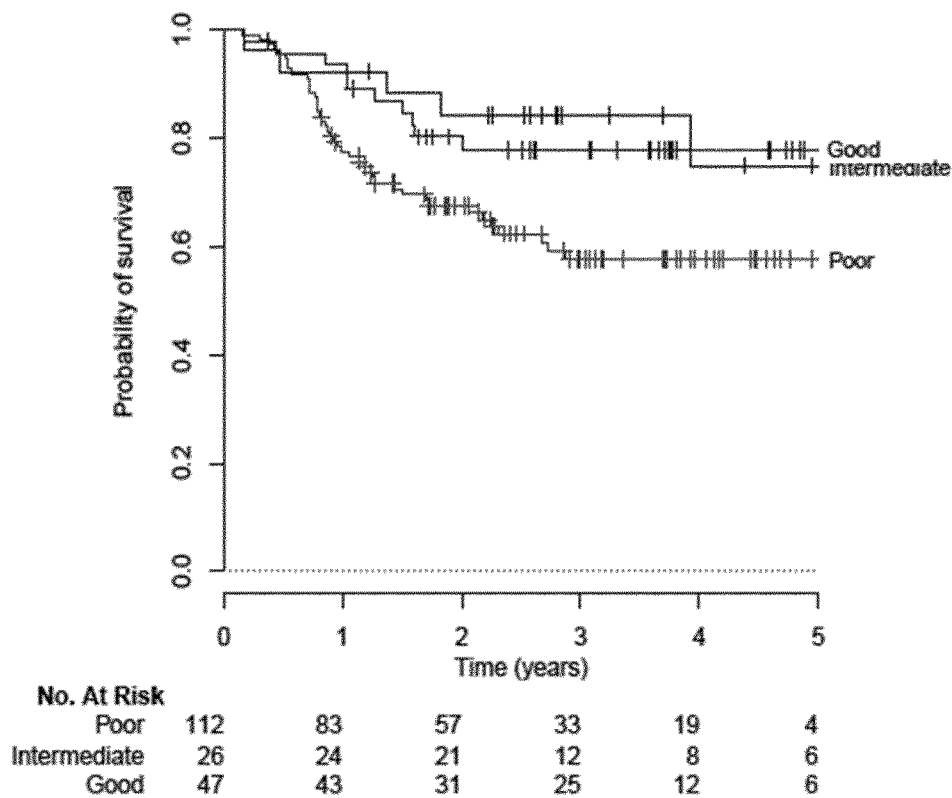
Figure 36:
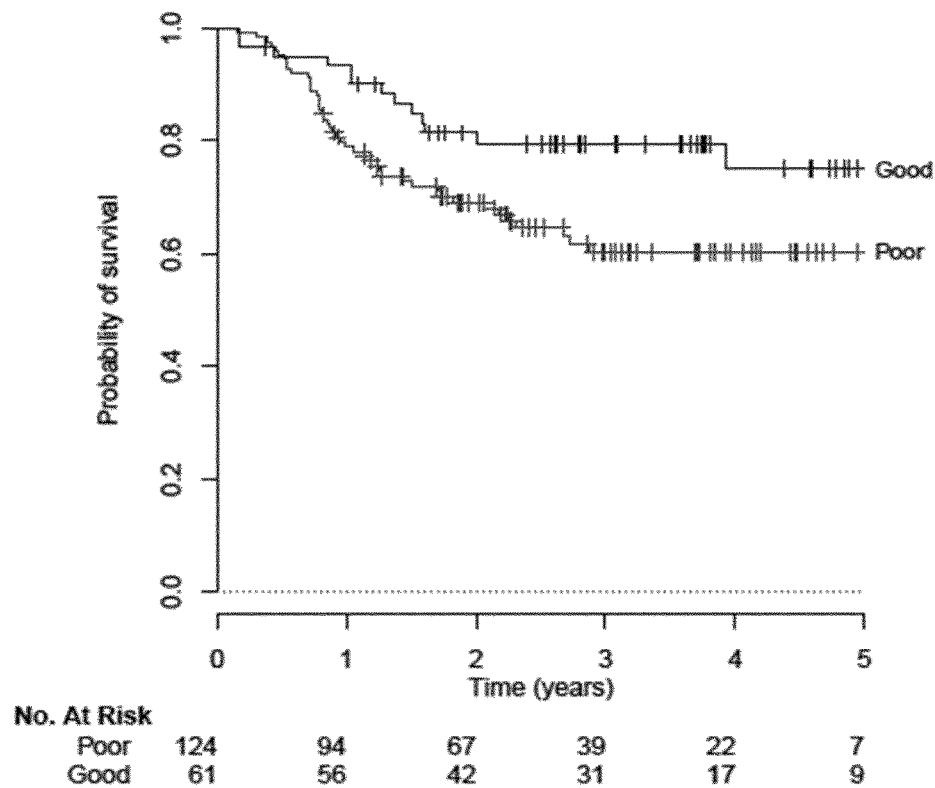
Figure 37:
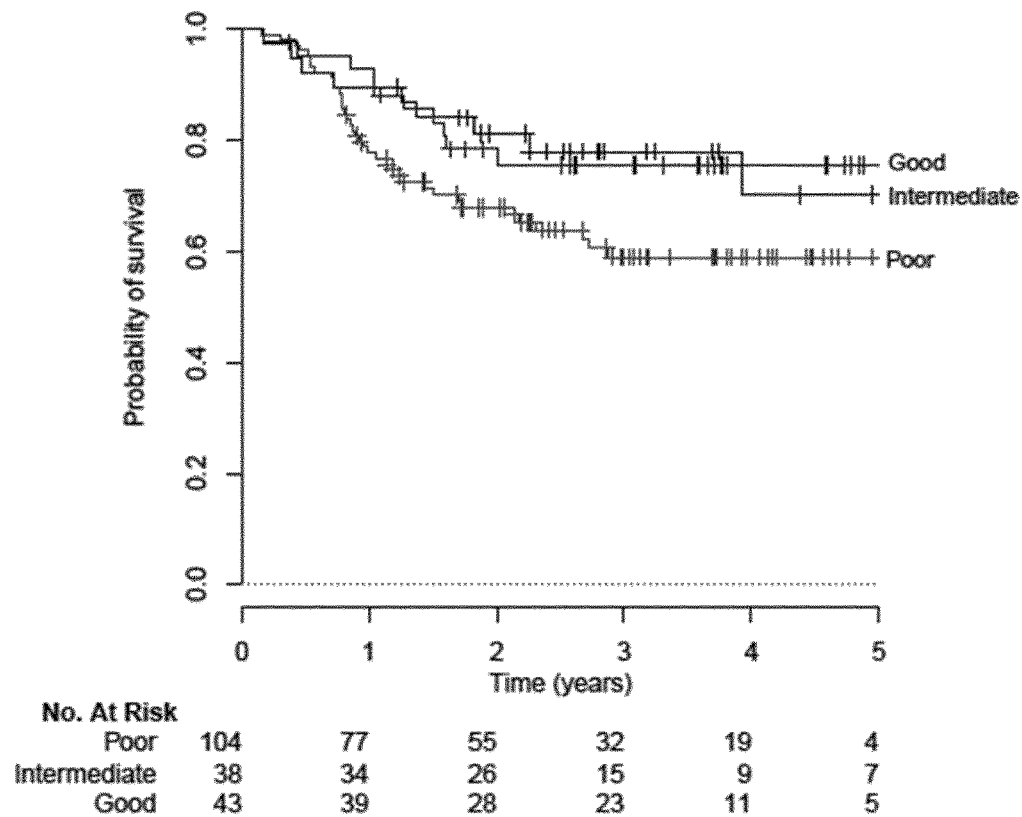

Kaplan-Meier distant relapse-free survival curves of the three risk groups according to the different cut-offs and for all patients are shown in FIG. 35, FIG. 36 and FIG. 37.

TABLE 24

Multivariate Cox model - Genomic Predictor on distant relapse-free survival - Validation Dataset - Prognostic value of the four-gene signature on survival in a multivariate Cox model

|  | Training set - DRFS (n = 94) | | | Validation set - DRFS (n = 160) | | | Training set - OS (n = 94) | | |
| --- | --- | --- | --- | --- | --- | --- | --- | --- | --- |
|  | HR | 95% CI | p | HR | 95% CI | p | HR | 95% CI | p |
| Age | 1.01 | 0.98-1.03 | 0.695 | 1.00 | 0.97-1.03 | 0.880 | 1.02 | 0.99-1.05 | 0.281 |
| cT |  |  | 0.310 |  |  | 0.001 |  |  | 0.203 |
| T0-1-2 | 1 |  |  | 1 |  |  | 1 |  |  |
| T3-4 | 1.39 | 0.74-2.62 |  | 2.96 | 1.54-6.67 |  | 1.54 | 0.79-2.97 |  |
| cN |  |  | 0.559 |  |  | 0.011 |  |  | 0.554 |
| N0 | 1 |  |  | 1 |  |  | 1 |  |  |
| N+ | 1.23 | 0.61-2.47 |  | 3.19 | 1.30-7.83 |  | 1.24 | 0.61-2.54 |  |
| Grade |  |  | 0.100 |  |  | 0.981 |  |  | 0.503 |
| 1-2 | 1 |  |  | 1 |  |  | 1 |  |  |
| 3 | 1.00 | 0.48-2.10 |  | 1.01 | 0.43-2.37 |  | 0.78 | 0.38-1.61 |  |
| 1-unit increase in the four-gene signature | 0.28 | 0.13-0.63 | 0.002 | 0.29 | 0.13-0.67 | 0.004 | 0.35 | 0.16-0.75 | 0.007 |

DRFS, distant relapse-free survival;
OS, overall survival;
cT, clinical tumor size;
cN, clinical nodal status;
HR, Hazard ratio;
CI, confidence interval;
P, p-value

4.2.4 Testing for Correlation
4.2.4.1 Gene—Gene Correlation

Figure 38:
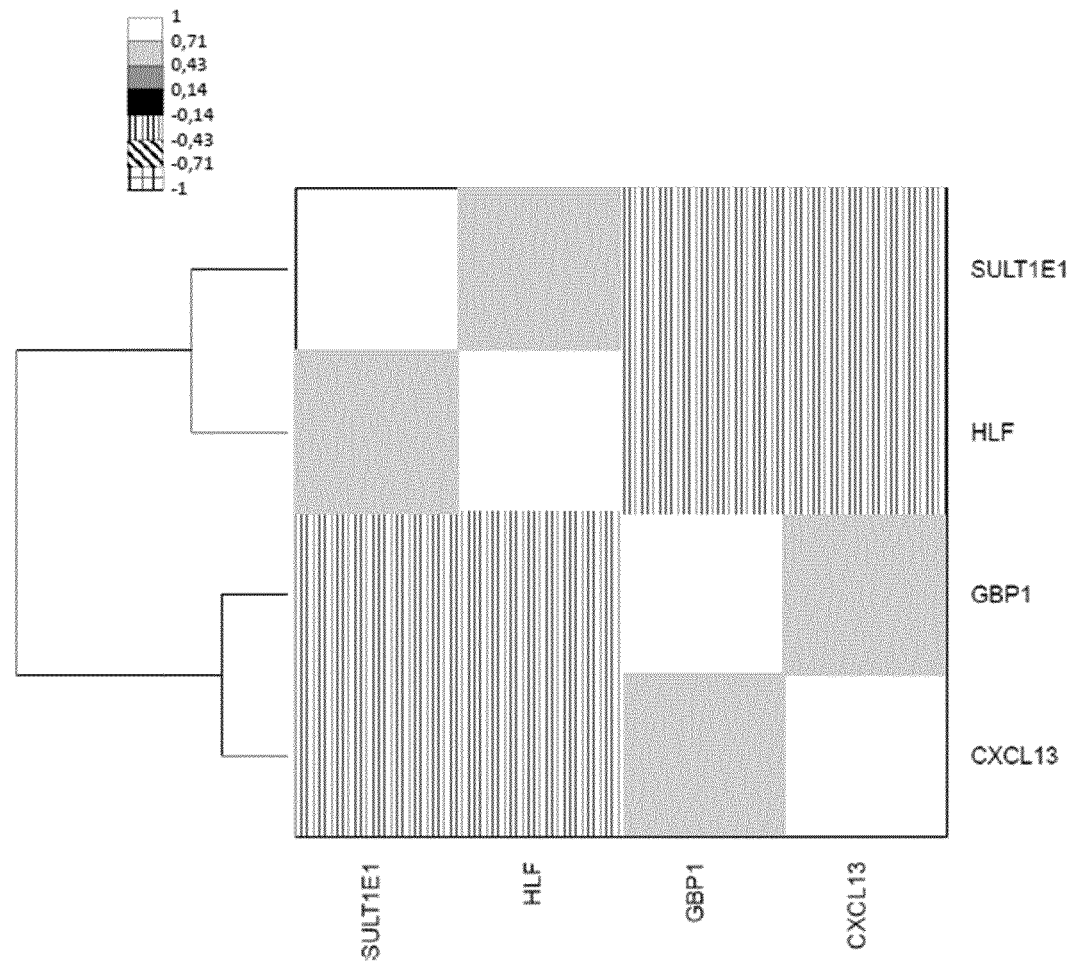

We performed pairwise correlation between the different genes included in the predictor using Spearman correlation. The correlation was assessed on 185 patients. Correlation coefficients values and 95% confidence intervals obtained using 1000 bootstrap repetitions are given in Table 25. Heat map shown in FIG. 38 reflects hierarchic clustering of pairwise correlation between the 4 genes. The cells are colored according to Spearman's correlation coefficient values with red indicating positive correlations and green indicating negative correlations.

TABLE 25

Correlation coefficients and p-values of Spearman correlation - Validation dataset

|        | SULT1E1 | HLF              | CXCL13             | GBP1               |
|--------|---------|------------------|--------------------|--------------------|
| SULT1E1| 1       | 0.47 [0.32-0.60] | −0.30 [−0.44−−0.17]| −0.37 [−0.49−−0.23]|
| HLF    |         | 1                | −0.16 [−0.30−−0.02]| −0.16 [−0.30−−0.02]|
| CXCL13 |         |                  | 1                  | 0.62 [0.50-0.71]   |
| GBP1   |         |                  |                    | 1                  |

4.2.4.2 Correlation Between Our Predictor and Validated Gene Modules (Immune1 and Immune2)

All patients (n=185) have expressions of the genomic predictor and available immune1 and immune2 gene modules expressions. We performed pairwise correlation using Spearman correlation. Correlation coefficients values and 95% confidence intervals obtained using 1000 bootstrap repetitions are given in Table 26.

TABLE 26

Correlation between the genomic predictor and gene modules - Validation dataset

|           | Predictor | Immune1          | Immune2          |
|-----------|-----------|------------------|------------------|
| Predictor | 1         | 0.52 [0.39-0.63] | 0.46 [0.34-0.59] |
| Immune1   |           | 1                | 0.62 [0.52-0.71] |
| Immune2   |           |                  | 1                |

4.2.6 Validation of the Prognostic Value in the Training and in the Validation Set at Diagnosis
4.2.6.1 Study Population Study flowchart for the training set is described in FIG. 1b. Overall, 99 patients with ER-/HER2- BC were selected to generate the signature. Patients' characteristics in the training set are given in Table 1. Flowchart for the validation set is described in supplementary material. Overall, 185 patients with ER-/HER2- BC were selected to validate the prognostic value of the signature on DRFS. Patients' characteristics in the validation set are given in Table 17.

4.2.6.2 Prognostic Value of the Four-Gene Signature in the Training Set

The prognostic value of the four-gene signature was assessed in 94 patients from the training set, for whom survival data were available. All patients had RD after NACT. Median (Q1-Q3) follow-up was 7.6 years (3.7-8.8). In a multivariate analysis (Table 42), the four-gene signature was significantly associated with better DRFS (HR for a one-unit increase in the value of the 4-gene signature: 0.28, 95% CI: 0.13-0.63, p=0-002). Kaplan-Meier DRFS curves of the risk groups (low four-gene signature vs. high four-gene signature) constructed using the median value of the 4-gene signature (median=0.51) are shown in FIG. 16. There was no evidence of a non-linear association between the 4-gene signature and DRFS. The 4-gene signature added significant prognostic information to the clinicopathological characteristics at diagnosis, as shown by the likelihood ratio test (p=0.004). The discrimination was also improved; at five years, the C-index increased from 0.617 to 0.673 (Table 42). Similar results were obtained for OS (HR for a one-unit increase in the value of the 4-gene signature: 0.35, 95% CI: 0.16-0.75, p=0-007; likelihood ratio test, p=0-012; the C-index increased from 0.631 to 0.668).

4.2.6.3 Prognostic Value of the Four-Gene Signature in the Validation Set

In the validation set, 68 (37%) patients achieved pCR and 115 (63%) relapsed (2 missing information on pCR). The prognostic value of the four-gene signature was assessed in 162 patients (23 missing information on grade). Median (Q1-Q3) follow-up was 3.2 years (2.3-4.5). In a multivariate analysis (Table 42), the four-gene signature was significantly associated with better DRFS (HR for a one-unit increase in the value of the 4-gene signature: 0.29, 95% CI: 0.13-0.67, p=0.004). Kaplan-Meier DRFS curves of the risk groups constructed using the same cutoff (0.51) as in the training set are shown in FIG. 36. There was no strong evidence of a non-linear association between the 4-gene signature and DRFS. The 4-gene signature added prognostic information to the clinicopathologic model at diagnosis as shown by the likelihood ratio test (p=0.008). Discrimination was also improved; at five years, the C-index increased from 0.686 to 0.700 in the validation set.

Results of the conditional logistic model showed no statistically significant association between the four-gene signature and the probability to achieve pCR in the validation set (OR for a one-unit increase in the four-gene signature: 0.96, 95% CI: 0.30-3.08, p=0-947, detailed results are provided in the supplementary material.

TABLE 42

Prognostic value of the four-gene signature on survival in a multivariate Cox model

| | Training set - DRFS (n = 94) | | | Validation set - DRFS (n = 160) | | | Training set - OS (n = 94) | | |
|---|---|---|---|---|---|---|---|---|---|
| | HR | 95% CI | p | HR | 95% CI | p | HR | 95% CI | p |
| Age | 1.01 | 0.98-1.03 | 0.695 | 1.00 | 0.97-1.03 | 0.880 | 1.02 | 0.99-1.05 | 0.281 |
| cT | | | 0.310 | | | 0.001 | | | 0.203 |
| T0-1-2 | 1 | | | 1 | | | 1 | | |
| T3-4 | 1.39 | 0.74-2.62 | | 2.96 | 1.54-6.67 | | 1.54 | 0.79-2.97 | |
| cN | | | 0.559 | | | 0.011 | | | 0.554 |
| N0 | 1 | | | 1 | | | 1 | | |
| N+ | 1.23 | 0.61-2.47 | | 3.19 | 1.30-7.83 | | 1.24 | 0.61-2.54 | |
| Grade | | | 0.100 | | | 0.981 | | | 0.503 |
| 1-2 | 1 | | | 1 | | | 1 | | |
| 3 | 1.00 | 0.48-2.10 | | 1.01 | 0.43-2.37 | | 0.78 | 0.38-1.61 | |
| 1-unit increase in the four-gene signature | 0.28 | 0.13-0.63 | 0.002 | 0.29 | 0.13-0.67 | 0.004 | 0.35 | 0.16-0.75 | 0.007 |

Figure 39:
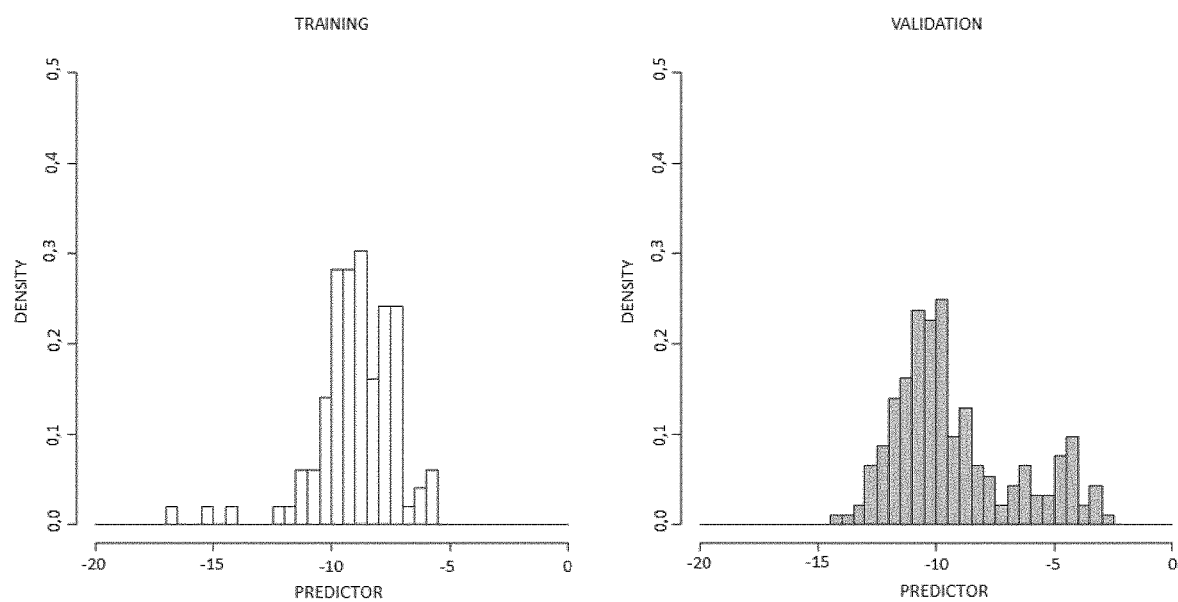

DRFS, distant relapse-free survival;
OS, overall survival;
cT, clinical tumor size;
cN, clinical nodal status;
HR, Hazard ratio;
CI, confidence interval;
P, p-value 5. Distribution of the Genomic Predictor: Training Vs. Validation Samples included 99 patients from the training dataset and 185 patients from the validation dataset. There was a statistically significant difference in the genomic predictor between the training dataset and the validation dataset (Wilcoxon rank sum test with continuity correction p-value=0.001349). Summary statistics of the genomic predictor are given in Table 27. Histograms of the genomic predictor are shown in FIG. 39.

TABLE 27

Summary statistics of the genomic predictor - Training vs. validation

| | Training N = 99 | validation N = 185 |
|---|---|---|
| Mean | −8.96 | −9.23 |
| SD | 1.766 | 2.608 |
| Median | −8.88 | −9.95 |
| Q1-Q3 | −9.77--7.73 | −10.98--8.03 |
| IQR | 2.03 | 2.96 |
| Min-Max | −16.75--5.82 | −14.30--2.81 |

Figure 40:
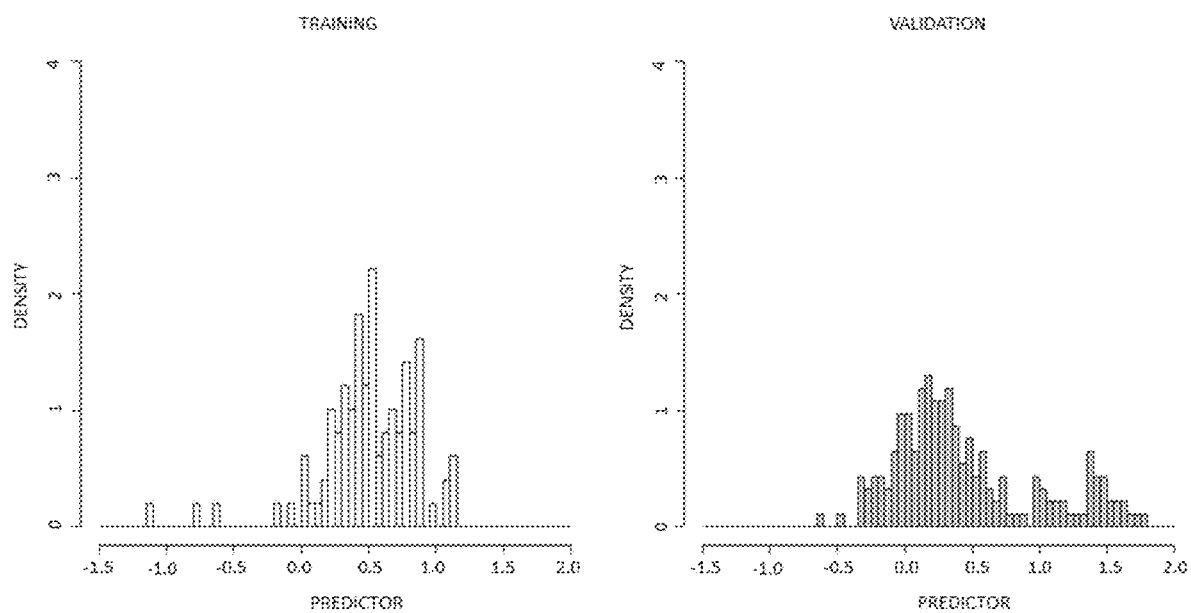

Summary statistics of the standardized genomic predictor are given in Table 28. Histograms of the genomic predictor are shown in FIG. 40.

TABLE 28

Summary statistics of the transformed genomic predictor - Training vs. validation

| | Training N = 99 | validation N = 185 |
|---|---|---|
| Mean | 0.49 | 0.44 |
| SD | 0.364 | 0.538 |
| Median | 0.51 | 0.29 |
| Q1-Q3 | 0.33-0.75 | 0.08-0.69 |
| IQR | 0.42 | 0.61 |
| Min-Max | −1.11-1.14 | −0.61-1.76 |

6. Evaluating the Added Value of the Genomic Predictor to a Clinical Model

We used Uno's C-statistic to quantify the capacity of the prediction models in discriminating among subjects with different event times [10]. We considered two truncation times: 3 years and 5 years. The resulting Cs tell how well the given prediction models work in predicting events that occur in the time range from 0 to 3 years and 0 to 5 years, respectively. The clinical models (CM) included data in Table 29.

TABLE 29

| | Age (continuous) | T (0-1-2 vs. 3-4) | N (0 vs. +) | Grade (1-2 vs. 3) | pCR Yes vs. RD |
|---|---|---|---|---|---|
| Training OS (n = 94) | ☑ | ☑ | ☑ | ☑ | ☒ |
| Training DRFS (n = 94) | ☑ | ☑ | ☑ | ☑ | ☒ |
| Validation DRFS no pCR (n = 98) | ☑ | ☑ | ☑ | ☑ | ☒ |
| Validation DRFS (n = 160) | ☑ | ☑ | ☑ | ☑ | ☑ |

We used the likelihood ratio statistics in Cox regression models stratified on center to estimate the added value of the genomic predictor to the previously defined clinical models. We gave p-values of the likelihood ratio test. Results of the assessment of added value of the genomic predictor are shown in Table 30a and b. 95% confidence intervals were obtained using 1000 bootstrap repetitions.

TABLE 30a

Assessment of added value of the genomic predictor

| | Clinical model (CM) | | CM + genomic predictor | | Difference | | | |
| --- | --- | --- | --- | --- | --- | --- | --- | --- |
| | 3-year C-index [95% CI] | 5-year C-index [95% CI] | 3-year C-index [95% CI] | 5-year C-index [95% CI] | 3-year C-index increase [95% CI] | 5-year C-index increase [95% CI] | $\chi^2$ increase | p |
| Training OS (n = 94) | 0.643 [0.504-0.783] | 0.631 [0.449-0.764] | 0.663 [0.544-0.782] | 0.668 [0.554-0.781] | 0.020 [−0.069-0.108] | 0.036 [−0.051-0.123] | 6.25 | 0.012 |
| Training DRFS (n = 94) | 0.657 [0.507-0.807] | 0.617 [0.488-0.745] | 0.681 [0.558-0.804] | 0.673 [0.566-0.779] | 0.024 [−0.082-0.130] | 0.056 [−0.051-0.163] | 8.23 | 0.004 |
| Validation DRFS no pCR (n = 98) | 0.699 [0.588-0.809] | 0.712 [0.601-0.823] | 0.725 [0.626-0.824] | 0.737 [0.637-0.838] | 0.027 [−0.025-0.078] | 0.025 [−0.023-0.073] | 9.66 | 0.002 |
| Validation DRFS (n = 160) | 0.754 [0.668-0.839] | 0.764 [0.680-0.849] | 0.772 [0.692-0.851] | 0.782 [0.702-0.861] | 0.018 [−0.012-0.048] | 0.017 [−0.011-0.045] | 9.01 | 0.003 |

TABLE 30b

Assessing the added prognostic value of the four-gene signature to a clinical model

| | CM | | CM + 4-gene signature | | Difference | | | |
| --- | --- | --- | --- | --- | --- | --- | --- | --- |
| | 3-year C-index [95% CI] | 5-year C-index [95% CI] | 3-year C-index [95% CI] | 5-year C-index [95% CI] | 3-year C-index increase [95% CI] | 5-year C-index increase [95% CI] | $\chi^2$ increase | p |
| Training DRFS (n = 94) | 0.657 [0.507-0.807] | 0.617 [0.488-0.745] | 0.681 [0.558-0.804] | 0.673 [0.566-0.779] | 0.024 [−0.082-0.130] | 0.056 [−0.051-0.163] | 8.23 | 0.004 |
| Validation DRFS (n = 160) | 0.681 [0.584-0.779] | 0.686 [0.592-0.780] | 0.693 [0.598-0.788] | 0.700 [0.606-0.795] | 0.012 [−0.033-0.058] | 0.014 [−0.028-0.056] | 7.1 | 0.008 |
| Training OS (n = 94) | 0.643 [0.504-0.783] | 0.631 [0.449-0.764] | 0.663 [0.544-0.782] | 0.668 [0.554-0.781] | 0.020 [−0.069-0.108] | 0.036 [−0.051-0.123] | 6.25 | 0.012 |

Uno's concordance indices were computed to quantify the capacity of the prediction models in discriminating among subjects with different event times. Two truncation times were considered: 3 years and 5 years. The concordance indices indicate how well the given prediction models work in predicting events that occur in the time range from 0 to 3 years and 0 to 5 years, respectively. The likelihood ratio statistics was used in Cox regression models stratified on series to estimate the added value of the 4-gene signature to the clinical models. 95% confidence intervals were obtained using 1000 bootstrap repetitions. CM, clinical model; C-index, Concordance index; p, p-value; DRFS, distant relapse-free survival; OS, overall survival

TABLE 31

Summary information about the neoadjuvant studies included in the present analysis.

| | EORTIC10994 | I-SPY-1 | LBJ/INEN/GEICAM | MDACC trial |
|---|---|---|---|---|
| Study design | Intergroup randomized multicentre phase 3 trial. | Investigation of Serial Studies to Predict Your Therapeutic Response with Imaging And moLecular Analysis or I-SPY 1: Multicenter trial. | Prospective Multicenter Trial. | Prospective randomized multicenter trial. |
| Inclusion criteria | http://clinicaltrials.gov/ct2/show/NCT00017095?term=EORTIC10994&rank=1 | [5] and http://clinicaltrials.gov/ct2/show/NCT00033397 | [5] | [6] |
| Objective | To assess whether the benefit of adding taxanes to anthracyclines is mainly restricted to the TP53-mutated breast tumors. | To identify predictors of pCR and survival in women with locally advanced breast cancers treated with chemotherapy. | NA | To interrogate whether patients with DLDA-30 - positive tumors (DLDA 30 is a genomic predictor of pCR) are significantly more likely to experience pCR to T/FAC. |
| Primary endpoint | Progression Free Survival | pCR | NA | pCR |
| Patients enrolled | 1856 | NA | NA | 273 |
| Patients with publicly available gene expression data | 160 | 79 | 57 | 178 |
| Chemotherapy Regimen | Randomly assigned to A. Fluorouracil 500 mg/m², epirubicin 100 mg/m², and cyclophosphamide 500 mg/m² q 3 weeks (FEC) X6 or fluorouracil 600 mg/m², epirubicin 75 mg/m², cyclophosphamide 900 mg/m² q 3 weeks (tailored FEC) X6 B. Docetaxel 100 mg/m² q 3 weeks X3 followed by epirubicin 90 mg/m² plus docetaxel 70 mg/m² q 3 weeks X3 (T-ET). | Doxorubicin and cyclophosphamide (AC) X4 followed by paclitaxel X4 (N = 60) or docetaxel X4 (N = 18) or taxane not specified (N = 5). | Docetaxel with capecitabine (TxX) X4 followed by fluorouracil, epirubicin and cyclophosphamide (FEC) X4 | Randomly assigned to A. Paclitaxel 80 mg/m2 q week x 12 followed by fluorouracil 500 mg/m2, doxorubicin 50 mg/m2 and cyclophosphamide 500 mg/m2 q 3 weeks X4 (T/FAC) and B FAC X6 (Epirubicin 100 mg/m2 could be substituted for doxorubicin at the discretion of investigators). |
| Pre-treatment biopsies | Core | Core | Core/FNA | FNA |
| Invasive Tumor Cell Content per biopsy | ≥20% | NA | NA | 70-90% pure neoplastic cells |
| Relapse Free Survival | Time from randomisation to locoregional progression/relapse, distant metastasis, death from any cause, or invasive contralateral breast cancer (Progression Free Survial). | Time from initial diagnosis to distant relapse or death. | Time from initial diagnosis to distant relapse or death. | NA |

TABLE 31-continued

Summary information about the neoadjuvant studies included in the present analysis.

| | EORTC10994 | I-SPY-1 | LBJ/INEN/GEICAM | MDACC trial |
|---|---|---|---|---|
| Microarray experiment | RNA was purified with Qiagen. RNeasy kit, RNA amplification & hybridization was performed according to standard Affymetrix protocols. Affymetrix U133_X3P. | RNA was extracted using Qiagen Rneasy Kit, RNA amplification & hybridization was performed according to standard Affymetrix protocols. Human Genome U133A Array. | RNA was extracted using Qiagen Rneasy Kit, RNA amplification & hybridization was performed according to standard Affymetrix protocols. Human Genome U133A Array. | RNA was extracted using Qiagen Rneasy Kit, RNA amplification & hybridization was performed according to standard Affymetrix protocols. Human Genome U133A Array. |
| Ref | 7,8 | 5,9,10 | 5 | 6 |
| Study design | TOP Prospective, multicenter study. | MAQCII/MDACC Prospective, multicenter study. 5,11,12 | MAQCIII Prospective, multicenter study. 5,12 | USO-02103 Phase II trial. 5,13 |
| Inclusion criteria | http://clinicaltrial.gov/ct2/show/NCT00162812?term=top+border&rank=1 | | | |
| Objective | To evaluate the predictive value of topoisomerase II-(TOP2A) and develop a gene expression signature to identify those patients who do not benefit from anthracyclines. | To assess the capabilities and limitations of various data analysis methods in developing and validating microarray-based predictive models. To reach consensus on the "best practices" for development and validation of predictive models based on microarray gene expression and genotyping data for personalized medicine. | To assess the technical performance of next-generation sequencing platforms by generating benchmark datasets with reference samples and evaluating advantages and limitations of various bioinformatics strategies in RNA and DNA analyses. | NA |
| Primary endpoint | pCR | NA | NA | NA |
| Patients enrolled | 149 | NA | NA | NA |
| Patients with publicly available gene expression data | 114 | 265 | 82 | 61 |
| Neoadjuvant Chemotherapy Regimen | Early Breast (N = 65): Epirubicin 100 mg/m2 q 3 weeks X4 Locally advanced/inflammatory (N = 49): Epirubicin 100 mg/m2 weeks X6. | Paclitaxel 80 mg/m2 q week X12 followed by fluorouracil 500 mg/m2, doxorubicin 50 mg/m2 and cyclophosphamide 500 mg/m2 q 3 weeks X4 (T/FAC). | Fluorouracil, epirubicin, and cyclophosphamide (FEC) q 3 weeks X4 or fluorouracil, doxorubicin and cyclophosphamide q 3 weeks X4 (FAC). | Fluorouracil 500 mg/m2, epirubicin 100 mg/m2, and cyclophosphamide 500 mg/m2, q 3 weeks, followed by docetaxel 35 mg/m2 q week X12. concomitant with capecitabine 850 mg/m2 twice daily for 14 days, q 3 weeks (FEC/wTX). |

TABLE 31-continued

Summary information about the neoadjuvant studies included in the present analysis.

| | EORTC10994 | I-SPY-1 | LBJ/INEN/GEICAM | MDACC trial |
|---|---|---|---|---|
| Dose intensity for each drug | NA | NA | NA | NA |
| Pre-treatment biopsies | Core | FNA | FNA | FNA |
| Invasive Tumor Cell Content per biopsy | >30% | 70-90% pure neoplastic cells | 70-90% pure neoplastic cells | 70-90% pure neoplastic cells |
| Relapse Free Survival | Time from diagnosis to distant metastasis, contralateral breast tumor or death. | Time from initial diagnosis to distant relapse or death. | NA | Time from initial diagnosis to distant relapse or death. |
| Microarray experimental setting | RNA isolation was performed using the Trizol method and RNA purification using RNeasy Kit, RNA. amplification and hybridization were done according to standard Affymetrix protocols. Human Genome U133-2.0 plus GeneChip. | RNA was extracted using Qiagen Rneasy Kit, RNA amplification & hybridization was performed according to standard Affymetrix protocols Human Genome U133A Array. | RNA was extracted using Qiagen Rneasy Kit, RNA amplification & hybridization was performed according to standard Affymetrix protocols. Human Genome U133A Array. | RNA was extracted using Qiagen Rneasy Kit, RNA amplification & hybridization was performed according to standard Affymetrix protocols. Human Genome U133A Array. |
| Ref | 14 | 5,11,12 | 5,12 | 5,13 |

TABLE 32

Baseline characteristics of patients in the training dataset

| Characteristics | N = 113 N (%) |
|---|---|
| Center | |
| Bordet (TOP) | 44 (39) |
| MDACC | 69 (61) |
| Demographics | |
| Age | |
| Mean | 49 |
| SD | 11.2 |
| Median | 48 |
| Q1-Q3 | 40-58 |
| Min-Max | 27-75 |
| Tumor information | |
| ER | |
| Positive | 0 (0) |
| Negative | 113 (100) |
| PgR | |
| Positive | 0 (0) |
| Negative | 95 (100) |
| Missing | 18 |
| HER2 | |
| Positive | 14 (12) |
| Negative | 99 (88) |
| cT | |
| T1 | 6 (5) |
| T2 | 72 (64) |
| T3 | 19 (17) |
| T4 | 16 (14) |
| cT | |
| T0-1-2 | 78 (69) |
| T3-4 | 35 (31) |
| cN | |
| N0 | 39 (35) |
| N1 | 49 (43) |
| N2 | 13 (12) |
| N3 | 12 (11) |
| cN | |
| N0 | 39 (35) |
| N+ | 74 (65) |
| Grade | |
| 2 | 20 (18) |
| 3 | 92 (82) |
| Missing | 1 |
| Grade | |
| 1-2 | 20 (18) |
| 3 | 92 (82) |
| Missing | 1 |
| Intratumoral TIL | |
| Mean | 3 |
| SD | 6.6 |
| Median | 1 |
| Q1-Q3 | 0-2 |
| Min-Max | 0-30 |
| Missing | 1 |
| Stromal TIL | |
| Mean | 25 |
| SD | 25.1 |
| Median | 15 |
| Q1-Q3 | 5-40 |
| Min-Max | 0-95 |

TABLE 33

GEO accessions of HER2 positive patients included in genomic data processing

| GEO accession | Center | Trial | Stromal TIL | Intratumoral TIL |
|---|---|---|---|---|
| GSM411295 | Bordet | TOP | 35 | 1 |
| GSM411369 | Bordet | TOP | 20 | 0 |
| GSM411366 | Bordet | TOP | 90 | 30 |
| GSM411351 | Bordet | TOP | 10 | 0 |
| GSM411365 | Bordet | TOP | 75 | 10 |
| GSM411338 | Bordet | TOP | 20 | 0 |
| GSM411358 | Bordet | TOP | 5 | 0 |
| GSM411362 | Bordet | TOP | 80 | 30 |
| GSM411307 | Bordet | TOP | 40 | 0 |
| GSM411291 | Bordet | TOP | 30 | 1 |
| GSM411292 | Bordet | TOP | 95 | 15 |
| GSM411393 | Bordet | TOP | 95 | not evaluable |
| GSM411376 | Bordet | TOP | 85 | 20 |
| GSM411305 | Bordet | TOP | 40 | 0 |

TABLE 34

Summary of genes achieving selection criterion (corrected p-value < 0.05) in univariate analysis of triple negative patients

| GENENAME | PROBEID | ENTREZ ID | SYMBOL | Estimate | Std. Error | LCI |
|---|---|---|---|---|---|---|
| chemokine (C—X—C motif) ligand 13 | 205242_at | 10563 | CXCL13 | 0.846 | 0.1521 | 0.548 |
| guanylate binding protein 1, interferon-inducible | 202269_x_at | 2633 | GBP1 | 0.870 | 0.1675 | 0.541 |
| sulfotransferase family 1E, estrogen-preferring, member 1 | 219934_s_at | 6783 | SULT1E1 | −2.844 | 0.5545 | −3.931 |
| immunoglobulin heavy constant gamma 3 (G3m marker) | 211430_s_at | 3502 | IGHG3 | 0.768 | 0.1516 | 0.471 |
| immunoglobulin kappa constant | 221671_x_at | 3514 | IGKC | 1.100 | 0.2177 | 0.673 |
| immunoglobulin kappa constant | 221651_x_at | 3514 | IGKC | 1.109 | 0.2196 | 0.679 |
| chemokine (C—X—C motif) ligand 10 | 204533_at | 3627 | CXCL10 | 0.914 | 0.1816 | 0.558 |
| immunoglobulin lambda joining 3 | 214677_x_at | 28831 | IGLJ3 | 0.771 | 0.1560 | 0.465 |
| immunoglobulin lambda-like polypeptide 3, pseudogene | 215946_x_at | 91353 | IGLL3P | 1.248 | 0.2534 | 0.751 |

TABLE 34-continued

Summary of genes achieving selection criterion (corrected p-value < 0.05) in univariate analysis of triple negative patients

| | | | | | | |
|---|---|---|---|---|---|---|
| immunoglobulin kappa constant | 215176_x_at | 3514 | IGKC | 0.708 | 0.1443 | 0.425 |
| immunoglobulin lambda constant 1 (Mcg marker) | 215121_x_at | 3537 | IGLC1 | 0.889 | 0.1821 | 0.532 |
| chemokine (C-C motif) ligand 5 | 1405_i_at | 6352 | CCL5 | 1.073 | 0.2203 | 0.641 |
| immunoglobulin lambda constant 1 (Mcg marker) | 209138_x_at | 3537 | IGLC1 | 0.804 | 0.1661 | 0.478 |
| immunoglobulin lambda variable cluster | 215379_x_at | 3546 | IGLV@ | 0.879 | 0.1825 | 0.522 |
| immunoglobulin kappa constant | 214836_x_at | 3514 | IGKC | 1.064 | 0.2210 | 0.631 |
| torsin family 3, member A | 218459_at | 64222 | TOR3A | 2.791 | 0.5812 | 1.652 |
| hepatic leukemia factor | 204753_s_at | 3131 | HLF | −1.884 | 0.3933 | −2.654 |
| immunoglobulin kappa constant | 214669_x_at | 3514 | IGKC | 0.894 | 0.1895 | 0.523 |
| signal transducer and activator of transcription 1, 91 kDa | 209969_s_at | 6772 | STAT1 | 1.068 | 0.2271 | 0.623 |
| chemokine (C-C motif) ligand 5 | 204655_at | 6352 | CCL5 | 1.073 | 0.2302 | 0.622 |
| chemokine (C-C motif) ligand 8 | 214038_at | 6355 | CCL8 | 0.844 | 0.1820 | 0.487 |
| NA | 211645_x_at | NA | NA | 0.688 | 0.1484 | 0.397 |
| absent in melanoma 2 | 206513_at | 9447 | AIM2 | 1.498 | 0.3256 | 0.859 |
| SLAM family member 8 | 219386_s_at | 56833 | SLAMF8 | 1.315 | 0.2872 | 0.752 |
| bromodomain adjacent to zinc finger domain, 1A | 217985_s_at | 11177 | BAZ1A | 1.994 | 0.4409 | 1.130 |
| post-GPI attachment to proteins 1 | 213469_at | 80055 | PGAP1 | −2.181 | 0.4841 | −3.129 |
| glucuronidase, beta pseudogene 11 | 213502_x_at | 91316 | GUSBP11 | 1.327 | 0.2969 | 0.745 |
| immunoglobulin heavy constant mu | 209374_s_at | 3507 | IGHM | 0.670 | 0.1503 | 0.376 |
| major histocompatibility complex, class II, DP alpha 1 | 211990_at | 3113 | HLA-DPA1 | 1.189 | 0.2711 | 0.658 |
| NA | 217378_x_at | NA | NA | 0.807 | 0.1844 | 0.446 |
| guanylate binding protein 1, interferon-inducible | 202270_at | 2633 | GBP1 | 0.806 | 0.1848 | 0.444 |
| tryptophanyl-tRNA synthetase | 200629_at | 7453 | WARS | 1.273 | 0.2929 | 0.699 |
| hepatic leukemia factor | 204754_at | 3131 | HLF | −2.149 | 0.4978 | −3.125 |
| chemokine (C—X—C motif) ligand 9 | 203915_at | 4283 | CXCL9 | 0.761 | 0.1766 | 0.414 |
| DEAD (Asp-Glu-Ala-Asp) box helicase 24 | 200702_s_at | 57062 | DDX24 | 2.355 | 0.5542 | 1.269 |
| immunoglobulin kappa constant | 216576_x_at | 3514 | IGKC | 0.702 | 0.1676 | 0.373 |
| immunoglobulin kappa constant | 217157_x_at | 3514 | IGKC | 0.998 | 0.2400 | 0.528 |
| tripartite motif containing 38 | 203567_s_at | 10475 | TRIM38 | 1.972 | 0.4834 | 1.025 |
| adhesion G protein-coupled receptor L3 | 209867_s_at | 23284 | ADGRL3 | −2.036 | 0.5032 | −3.023 |
| SR-related CTD-associated factor 11 | 213850_s_at | 9169 | SCAF11 | 2.140 | 0.5310 | 1.100 |
| NA | 216401_x_at | NA | NA | 0.748 | 0.1860 | 0.384 |
| interferon-induced protein 44-like | 204439_at | 10964 | IFI44L | 0.703 | 0.1750 | 0.361 |
| SWI/SNF related, matrix associated, actin dependent regulator of chromatin, subfamily c, member 1 | 201072_s_at | 6599 | SMARCC1 | 2.522 | 0.6280 | 1.291 |
| low density lipoprotein receptor-related protein 4 | 212850_s_at | 4038 | LRP4 | −2.226 | 0.5552 | −3.314 |
| interferon-induced protein 44 | 214453_s_at | 10561 | IFI44 | 0.810 | 0.2041 | 0.410 |
| hepatic leukemia factor | 204755_x_at | 3131 | HLF | −1.900 | 0.4809 | −2.842 |
| immunoglobulin kappa constant | 214768_x_at | 3514 | IGKC | 0.655 | 0.1660 | 0.329 |
| chemokine (C-C motif) ligand 4 | 204103_at | 6351 | CCL4 | 1.294 | 0.3299 | 0.647 |
| chemokine (C—X—C motif) receptor 6 | 206974_at | 10663 | CXCR6 | 2.097 | 0.5355 | 1.048 |
| interferon, gamma-inducible protein 16 | 206332_s_at | 3428 | IFI16 | 0.926 | 0.2371 | 0.461 |
| interferon, gamma-inducible protein 16 | 208965_s_at | 3428 | IFI16 | 0.949 | 0.2437 | 0.471 |
| syndecan 2 | 212157_at | 6383 | SDC2 | −1.661 | 0.4273 | −2.498 |
| immunoglobulin heavy locus | 217281_x_at | 3492 | IGH | 0.778 | 0.2002 | 0.385 |
| major histocompatibility complex, class II, DQ beta 1 | 209823_x_at | 3119 | HLA-DQB1 | 1.130 | 0.2916 | 0.559 |
| nuclear factor of kappa light polypeptide gene enhancer in B-cells inhibitor, alpha | 201502_s_at | 4792 | NFKBIA | 1.612 | 0.4160 | 0.797 |
| immunoglobulin lambda joining 3 | 211798_x_at | 28831 | IGLJ3 | 0.737 | 0.1914 | 0.362 |
| major histocompatibility complex, class II, DM alpha | 217478_s_at | 3108 | HLA-DMA | 1.153 | 0.2998 | 0.566 |
| ATP-binding cassette, sub-family G (WHITE), member 2 (Junior blood group) | 209735_at | 9429 | ABCG2 | −2.235 | 0.5817 | −3.375 |
| collagen, type XVII, alpha 1 | 204636_at | 1308 | COL17A1 | −2.010 | 0.5235 | −3.037 |
| catenin (cadherin-associated protein), delta 2 | 209617_s_at | 1501 | CTNND2 | −1.897 | 0.4944 | −2.866 |
| glutamyl aminopeptidase (aminopeptidase A) | 204845_s_at | 2028 | ENPEP | −1.722 | 0.4505 | −2.605 |
| interferon, gamma-inducible protein 16 | 208966_x_at | 3428 | IFI16 | 0.869 | 0.2275 | 0.423 |
| proteasome (prosome, macropain) subunit, alpha type, 6 | 208805_at | 5687 | PSMA6 | 2.038 | 0.5334 | 0.992 |

TABLE 34-continued

Summary of genes achieving selection criterion (corrected p-value < 0.05) in univariate analysis of triple negative patients

| | | | | | | |
|---|---|---|---|---|---|---|
| E74-like factor 4 (ets domain transcription factor) | 31845_at | 2000 | ELF4 | 1.897 | 0.4981 | 0.920 |
| immunoglobulin kappa variable 1D-13 | 216207_x_at | 28902 | IGKV1D-13 | 0.797 | 0.2097 | 0.386 |
| COP9 signalosome subunit 8 | 202143_s_at | 10920 | COPS8 | −2.346 | 0.6178 | −3.556 |
| serpin peptidase inhibitor, clade G (C1 inhibitor), member 1 | 200986_at | 710 | SERPING1 | 1.074 | 0.2830 | 0.520 |
| transportin 1 | 209225_x_at | 3842 | TNPO1 | 2.195 | 0.5790 | 1.060 |
| cytochrome b-245, beta polypeptide | 203923_s_at | 1536 | CYBB | 1.241 | 0.3278 | 0.598 |
| DEAD (Asp-Glu-Ala-Asp) box polypeptide 58 | 218943_s_at | 23586 | DDX58 | 1.020 | 0.2697 | 0.491 |
| centrosomal protein 350 kDa | 213956_at | 9857 | CEP350 | 1.844 | 0.4880 | 0.888 |
| immunoglobulin heavy constant alpha 1 | 216510_x_at | 3493 | IGHA1 | 0.590 | 0.1563 | 0.283 |
| jun D proto-oncogene | 203752_s_at | 3727 | JUND | 1.729 | 0.4607 | 0.827 |
| immunoglobulin kappa constant | 211644_x_at | 3514 | IGKC | 0.565 | 0.1506 | 0.270 |
| immunoglobulin lambda constant 1 (Mcg marker) | 217148_x_at | 3537 | IGLC1 | 0.659 | 0.1762 | 0.313 |
| immunoglobulin heavy locus | 217022_s_at | 3492 | IGH | 0.517 | 0.1391 | 0.245 |
| apolipoprotein B mRNA editing enzyme, catalytic polypeptide-like 3G | 204205_at | 60489 | APOBEC3G | 1.261 | 0.3395 | 0.595 |
| NA | 217480_x_at | NA | NA | 0.884 | 0.2391 | 0.415 |
| peroxisomal biogenesis factor 2 | 210296_s_at | 5828 | PEX2 | −1.766 | 0.4797 | −2.706 |

| GENENAME | PROBEID | HCI | t value | Pval | FDR | bonferroni |
|---|---|---|---|---|---|---|
| chemokine (C—X—C motif) ligand 13 | 205242_at | 1.144 | 5.563 | 0.0000 | 0.0024 | 0.0024 |
| guanylate binding protein 1, interferon-inducible | 202269_x_at | 1.198 | 5.192 | 0.0000 | 0.0033 | 0.0116 |
| sulfotransferase family 1E, estrogen-preferring, member 1 | 219934_s_at | −1.757 | −5.129 | 0.0000 | 0.0033 | 0.0151 |
| immunoglobulin heavy constant gamma 3 (G3m marker) | 211430_s_at | 1.065 | 5.064 | 0.0000 | 0.0033 | 0.0198 |
| immunoglobulin kappa constant | 221671_x_at | 1.527 | 5.054 | 0.0000 | 0.0033 | 0.0207 |
| immunoglobulin kappa constant | 221651_x_at | 1.540 | 5.051 | 0.0000 | 0.0033 | 0.0209 |
| chemokine (C—X—C motif) ligand 10 | 204533_at | 1.270 | 5.029 | 0.0000 | 0.0033 | 0.0229 |
| immunoglobulin lambda joining 3 | 214677_x_at | 1.076 | 4.940 | 0.0000 | 0.0036 | 0.0330 |
| immunoglobulin lambda-like polypeptide 3, pseudogene | 215946_x_at | 1.745 | 4.925 | 0.0000 | 0.0036 | 0.0352 |
| immunoglobulin kappa constant | 215176_x_at | 0.991 | 4.903 | 0.0000 | 0.0036 | 0.0384 |
| immunoglobulin lambda constant 1 (Mcg marker) | 215121_x_at | 1.246 | 4.879 | 0.0000 | 0.0036 | 0.0423 |
| chemokine (C-C motif) ligand 5 | 1405_i_at | 1.505 | 4.872 | 0.0000 | 0.0036 | 0.0436 |
| immunoglobulin lambda constant 1 (Mcg marker) | 209138_x_at | 1.129 | 4.840 | 0.0000 | 0.0036 | 0.0495 |
| immunoglobulin lambda variable cluster | 215379_x_at | 1.237 | 4.818 | 0.0000 | 0.0036 | 0.0541 |
| immunoglobulin kappa constant | 214836_x_at | 1.497 | 4.814 | 0.0000 | 0.0036 | 0.0550 |
| torsin family 3, member A | 218459_at | 3.931 | 4.802 | 0.0000 | 0.0036 | 0.0577 |
| hepatic leukemia factor | 204753_s_at | −1.113 | −4.790 | 0.0000 | 0.0036 | 0.0607 |
| immunoglobulin kappa constant | 214669_x_at | 1.266 | 4.719 | 0.0000 | 0.0045 | 0.0806 |
| signal transducer and activator of transcription 1, 91 kDa | 209969_s_at | 1.513 | 4.705 | 0.0000 | 0.0045 | 0.0850 |
| chemokine (C-C motif) ligand 5 | 204655_at | 1.524 | 4.661 | 0.0000 | 0.0051 | 0.1013 |
| chemokine (C-C motif) ligand 8 | 214038_at | 1.201 | 4.639 | 0.0000 | 0.0051 | 0.1109 |
| NA | 211645_x_at | 0.979 | 4.636 | 0.0000 | 0.0051 | 0.1120 |
| absent in melanoma 2 | 206513_at | 2.136 | 4.599 | 0.0000 | 0.0056 | 0.1293 |
| SLAM family member 8 | 219386_s_at | 1.878 | 4.578 | 0.0000 | 0.0059 | 0.1408 |
| bromodomain adjacent to zinc finger domain, 1A | 217985_s_at | 2.858 | 4.523 | 0.0000 | 0.0070 | 0.1747 |
| post-GPI attachment to proteins 1 | 213469_at | −1.232 | −4.505 | 0.0000 | 0.0072 | 0.1872 |
| glucuronidase, beta pseudogene 11 | 213502_x_at | 1.909 | 4.469 | 0.0000 | 0.0079 | 0.2151 |
| immunoglobulin heavy constant mu | 209374_s_at | 0.965 | 4.461 | 0.0000 | 0.0079 | 0.2221 |
| major histocompatibility complex, class II, DP alpha 1 | 211990_at | 1.720 | 4.387 | 0.0000 | 0.0101 | 0.2943 |
| NA | 217378_x_at | 1.168 | 4.378 | 0.0000 | 0.0102 | 0.3055 |
| guanylate binding protein 1, interferon-inducible | 202270_at | 1.169 | 4.364 | 0.0000 | 0.0104 | 0.3219 |
| tryptophanyl-tRNA synthetase | 200629_at | 1.847 | 4.346 | 0.0000 | 0.0108 | 0.3450 |
| hepatic leukemia factor | 204754_at | −1.174 | −4.318 | 0.0000 | 0.0116 | 0.3840 |
| chemokine (C—X—C motif) ligand 9 | 203915_at | 1.107 | 4.306 | 0.0000 | 0.0118 | 0.4013 |
| DEAD (Asp-Glu-Ala-Asp) box helicase 24 | 200702_s_at | 3.441 | 4.249 | 0.0000 | 0.0142 | 0.4970 |
| immunoglobulin kappa constant | 216576_x_at | 1.030 | 4.188 | 0.0001 | 0.0173 | 0.6242 |
| immunoglobulin kappa constant | 217157_x_at | 1.468 | 4.158 | 0.0001 | 0.0189 | 0.6995 |

TABLE 34-continued

Summary of genes achieving selection criterion (corrected p-value < 0.05) in univariate analysis of triple negative patients

| | | | | | | |
|---|---|---|---|---|---|---|
| tripartite motif containing 38 | 203567_s_at | 2.919 | 4.079 | 0.0001 | 0.0246 | 0.9332 |
| adhesion G protein-coupled receptor L3 | 209867_s_at | −1.050 | −4.047 | 0.0001 | 0.0269 | 1.0000 |
| SR-related CTD-associated factor 11 | 213850_s_at | 3.181 | 4.031 | 0.0001 | 0.0273 | 1.0000 |
| NA | 216401_x_at | 1.113 | 4.023 | 0.0001 | 0.0273 | 1.0000 |
| interferon-induced protein 44-like | 204439_at | 1.046 | 4.021 | 0.0001 | 0.0273 | 1.0000 |
| SWI/SNF related, matrix associated, actin dependent regulator of chromatin, subfamily c, member 1 | 201072_s_at | 3.753 | 4.016 | 0.0001 | 0.0273 | 1.0000 |
| low density lipoprotein receptor-related protein 4 | 212850_s_at | −1.138 | −4.009 | 0.0001 | 0.0274 | 1.0000 |
| interferon-induced protein 44 | 214453_s_at | 1.210 | 3.969 | 0.0001 | 0.0309 | 1.0000 |
| hepatic leukemia factor | 204755_x_at | −0.957 | −3.950 | 0.0001 | 0.0324 | 1.0000 |
| immunoglobulin kappa constant | 214768_x_at | 0.980 | 3.943 | 0.0002 | 0.0326 | 1.0000 |
| chemokine (C-C motif) ligand 4 | 204103_at | 1.941 | 3.922 | 0.0002 | 0.0343 | 1.0000 |
| chemokine (C—X—C motif) receptor 6 | 206974_at | 3.147 | 3.916 | 0.0002 | 0.0343 | 1.0000 |
| interferon, gamma-inducible protein | 206332_s_at | 1.391 | 3.905 | 0.0002 | 0.0351 | 1.0000 |
| interferon, gamma-inducible protein 16 | 208965_s_at | 1.427 | 3.895 | 0.0002 | 0.0354 | 1.0000 |
| syndecan 2 | 212157_at | −0.823 | −3.886 | 0.0002 | 0.0354 | 1.0000 |
| immunoglobulin heavy locus | 217281_x_at | 1.170 | 3.885 | 0.0002 | 0.0354 | 1.0000 |
| major histocompatibility complex, class II, DQ beta 1 | 209823_x_at | 1.702 | 3.877 | 0.0002 | 0.0354 | 1.0000 |
| nuclear factor of kappa light polypeptide gene enhancer in B-cells inhibitor, alpha | 201502_s_at | 2.427 | 3.875 | 0.0002 | 0.0354 | 1.0000 |
| immunoglobulin lambda joining 3 | 211798_x_at | 1.112 | 3.851 | 0.0002 | 0.0371 | 1.0000 |
| major histocompatibility complex, class II, DM alpha | 217478_s_at | 1.741 | 3.848 | 0.0002 | 0.0371 | 1.0000 |
| ATP-binding cassette, sub-family G (WHITE), member 2 (Junior blood group) | 209735_at | −1.095 | −3.842 | 0.0002 | 0.0371 | 1.0000 |
| collagen, type XVII, alpha 1 | 204636_at | −0.984 | −3.840 | 0.0002 | 0.0371 | 1.0000 |
| catenin (cadherin-associated protein), delta 2 | 209617_s_at | −0.928 | −3.837 | 0.0002 | 0.0371 | 1.0000 |
| glutamyl aminopeptidase (aminopeptidase A) | 204845_s_at | −0.839 | −3.822 | 0.0002 | 0.0376 | 1.0000 |
| interferon, gamma-inducible protein 16 | 208966_x_at | 1.315 | 3.821 | 0.0002 | 0.0376 | 1.0000 |
| proteasome (prosome, macropain) subunit, alpha type, 6 | 208805_at | 3.083 | 3.820 | 0.0002 | 0.0376 | 1.0000 |
| E74-like factor 4 (ets domain transcription factor) | 31845_at | 2.873 | 3.808 | 0.0002 | 0.0384 | 1.0000 |
| immunoglobulin kappa variable 1D-13 | 216207_x_at | 1.208 | 3.799 | 0.0003 | 0.0384 | 1.0000 |
| COP9 signalosome subunit 8 | 202143_s_at | −1.135 | −3.796 | 0.0003 | 0.0384 | 1.0000 |
| serpin peptidase inhibitor, clade G (C1 inhibitor), member 1 | 200986_at | 1.629 | 3.796 | 0.0003 | 0.0384 | 1.0000 |
| transportin 1 | 209225_x_at | 3.330 | 3.791 | 0.0003 | 0.0385 | 1.0000 |
| cytochrome b-245, beta polypeptide | 203923_s_at | 1.883 | 3.785 | 0.0003 | 0.0385 | 1.0000 |
| DEAD (Asp-Glu-Ala-Asp) box polypeptide 58 | 218943_s_at | 1.548 | 3.780 | 0.0003 | 0.0385 | 1.0000 |
| centrosomal protein 350 kDa | 213956_at | 2.801 | 3.779 | 0.0003 | 0.0385 | 1.0000 |
| immunoglobulin heavy constant alpha 1 | 216510_x_at | 0.896 | 3.771 | 0.0003 | 0.0390 | 1.0000 |
| jun D proto-oncogene | 203752_s_at | 2.632 | 3.754 | 0.0003 | 0.0405 | 1.0000 |
| immunoglobulin kappa constant | 211644_x_at | 0.860 | 3.753 | 0.0003 | 0.0405 | 1.0000 |
| immunoglobulin lambda constant 1 (Mcg marker) | 217148_x_at | 1.004 | 3.738 | 0.0003 | 0.0420 | 1.0000 |
| immunoglobulin heavy locus | 217022_s_at | 0.790 | 3.721 | 0.0003 | 0.0440 | 1.0000 |
| apolipoprotein B mRNA editing enzyme, catalytic polypeptide-like 3G | 204205_at | 1.926 | 3.714 | 0.0003 | 0.0445 | 1.0000 |
| NA | 217480_x_at | 1.353 | 3.697 | 0.0004 | 0.0465 | 1.0000 |
| peroxisomal biogenesis factor 2 | 210296_s_at | −0.826 | −3.682 | 0.0004 | 0.0485 | 1.0000 |

TABLE 35

Summary of genes achieving selection criterion (corrected p-value < 0.05) in univariate analysis of all patients stratified on HER status

| GENENAME | PROBEID | ENTREZ ID | SYMBOL | Estimate | Std. Error | LCI |
|---|---|---|---|---|---|---|
| guanylate binding protein 1, interferon-inducible | 202269_x_at | 2633 | GBP1 | 0.858 | 0.1588 | 0.547 |
| immunoglobulin heavy constant gamma 3 (G3m marker) | 211430_s_at | 3502 | IGHG3 | 0.742 | 0.1408 | 0.466 |
| chemokine (C—X—C motif) ligand 13 | 205242_at | 10563 | CXCL13 | 0.734 | 0.1400 | 0.460 |
| sulfotransferase family 1E, estrogen-preferring, member 1 | 219934_s_at | 6783 | SULT1E1 | −2.679 | 0.5124 | −3.683 |
| chemokine (C—X—C motif) ligand 10 | 204533_at | 3627 | CXCL10 | 0.876 | 0.1715 | 0.540 |
| immunoglobulin lambda joining 3 | 214677_x_at | 28831 | IGLJ3 | 0.732 | 0.1445 | 0.449 |
| immunoglobulin kappa constant | 221651_x_at | 3514 | IGKC | 1.034 | 0.2050 | 0.633 |
| immunoglobulin kappa constant | 221671_x_at | 3514 | IGKC | 1.025 | 0.2034 | 0.626 |
| immunoglobulin lambda constant 1 (Mcg marker) | 215121_x_at | 3537 | IGLC1 | 0.848 | 0.1689 | 0.517 |
| immunoglobulin lambda-like polypeptide 3, pseudogene | 215946_x_at | 91353 | IGLL3P | 1.164 | 0.2325 | 0.708 |
| immunoglobulin lambda constant 1 (Mcg marker) | 209138_x_at | 3537 | IGLC1 | 0.762 | 0.1536 | 0.461 |
| immunoglobulin lambda variable cluster | 215379_x_at | 3546 | IGLV@ | 0.835 | 0.1689 | 0.504 |
| hepatic leukemia factor | 204753_s_at | 3131 | HLF | −1.798 | 0.3681 | −2.520 |
| immunoglobulin kappa constant | 215176_x_at | 3514 | IGKC | 0.640 | 0.1315 | 0.382 |
| immunoglobulin kappa constant | 214836_x_at | 3514 | IGKC | 0.994 | 0.2050 | 0.593 |
| bromodomain adjacent to zinc finger domain, 1A | 217985_s_at | 11177 | BAZ1A | 2.039 | 0.4204 | 1.215 |
| post-GPI attachment to proteins 1 | 213469_at | 80055 | PGAP1 | −2.213 | 0.4568 | −3.109 |
| signal transducer and activator of transcription 1, 91 kDa | 209969_s_at | 6772 | STAT1 | 1.027 | 0.2146 | 0.607 |
| immunoglobulin kappa constant | 214669_x_at | 3514 | IGKC | 0.833 | 0.1745 | 0.491 |
| chemokine (C-C motif) ligand 8 | 214038_at | 6355 | CCL8 | 0.792 | 0.1677 | 0.464 |
| guanylate binding protein 1, interferon-inducible | 202270_at | 2633 | GBP1 | 0.820 | 0.1744 | 0.478 |
| SLAM family member 8 | 219386_s_at | 56833 | SLAMF8 | 1.267 | 0.2719 | 0.734 |
| hepatic leukemia factor | 204754_s_at | 3131 | HLF | −2.206 | 0.4752 | −3.137 |
| NA | 211645_x_at | NA | NA | 0.625 | 0.1350 | 0.361 |
| absent in melanoma 2 | 206513_at | 9447 | AIM2 | 1.432 | 0.3108 | 0.823 |
| tryptophanyl-tRNA synthetase | 200629_at | 7453 | WARS | 1.226 | 0.2680 | 0.700 |
| glucuronidase, beta pseudogene 11 | 213502_x_at | 91316 | GUSBP11 | 1.208 | 0.2675 | 0.684 |
| chemokine (C-C motif) ligand 5 | 1405_i_at | 6352 | CCL5 | 0.930 | 0.2075 | 0.524 |
| NA | 217378_x_at | NA | NA | 0.732 | 0.1678 | 0.403 |
| major histocompatibility complex, class II, DP alpha 1 | 211990_at | 3113 | HLA-DPA1 | 1.118 | 0.2584 | 0.611 |
| torsin family 3, member A | 218459_at | 64222 | TOR3A | 2.365 | 0.5484 | 1.290 |
| chemokine (C-C motif) ligand 5 | 204655_at | 6352 | CCL5 | 0.935 | 0.2172 | 0.509 |
| immunoglobulin heavy constant mu | 209374_s_at | 3507 | IGHM | 0.595 | 0.1391 | 0.322 |
| low density lipoprotein receptor-related protein 4 | 212850_s_at | 4038 | LRP4 | −2.212 | 0.5208 | −3.232 |
| chemokine (C—X—C motif) ligand 9 | 203915_at | 4283 | CXCL9 | 0.696 | 0.1643 | 0.375 |
| ATP-binding cassette, sub-family G (WHITE), member 2 (Junior blood group) | 209735_at | 9429 | ABCG2 | −2.286 | 0.5416 | −3.348 |
| immunoglobulin kappa constant | 216576_x_at | 3514 | IGKC | 0.644 | 0.1527 | 0.345 |
| major histocompatibility complex, class II, DQ beta 1 | 209823_x_at | 3119 | HLA-DQB1 | 1.113 | 0.2670 | 0.590 |
| chemokine (C-C motif) ligand 4 | 204103_at | 6351 | CCL4 | 1.257 | 0.3031 | 0.663 |
| immunoglobulin kappa constant | 214768_x_at | 3514 | IGKC | 0.611 | 0.1479 | 0.321 |
| immunoglobulin kappa constant | 217157_x_at | 3514 | IGKC | 0.889 | 0.2184 | 0.461 |
| NA | 216401_x_at | NA | NA | 0.684 | 0.1691 | 0.352 |
| hepatic leukemia factor | 204755_x_at | 3131 | HLF | −1.836 | 0.4564 | −2.730 |
| cytochrome b-245, beta polypeptide | 203923_s_at | 1536 | CYBB | 1.237 | 0.3078 | 0.633 |
| DEAD (Asp-Glu-Ala-Asp) box helicase 24 | 200702_s_at | 57062 | DDX24 | 2.117 | 0.5282 | 1.082 |
| immunoglobulin lambda joining 3 | 211798_x_at | 28831 | IGLJ3 | 0.682 | 0.1711 | 0.347 |
| COP9 signalosome subunit 8 | 202143_s_at | 10920 | COPS8 | −2.274 | 0.5721 | −3.395 |
| adhesion G protein-coupled receptor L3 | 209867_s_at | 23284 | ADGRL3 | −1.927 | 0.4865 | −2.880 |
| collagen, type XVII, alpha 1 | 204636_at | 1308 | COL17A1 | −2.000 | 0.5050 | −2.990 |
| immunoglobulin heavy constant alpha 1 | 216510_x_at | 3493 | IGHA1 | 0.554 | 0.1408 | 0.278 |
| proteasome (prosome, macropain) subunit, alpha type, 6 | 208805_at | 5687 | PSMA6 | 1.947 | 0.4954 | 0.976 |
| major histocompatibility complex, class II, DM alpha | 217478_s_at | 3108 | HLA-DMA | 1.078 | 0.2763 | 0.536 |
| immunoglobulin heavy locus | 217281_x_at | 3492 | IGH | 0.699 | 0.1792 | 0.348 |
| tripartite motif containing 38 | 203567_s_at | 10475 | TRIM38 | 1.787 | 0.4596 | 0.887 |
| cathepsin C | 201487_at | 1075 | CTSC | 1.138 | 0.2945 | 0.561 |
| syndecan 2 | 212157_at | 6383 | SDC2 | −1.548 | 0.4007 | −2.333 |
| follistatin | 207345_at | 10468 | FST | −2.296 | 0.5952 | −3.463 |
| jun D proto-oncogene | 203752_s_at | 3727 | JUND | 1.648 | 0.4282 | 0.809 |
| chemokine (C—X—C motif) receptor 6 | 206974_at | 10663 | CXCR6 | 1.889 | 0.4943 | 0.920 |
| immunoglobulin lambda constant 1 (Mcg marker) | 217148_x_at | 3537 | IGLC1 | 0.604 | 0.1583 | 0.294 |
| clusterin-like 1 (retinal) | 206556_at | 27098 | CLUL1 | −1.887 | 0.4949 | −2.856 |
| apolipoprotein L, 6 | 219716_at | 80830 | APOL6 | 1.617 | 0.4261 | 0.782 |
| interferon-induced protein 44-like | 204439_at | 10964 | IFI44L | 0.625 | 0.1647 | 0.302 |
| immunoglobulin kappa constant | 211644_x_at | 3514 | IGKC | 0.519 | 0.1368 | 0.251 |
| KLF3 antisense RNA 1 | 219871_at | 79667 | KLF3-AS1 | −2.204 | 0.5832 | −3.347 |

TABLE 35-continued

Summary of genes achieving selection criterion (corrected p-value < 0.05) in univariate analysis of all patients stratified on HER status

| | | | | | | |
|---|---|---|---|---|---|---|
| immunoglobulin lambda variable 1-44 | 217227_x_at | 28823 | IGLV1-44 | 0.710 | 0.1879 | 0.342 |
| transporter 1, ATP-binding cassette, sub-family B (MDR/TAP) | 202307_s_at | 6890 | TAP1 | 0.928 | 0.2457 | 0.446 |
| ubiquitin-conjugating enzyme E2L6 | 201649_at | 9246 | UBE2L6 | 1.073 | 0.2850 | 0.515 |
| interferon-induced protein 44 | 214453_at | 10561 | IFI44 | 0.715 | 0.1901 | 0.342 |
| major histocompatibility complex, class II, DQ beta 1 | 211656_x_at | 3119 | HLA-DQB1 | 1.225 | 0.3261 | 0.586 |
| immunoglobulin kappa variable 1D-13 | 216207_x_at | 28902 | IGKV1D-13 | 0.715 | 0.1904 | 0.342 |
| glutamyl aminopeptidase (aminopeptidase A) | 204845_s_at | 2028 | ENPEP | −1.572 | 0.4197 | −2.394 |
| immunoglobulin heavy locus | 211868_x_at | 3492 | IGH | 0.921 | 0.2463 | 0.438 |
| transformation/transcription domain-associated protein | 214908_s_at | 8295 | TRRAP | −1.685 | 0.4522 | −2.572 |
| cyclin D2 | 200951_s_at | 894 | CCND2 | 1.798 | 0.4841 | 0.849 |
| guanylate binding protein 2, interferon-inducible | 202748_at | 2634 | GBP2 | 1.005 | 0.2708 | 0.474 |
| signal transducer and activator of transcription 1, 91 kDa | AFFX-HUMIS | 6772 | STAT1 | 1.004 | 0.2709 | 0.473 |
| SR-related CTD-associated factor 11 | 213850_s_at | 9169 | SCAF11 | 1.863 | 0.5025 | 0.878 |
| signal transducer and activator of transcription 1, 91 kDa | 200887_s_at | 6772 | STAT1 | 0.950 | 0.2565 | 0.447 |
| butyrophilin, subfamily 3, member A2 | 209846_s_at | 11118 | BTN3A2 | 1.063 | 0.2870 | 0.500 |
| tryptophanyl-tRNA synthetase | 200628_s_at | 7453 | WARS | 1.203 | 0.3260 | 0.564 |
| complement component 1, q subcomponent, A chain | 218232_at | 712 | C1QA | 0.898 | 0.2435 | 0.421 |
| NA | 217480_x_at | NA | NA | 0.795 | 0.2157 | 0.372 |
| centrosomal protein 350 kDa | 213956_at | 9857 | CEP350 | 1.712 | 0.4647 | 0.801 |
| FAT atypical cadherin 4 | 219427_at | 79633 | FAT4 | −2.095 | 0.5687 | −3.209 |
| transportin 1 | 209225_x_at | 3842 | TNPO1 | 2.024 | 0.5498 | 0.946 |
| membrane associated guanylate kinase, WW and PDZ domain containing 2 | 209737_at | 9863 | MAGI2 | −1.551 | 0.4216 | −2.378 |
| ELL associated factor 2 | 219551_at | 55840 | EAF2 | 1.364 | 0.3708 | 0.637 |
| hes-related family bHLH transcription factor with YRPW motif 1 | 44783_s_at | 23462 | HEY1 | −1.186 | 0.3227 | −1.818 |
| odontogenic, ameloblast asssociated | 220133_at | 54959 | ODAM | −0.713 | 0.1940 | −1.093 |
| catenin (cadherin-associated protein), delta 2 | 209617_s_at | 1501 | CTNND2 | −1.639 | 0.4478 | −2.517 |
| carbonic anhydrase II | 209301_at | 760 | CA2 | −0.777 | 0.2124 | −1.193 |
| immunoglobulin kappa locus | 211650_x_at | 50802 | IGK | 0.669 | 0.1832 | 0.310 |
| immunoglobulin kappa locus | 214916_x_at | 50802 | IGK | 0.659 | 0.1809 | 0.305 |
| dystonin | 216918_s_at | 667 | DST | −1.766 | 0.4847 | −2.716 |
| butyrophilin, subfamily 3, member A3 | 204820_s_at | 10384 | BTN3A3 | 1.093 | 0.3005 | 0.504 |
| immunoglobulin lambda joining 3 | 216984_x_at | 28831 | IGLJ3 | 0.637 | 0.1753 | 0.294 |
| apolipoprotein B mRNA editing enzyme, catalytic polypeptide-like 3G | 204205_at | 60489 | APOBEC3G | 1.143 | 0.3156 | 0.525 |
| peroxisomal biogenesis factor 1 | 215023_s_at | 5189 | PEX1 | −1.379 | 0.3808 | −2.126 |
| interferon, gamma-inducible protein 16 | 208965_s_at | 3428 | IFI16 | 0.843 | 0.2338 | 0.385 |
| interferon, gamma-inducible protein 16 | 206332_s_at | 3428 | IFI16 | 0.819 | 0.2271 | 0.374 |
| immunoglobulin heavy constant alpha 1 | 211641_x_at | 3493 | IGHA1 | 0.919 | 0.2550 | 0.419 |
| butyrophilin, subfamily 3, member A3 | 204821_at | 10384 | BTN3A3 | 1.442 | 0.4005 | 0.657 |
| fibroblast growth factor receptor 1 | 210973_s_at | 2260 | FGFR1 | −1.315 | 0.3657 | −2.032 |
| staufen double-stranded RNA binding protein 2 | 204226_at | 27067 | STAU2 | −1.723 | 0.4791 | −2.662 |
| CD38 molecule | 205692_s_at | 952 | CD38 | 1.187 | 0.3305 | 0.539 |
| interferon regulatory factor 9 | 203882_at | 10379 | IRF9 | 1.265 | 0.3530 | 0.573 |
| butyrophilin, subfamily 3, member A3 | 38241_at | 10384 | BTN3A3 | 1.235 | 0.3452 | 0.558 |
| interferon stimulated exonuclease gene 20 kDa | 204698_at | 3669 | ISG20 | 0.941 | 0.2631 | 0.425 |
| NA | 217179_x_at | NA | NA | 0.635 | 0.1780 | 0.286 |
| tumor necrosis factor (ligand) superfamily, member 10 | 202688_at | 8743 | TNFSF10 | 0.699 | 0.1964 | 0.315 |
| major histocompatibility complex, class II, DR beta 4 | 208306_x_at | 3126 | HLA-DRB4 | 1.248 | 0.3511 | 0.560 |
| CD163 molecule | 203645_s_at | 9332 | CD163 | 0.914 | 0.2575 | 0.410 |
| hes-related family bHLH transcription factor with YRPW motif 1 | 218839_at | 23462 | HEY1 | −1.456 | 0.4101 | −2.260 |

| GENENAME | PROBEID | HCI | t value | Pval | FDR | bonferroni |
|---|---|---|---|---|---|---|
| guanylate binding protein 1, interferon-inducible | 202269_x_at | 1.169 | 5.404 | 0.0000 | 0.0021 | 0.0039 |
| immunoglobulin heavy constant gamma 3 (G3m marker) | 211430_s_at | 1.018 | 5.270 | 0.0000 | 0.0021 | 0.0069 |
| chemokine (C—X—C motif) ligand 13 | 205242_at | 1.008 | 5.242 | 0.0000 | 0.0021 | 0.0078 |
| sulfotransferase family 1E, estrogen-preferring, member 1 | 219934_s_at | −1.674 | −5.227 | 0.0000 | 0.0021 | 0.0084 |
| chemokine (C—X—C motif) ligand 10 | 204533_at | 1.212 | 5.105 | 0.0000 | 0.0022 | 0.0141 |
| immunoglobulin lambda joining 3 | 214677_x_at | 1.015 | 5.068 | 0.0000 | 0.0022 | 0.0165 |
| immunoglobulin kappa constant | 221651_x_at | 1.436 | 5.046 | 0.0000 | 0.0022 | 0.0182 |
| immunoglobulin kappa constant | 221671_x_at | 1.423 | 5.036 | 0.0000 | 0.0022 | 0.0189 |
| immunoglobulin lambda constant 1 (Mcg marker) | 215121_x_at | 1.180 | 5.022 | 0.0000 | 0.0022 | 0.0201 |
| immunoglobulin lambda-like polypeptide 3, pseudogene | 215946_x_at | 1.619 | 5.005 | 0.0000 | 0.0022 | 0.0216 |

TABLE 35-continued

Summary of genes achieving selection criterion (corrected p-value < 0.05) in univariate analysis
of all patients stratified on HER status

| | | | | | | |
|---|---|---|---|---|---|---|
| immunoglobulin lambda constant 1 (Mcg marker) | 209138_x_at | 1.063 | 4.962 | 0.0000 | 0.0023 | 0.0259 |
| immunoglobulin lambda variable cluster | 215379_x_at | 1.166 | 4.944 | 0.0000 | 0.0023 | 0.0279 |
| hepatic leukemia factor | 204753_s_at | −1.077 | −4.886 | 0.0000 | 0.0025 | 0.0356 |
| immunoglobulin kappa constant | 215176_x_at | 0.898 | 4.868 | 0.0000 | 0.0025 | 0.0384 |
| immunoglobulin kappa constant | 214836_x_at | 1.396 | 4.851 | 0.0000 | 0.0025 | 0.0411 |
| bromodomain adjacent to zinc finger domain, 1A | 217985_s_at | 2.863 | 4.850 | 0.0000 | 0.0025 | 0.0414 |
| post-GPI attachment to proteins 1 | 213469_at | −1.318 | −4.845 | 0.0000 | 0.0025 | 0.0421 |
| signal transducer and activator of transcription 1, 91 kDa | 209969_s_at | 1.448 | 4.787 | 0.0000 | 0.0030 | 0.0536 |
| immunoglobulin kappa constant | 214669_x_at | 1.175 | 4.771 | 0.0000 | 0.0030 | 0.0571 |
| chemokine (C-C motif) ligand 8 | 214038_at | 1.121 | 4.723 | 0.0000 | 0.0035 | 0.0695 |
| guanylate binding protein 1, interferon-inducible | 202270_at | 1.162 | 4.702 | 0.0000 | 0.0036 | 0.0757 |
| SLAM family member 8 | 219386_s_at | 1.800 | 4.660 | 0.0000 | 0.0041 | 0.0899 |
| hepatic leukemia factor | 204754_at | −1.275 | −4.643 | 0.0000 | 0.0042 | 0.0965 |
| NA | 211645_x_at | 0.890 | 4.631 | 0.0000 | 0.0042 | 0.1010 |
| absent in melanoma 2 | 206513_at | 2.041 | 4.608 | 0.0000 | 0.0044 | 0.1109 |
| tryptophanyl-tRNA synthetase | 200629_at | 1.751 | 4.574 | 0.0000 | 0.0049 | 0.1273 |
| glucuronidase, beta pseudogene 11 | 213502_x_at | 1.732 | 4.515 | 0.0000 | 0.0060 | 0.1608 |
| chemokine (C-C motif) ligand 5 | 1405_i_at | 1.337 | 4.483 | 0.0000 | 0.0065 | 0.1824 |
| NA | 217378_x_at | 1.061 | 4.360 | 0.0000 | 0.0102 | 0.2964 |
| major histocompatibility complex, class II, DP alpha 1 | 211990_at | 1.624 | 4.325 | 0.0000 | 0.0113 | 0.3389 |
| torsin family 3, member A | 218459_at | 3.439 | 4.312 | 0.0000 | 0.0114 | 0.3568 |
| chemokine (C-C motif) ligand 5 | 204655_at | 1.361 | 4.305 | 0.0000 | 0.0114 | 0.3657 |
| immunoglobulin heavy constant mu | 209374_s_at | 0.867 | 4.275 | 0.0000 | 0.0125 | 0.4113 |
| low density lipoprotein receptor-related protein 4 | 212850_at | −1.191 | −4.247 | 0.0000 | 0.0134 | 0.4578 |
| chemokine (C—X—C motif) ligand 9 | 203915_at | 1.018 | 4.240 | 0.0000 | 0.0134 | 0.4696 |
| ATP-binding cassette, sub-family G (WHITE), member 2 (Junior blood group) | 209735_at | −1.225 | −4.221 | 0.0001 | 0.0139 | 0.5058 |
| immunoglobulin kappa constant | 216576_x_at | 0.943 | 4.217 | 0.0001 | 0.0139 | 0.5132 |
| major histocompatibility complex, class II, DQ beta 1 | 209823_x_at | 1.637 | 4.170 | 0.0001 | 0.0162 | 0.6138 |
| chemokine (C-C motif) ligand 4 | 204103_at | 1.851 | 4.147 | 0.0001 | 0.0172 | 0.6692 |
| immunoglobulin kappa constant | 214768_x_at | 0.901 | 4.131 | 0.0001 | 0.0178 | 0.7111 |
| immunoglobulin kappa constant | 217157_x_at | 1.317 | 4.072 | 0.0001 | 0.0216 | 0.8853 |
| NA | 216401_x_at | 1.015 | 4.042 | 0.0001 | 0.0235 | 0.9890 |
| hepatic leukemia factor | 204755_x_at | −0.941 | −4.022 | 0.0001 | 0.0246 | 1.0000 |
| cytochrome b-245, beta polypeptide | 203923_s_at | 1.840 | 4.018 | 0.0001 | 0.0246 | 1.0000 |
| DEAD (Asp-Glu-Ala-Asp) box helicase 24 | 200702_s_at | 3.153 | 4.009 | 0.0001 | 0.0249 | 1.0000 |
| immunoglobulin lambda joining 3 | 211798_x_at | 1.018 | 3.986 | 0.0001 | 0.0264 | 1.0000 |
| COP9 signalosome subunit 8 | 202143_s_at | −1.152 | −3.974 | 0.0001 | 0.0271 | 1.0000 |
| adhesion G protein-coupled receptor L3 | 209867_s_at | −0.973 | −3.961 | 0.0001 | 0.0273 | 1.0000 |
| collagen, type XVII, alpha 1 | 204636_at | −1.010 | −3.960 | 0.0001 | 0.0273 | 1.0000 |
| immunoglobulin heavy constant alpha 1 | 216510_x_at | 0.830 | 3.935 | 0.0001 | 0.0293 | 1.0000 |
| proteasome (prosome, macropain) subunit, alpha type, 6 | 208805_at | 2.918 | 3.930 | 0.0001 | 0.0293 | 1.0000 |
| major histocompatibility complex, class II, DM alpha | 217478_s_at | 1.619 | 3.901 | 0.0002 | 0.0315 | 1.0000 |
| immunoglobulin heavy locus | 217281_x_at | 1.050 | 3.899 | 0.0002 | 0.0315 | 1.0000 |
| tripartite motif containing 38 | 203567_s_at | 2.688 | 3.889 | 0.0002 | 0.0321 | 1.0000 |
| cathepsin C | 201487_at | 1.716 | 3.865 | 0.0002 | 0.0340 | 1.0000 |
| syndecan 2 | 212157_at | −0.762 | −3.863 | 0.0002 | 0.0340 | 1.0000 |
| follistatin | 207345_at | −1.130 | −3.858 | 0.0002 | 0.0340 | 1.0000 |
| jun D proto-oncogene | 203752_s_at | 2.487 | 3.849 | 0.0002 | 0.0345 | 1.0000 |
| chemokine (C—X—C motif) receptor 6 | 206974_at | 2.858 | 3.822 | 0.0002 | 0.0374 | 1.0000 |
| immunoglobulin lambda constant 1 (Mcg marker) | 217148_x_at | 0.914 | 3.815 | 0.0002 | 0.0375 | 1.0000 |
| clusterin-like 1 (retinal) | 206556_at | −0.917 | −3.812 | 0.0002 | 0.0375 | 1.0000 |
| apolipoprotein L, 6 | 219716_at | 2.452 | 3.796 | 0.0002 | 0.0382 | 1.0000 |
| interferon-induced protein 44-like | 204439_at | 0.948 | 3.795 | 0.0002 | 0.0382 | 1.0000 |
| immunoglobulin kappa constant | 211644_x_at | 0.787 | 3.793 | 0.0002 | 0.0382 | 1.0000 |
| KLF3 antisense RNA 1 | 219871_at | −1.061 | −3.779 | 0.0003 | 0.0386 | 1.0000 |
| immunoglobulin lambda variable 1-44 | 217227_x_at | 1.078 | 3.778 | 0.0003 | 0.0386 | 1.0000 |
| transporter 1, ATP-binding cassette, sub-family B (MDR/TAP) | 202307_s_at | 1.409 | 3.777 | 0.0003 | 0.0386 | 1.0000 |
| ubiquitin-conjugating enzyme E2L6 | 201649_at | 1.632 | 3.766 | 0.0003 | 0.0391 | 1.0000 |
| interferon-induced protein 44 | 214453_s_at | 1.088 | 3.760 | 0.0003 | 0.0391 | 1.0000 |
| major histocompatibility complex, class II, DQ beta 1 | 211656_x_at | 1.865 | 3.758 | 0.0003 | 0.0391 | 1.0000 |
| immunoglobulin kappa variable 1D-13 | 216207_x_at | 1.089 | 3.758 | 0.0003 | 0.0391 | 1.0000 |
| glutamyl aminopeptidase (aminopeptidase A) | 204845_s_at | −0.749 | −3.745 | 0.0003 | 0.0403 | 1.0000 |
| immunoglobulin heavy locus | 211868_x_at | 1.404 | 3.740 | 0.0003 | 0.0404 | 1.0000 |
| transformation/transcription domain-associated protein | 214908_s_at | −0.799 | −3.727 | 0.0003 | 0.0415 | 1.0000 |
| cyclin D2 | 200951_s_at | 2.747 | 3.714 | 0.0003 | 0.0415 | 1.0000 |
| guanylate binding protein 2, interferon-inducible | 202748_at | 1.536 | 3.711 | 0.0003 | 0.0415 | 1.0000 |
| signal transducer and activator of transcription 1, 91 kDa | AFFX-HUMIS | 1.535 | 3.708 | 0.0003 | 0.0415 | 1.0000 |

TABLE 35-continued

Summary of genes achieving selection criterion (corrected p-value < 0.05) in univariate analysis of all patients stratified on HER status

| | | | | | | |
|---|---|---|---|---|---|---|
| SR-related CTD-associated factor 11 | 213850_s_at | 2.848 | 3.707 | 0.0003 | 0.0415 | 1.0000 |
| signal transducer and activator of transcription 1, 91 kDa | 200887_s_at | 1.452 | 3.703 | 0.0003 | 0.0415 | 1.0000 |
| butyrophilin, subfamily 3, member A2 | 209846_s_at | 1.625 | 3.702 | 0.0003 | 0.0415 | 1.0000 |
| tryptophanyl-tRNA synthetase | 200628_s_at | 1.842 | 3.691 | 0.0004 | 0.0415 | 1.0000 |
| complement component 1, q subcomponent, A chain | 218232_at | 1.375 | 3.689 | 0.0004 | 0.0415 | 1.0000 |
| NA | 217480_x_at | 1.218 | 3.687 | 0.0004 | 0.0415 | 1.0000 |
| centrosomal protein 350 kDa | 213956_at | 2.623 | 3.683 | 0.0004 | 0.0415 | 1.0000 |
| FAT atypical cadherin 4 | 219427_at | −0.980 | −3.683 | 0.0004 | 0.0415 | 1.0000 |
| transportin 1 | 209225_x_at | 3.102 | 3.681 | 0.0004 | 0.0415 | 1.0000 |
| membrane associated guanylate kinase, WW and PDZ domain containing 2 | 209737_at | −0.725 | −3.679 | 0.0004 | 0.0415 | 1.0000 |
| ELL associated factor 2 | 219551_at | 2.091 | 3.679 | 0.0004 | 0.0415 | 1.0000 |
| hes-related family bHLH transcription factor with YRPW motif 1 | 44783_s_at | −0.553 | −3.674 | 0.0004 | 0.0415 | 1.0000 |
| odontogenic, ameloblast asssociated | 220133_at | −0.332 | −3.673 | 0.0004 | 0.0415 | 1.0000 |
| catenin (cadherin-associated protein), delta 2 | 209617_s_at | −0.761 | −3.660 | 0.0004 | 0.0424 | 1.0000 |
| carbonic anhydrase II | 209301_at | −0.361 | −3.660 | 0.0004 | 0.0424 | 1.0000 |
| immunoglobulin kappa locus | 211650_x_at | 1.028 | 3.651 | 0.0004 | 0.0433 | 1.0000 |
| immunoglobulin kappa locus | 214916_x_at | 1.014 | 3.645 | 0.0004 | 0.0435 | 1.0000 |
| dystonin | 216918_s_at | −0.816 | −3.644 | 0.0004 | 0.0435 | 1.0000 |
| butyrophilin, subfamily 3, member A3 | 204820_s_at | 1.682 | 3.638 | 0.0004 | 0.0436 | 1.0000 |
| immunoglobulin lambda joining 3 | 216984_x_at | 0.981 | 3.637 | 0.0004 | 0.0436 | 1.0000 |
| apolipoprotein B mRNA editing enzyme, catalytic polypeptide-like 3G | 204205_at | 1.762 | 3.622 | 0.0004 | 0.0451 | 1.0000 |
| peroxisomal biogenesis factor 1 | 215023_s_at | −0.633 | −3.622 | 0.0004 | 0.0451 | 1.0000 |
| interferon, gamma-inducible protein 16 | 208965_s_at | 1.301 | 3.607 | 0.0005 | 0.0464 | 1.0000 |
| interferon, gamma-inducible protein 16 | 206332_s_at | 1.264 | 3.606 | 0.0005 | 0.0464 | 1.0000 |
| immunoglobulin heavy constant alpha 1 | 211641_x_at | 1.418 | 3.603 | 0.0005 | 0.0464 | 1.0000 |
| butyrophilin, subfamily 3, member A3 | 204821_at | 2.227 | 3.601 | 0.0005 | 0.0464 | 1.0000 |
| fibroblast growth factor receptor 1 | 210973_s_at | −0.599 | −3.597 | 0.0005 | 0.0464 | 1.0000 |
| staufen double-stranded RNA binding protein 2 | 204226_at | −0.784 | −3.596 | 0.0005 | 0.0464 | 1.0000 |
| CD38 molecule | 205692_s_at | 1.835 | 3.590 | 0.0005 | 0.0468 | 1.0000 |
| interferon regulatory factor 9 | 203882_at | 1.956 | 3.583 | 0.0005 | 0.0476 | 1.0000 |
| butyrophilin, subfamily 3, member A3 | 38241_at | 1.911 | 3.577 | 0.0005 | 0.0479 | 1.0000 |
| interferon stimulated exonuclease gene 20 kDa | 204698_at | 1.456 | 3.576 | 0.0005 | 0.0479 | 1.0000 |
| NA | 217179_x_at | 0.984 | 3.570 | 0.0005 | 0.0485 | 1.0000 |
| tumor necrosis factor (ligand) superfamily, member 10 | 202688_at | 1.084 | 3.561 | 0.0005 | 0.0494 | 1.0000 |
| major histocompatibility complex, class II, DR beta 4 | 208306_x_at | 1.936 | 3.554 | 0.0006 | 0.0499 | 1.0000 |
| CD163 molecule | 203645_s_at | 1.419 | 3.551 | 0.0006 | 0.0499 | 1.0000 |
| hes-related family bHLH transcription factor with YRPW motif 1 | 218839_at | −0.652 | −3.550 | 0.0006 | 0.0499 | 1.0000 |

TABLE 36

Summary of genes achieving selection criterion (corrected p-value < 0.05) in multivariate analysis of triple negative patients

| GENENAME | PROBEID | ENTREZ ID | SYMBOL | Estimate | Std. Error | LCl |
|---|---|---|---|---|---|---|
| guanylate binding protein 1, interferon-inducible | 202269_x_at | 2633 | GBP1 | 0.927 | 0.1748 | 0.584 |
| chemokine (C—X—C motif) ligand 13 | 205242_at | 10563 | CXCL13 | 0.834 | 0.1583 | 0.523 |
| sulfotransferase family 1E, estrogen-preferring, member 1 | 219934_s_at | 6783 | SULT1E1 | −2.935 | 0.5679 | −4.048 |
| chemokine (C—X—C motif) ligand 10 | 204533_at | 3627 | CXCL10 | 0.938 | 0.1904 | 0.565 |
| immunoglobulin kappa constant | 221651_x_at | 3514 | IGKC | 1.117 | 0.2296 | 0.667 |
| immunoglobulin kappa constant | 221671_x_at | 3514 | IGKC | 1.104 | 0.2272 | 0.659 |
| immunoglobulin heavy constant gamma 3 (G3m marker) | 211430_s_at | 3502 | IGHG3 | 0.766 | 0.1588 | 0.455 |
| absent in melanoma 2 | 206513_at | 9447 | AIM2 | 1.554 | 0.3285 | 0.910 |
| SLAM family member 8 | 219386_s_at | 56833 | SLAMF8 | 1.372 | 0.2913 | 0.801 |
| chemokine (C-C motif) ligand 8 | 214038_at | 6355 | CCL8 | 0.875 | 0.1859 | 0.511 |
| immunoglobulin lambda joining 3 | 214677_x_at | 28831 | IGLJ3 | 0.752 | 0.1622 | 0.434 |
| immunoglobulin kappa constant | 215176_x_at | 3514 | IGKC | 0.690 | 0.1493 | 0.397 |
| immunoglobulin lambda constant 1 (Mcg marker) | 215121_x_at | 3537 | IGLC1 | 0.868 | 0.1883 | 0.499 |
| immunoglobulin lambda-like polypeptide 3, pseudogene | 215946_x_at | 91353 | IGLL3P | 1.199 | 0.2608 | 0.688 |
| immunoglobulin kappa constant | 214836_x_at | 3514 | IGKC | 1.049 | 0.2286 | 0.601 |
| hepatic leukemia factor | 204753_s_at | 3131 | HLF | −1.856 | 0.4061 | −2.652 |
| chemokine (C-C motif) ligand 5 | 1405_i_at | 6352 | CCL5 | 1.030 | 0.2259 | 0.587 |
| immunoglobulin lambda constant 1 (Mcg marker) | 209138_x_at | 3537 | IGLC1 | 0.785 | 0.1722 | 0.447 |

TABLE 36-continued

Summary of genes achieving selection criterion (corrected p-value < 0.05) in multivariate analysis of triple negative patients

| Gene Name | Probe ID | ID | Symbol | Val1 | Val2 | Val3 |
|---|---|---|---|---|---|---|
| signal transducer and activator of transcription 1, 91 kDa | 209969_s_at | 6772 | STAT1 | 1.060 | 0.2332 | 0.603 |
| immunoglobulin lambda variable cluster | 215379_x_at | 3546 | IGLV@ | 0.856 | 0.1883 | 0.486 |
| immunoglobulin kappa constant | 214669_x_at | 3514 | IGKC | 0.893 | 0.1974 | 0.506 |
| chemokine (C-C motif) ligand 5 | 204655_at | 6352 | CCL5 | 1.037 | 0.2357 | 0.575 |
| NA | 211645_x_at | NA | NA | 0.672 | 0.1529 | 0.372 |
| torsin family 3, member A | 218459_at | 64222 | TOR3A | 2.842 | 0.6473 | 1.573 |
| guanylate binding protein 1, interferon-inducible | 202270_at | 2633 | GBP1 | 0.831 | 0.1913 | 0.456 |
| chemokine (C—X—C motif) ligand 9 | 203915_at | 4283 | CXCL9 | 0.770 | 0.1793 | 0.418 |
| bromodomain adjacent to zinc finger domain, 1A | 217985_s_at | 11177 | BAZ1A | 1.934 | 0.4522 | 1.048 |
| post-GPI attachment to proteins 1 | 213469_at | 80055 | PGAP1 | −2.106 | 0.4973 | −3.081 |
| major histocompatibility complex, class II, DP alpha 1 | 211990_at | 3113 | HLA-DPA1 | 1.163 | 0.2748 | 0.625 |
| hepatic leukemia factor | 204754_at | 3131 | HLF | −2.195 | 0.5208 | −3.216 |
| tryptophanyl-tRNA synthetase | 200629_at | 7453 | WARS | 1.280 | 0.3046 | 0.683 |
| immunoglobulin heavy constant mu | 209374_s_at | 3507 | IGHM | 0.651 | 0.1552 | 0.347 |
| NA | 217378_x_at | NA | NA | 0.786 | 0.1904 | 0.412 |
| glucuronidase, beta pseudogene 11 | 213502_x_at | 91316 | GUSBP11 | 1.259 | 0.3083 | 0.655 |
| DEAD (Asp-Glu-Ala-Asp) box helicase 24 | 200702_s_at | 57062 | DDX24 | 2.272 | 0.5679 | 1.159 |
| interferon-induced protein 44-like | 204439_at | 10964 | IFI44L | 0.722 | 0.1830 | 0.364 |
| immunoglobulin kappa constant | 217157_x_at | 3514 | IGKC | 0.964 | 0.2453 | 0.483 |
| adhesion G protein-coupled receptor L3 | 209867_s_at | 23284 | ADGRL3 | −2.017 | 0.5145 | −3.025 |
| immunoglobulin kappa constant | 216576_x_at | 3514 | IGKC | 0.674 | 0.1720 | 0.337 |
| charged multivesicular body protein 2B | 202537_s_at | 25978 | CHMP2B | 1.773 | 0.4573 | 0.877 |
| mitochondrial assembly of ribosomal large subunit 1 | 203819_s_at | 115416 | MALSU1 | 0.907 | 0.2338 | 0.448 |

| GENENAME | PROBEID | HCl | t value | Pval | FDR | bonferroni |
|---|---|---|---|---|---|---|
| guanylate binding protein 1, interferon-inducible | 202269_x_at | 1.269 | 5.303 | 0.0000 | 0.0046 | 0.0079 |
| chemokine (C—X—C motif) ligand 13 | 205242_at | 1.144 | 5.266 | 0.0000 | 0.0046 | 0.0093 |
| sulfotransferase family 1E, estrogen-preferring, member 1 | 219934_s_at | −1.822 | −5.168 | 0.0000 | 0.0046 | 0.0139 |
| chemokine (C—X—C motif) ligand 10 | 204533_at | 1.311 | 4.926 | 0.0000 | 0.0080 | 0.0374 |
| immunoglobulin kappa constant | 221651_x_at | 1.567 | 4.864 | 0.0000 | 0.0080 | 0.0479 |
| immunoglobulin kappa constant | 221671_x_at | 1.549 | 4.860 | 0.0000 | 0.0080 | 0.0487 |
| immunoglobulin heavy constant gamma 3 (G3m marker) | 211430_s_at | 1.077 | 4.824 | 0.0000 | 0.0080 | 0.0562 |
| absent in melanoma 2 | 206513_at | 2.198 | 4.730 | 0.0000 | 0.0085 | 0.0819 |
| SLAM family member 8 | 219386_s_at | 1.943 | 4.708 | 0.0000 | 0.0085 | 0.0892 |
| chemokine (C-C motif) ligand 8 | 214038_at | 1.240 | 4.708 | 0.0000 | 0.0085 | 0.0892 |
| immunoglobulin lambda joining 3 | 214677_x_at | 1.070 | 4.637 | 0.0000 | 0.0085 | 0.1177 |
| immunoglobulin kappa constant | 215176_x_at | 0.982 | 4.618 | 0.0000 | 0.0085 | 0.1267 |
| immunoglobulin lambda constant 1 (Mcg marker) | 215121_x_at | 1.237 | 4.612 | 0.0000 | 0.0085 | 0.1299 |
| immunoglobulin lambda-like polypeptide 3, pseudogene | 215946_x_at | 1.711 | 4.598 | 0.0000 | 0.0085 | 0.1370 |
| immunoglobulin kappa constant | 214836_x_at | 1.497 | 4.591 | 0.0000 | 0.0085 | 0.1408 |
| hepatic leukemia factor | 204753_s_at | −1.060 | −4.569 | 0.0000 | 0.0085 | 0.1537 |
| chemokine (C-C motif) ligand 5 | 1405_i_at | 1.473 | 4.559 | 0.0000 | 0.0085 | 0.1596 |
| immunoglobulin lambda constant 1 (Mcg marker) | 209138_x_at | 1.122 | 4.557 | 0.0000 | 0.0085 | 0.1609 |
| signal transducer and activator of transcription 1, 91 kDa | 209969_s_at | 1.517 | 4.543 | 0.0000 | 0.0085 | 0.1695 |
| immunoglobulin lambda variable cluster | 215379_x_at | 1.225 | 4.543 | 0.0000 | 0.0085 | 0.1700 |
| immunoglobulin kappa constant | 214669_x_at | 1.280 | 4.523 | 0.0000 | 0.0087 | 0.1836 |
| chemokine (C-C motif) ligand 5 | 204655_at | 1.499 | 4.399 | 0.0000 | 0.0127 | 0.2944 |
| NA | 211645_x_at | 0.972 | 4.394 | 0.0000 | 0.0127 | 0.3006 |
| torsin family 3, member A | 218459_at | 4.110 | 4.390 | 0.0000 | 0.0127 | 0.3049 |
| guanylate binding protein 1, interferon-inducible | 202270_at | 1.206 | 4.341 | 0.0000 | 0.0147 | 0.3674 |
| chemokine (C—X—C motif) ligand 9 | 203915_at | 1.121 | 4.291 | 0.0000 | 0.0170 | 0.4427 |
| bromodomain adjacent to zinc finger domain, 1A | 217985_s_at | 2.820 | 4.278 | 0.0000 | 0.0172 | 0.4654 |
| post-GPI attachment to proteins 1 | 213469_at | −1.131 | −4.234 | 0.0001 | 0.0190 | 0.5474 |
| major histocompatibility complex, class II, DP alpha 1 | 211990_at | 1.702 | 4.233 | 0.0001 | 0.0190 | 0.5498 |
| hepatic leukemia factor | 204754_at | −1.174 | −4.214 | 0.0001 | 0.0196 | 0.5897 |
| tryptophanyl-tRNA synthetase | 200629_at | 1.877 | 4.204 | 0.0001 | 0.0196 | 0.6133 |
| immunoglobulin heavy constant mu | 209374_s_at | 0.955 | 4.197 | 0.0001 | 0.0196 | 0.6283 |
| NA | 217378_x_at | 1.159 | 4.127 | 0.0001 | 0.0247 | 0.8140 |
| glucuronidase, beta pseudogene 11 | 213502_x_at | 1.863 | 4.084 | 0.0001 | 0.0279 | 0.9491 |
| DEAD (Asp-Glu-Ala-Asp) box helicase 24 | 200702_s_at | 3.385 | 4.001 | 0.0001 | 0.0367 | 1.0000 |
| interferon-induced protein 44-like | 204439_at | 1.081 | 3.948 | 0.0002 | 0.0431 | 1.0000 |
| immunoglobulin kappa constant | 217157_x_at | 1.444 | 3.928 | 0.0002 | 0.0440 | 1.0000 |
| adhesion G protein-coupled receptor L3 | 209867_s_at | −1.009 | −3.920 | 0.0002 | 0.0440 | 1.0000 |
| immunoglobulin kappa constant | 216576_x_at | 1.012 | 3.920 | 0.0002 | 0.0440 | 1.0000 |
| charged multivesicular body protein 2B | 202537_s_at | 2.669 | 3.877 | 0.0002 | 0.0487 | 1.0000 |
| mitochondrial assembly of ribosomal large subunit 1 | 203819_s_at | 1.365 | 3.877 | 0.0002 | 0.0487 | 1.0000 |

TABLE 37

Summary of genes achieving selection criterion (corrected p-value < 0.05) in multivariate analysis of all patients stratified on HER status

| GENENAME | PROBE ID | ENTREZ ID | SYMBOL | Estimate | Std. Error | LCl |
|---|---|---|---|---|---|---|
| guanylate binding protein 1, interferon-inducible | 202269_x_at | 2633 | GBP1 | 0.900 | 0.1634 | 0.579 |
| sulfotransferase family 1E, estrogen-preferring, member 1 | 219934_s_at | 6783 | SULT1E1 | −2.747 | 0.5217 | −3.769 |
| chemokine (C—X—C motif) ligand 10 | 204533_at | 3627 | CXCL10 | 0.899 | 0.1783 | 0.550 |
| immunoglobulin heavy constant gamma 3 (G3m marker) | 211430_s_at | 3502 | IGHG3 | 0.736 | 0.1468 | 0.449 |
| chemokine (C—X—C motif) ligand 13 | 205242_at | 10563 | CXCL13 | 0.718 | 0.1439 | 0.436 |
| chemokine (C-C motif) ligand 8 | 214038_at | 6355 | CCL8 | 0.838 | 0.1724 | 0.500 |
| immunoglobulin kappa constant | 221651_x_at | 3514 | IGKC | 1.036 | 0.2134 | 0.618 |
| immunoglobulin kappa constant | 221671_x_at | 3514 | IGKC | 1.023 | 0.2115 | 0.609 |
| SLAM family member 8 | 219386_s_at | 56833 | SLAMF8 | 1.335 | 0.2759 | 0.794 |
| immunoglobulin lambda joining 3 | 214677_x_at | 28831 | IGLJ3 | 0.714 | 0.1490 | 0.422 |
| immunoglobulin lambda constant 1 (Mcg marker) | 215121_x_at | 3537 | IGLC1 | 0.829 | 0.1735 | 0.489 |
| immunoglobulin lambda-like polypeptide 3, pseudogene | 215946_x_at | 91353 | IGLL3P | 1.123 | 0.2376 | 0.658 |
| absent in melanoma 2 | 206513_at | 9447 | AIM2 | 1.483 | 0.3136 | 0.868 |
| guanylate binding protein 1, interferon-inducible | 202270_at | 2633 | GBP1 | 0.843 | 0.1786 | 0.493 |
| immunoglobulin lambda constant 1 (Mcg marker) | 209138_x_at | 3537 | IGLC1 | 0.744 | 0.1580 | 0.434 |
| immunoglobulin lambda variable cluster | 215379_x_at | 3546 | IGLV@ | 0.813 | 0.1731 | 0.474 |
| signal transducer and activator of transcription 1, 91 kDa | 209969_s_at | 6772 | STAT1 | 1.023 | 0.2188 | 0.594 |
| bromodomain adjacent to zinc finger domain, 1A | 217985_s_at | 11177 | BAZ1A | 2.001 | 0.4293 | 1.160 |
| immunoglobulin kappa constant | 214836_x_at | 3514 | IGKC | 0.981 | 0.2109 | 0.568 |
| hepatic leukemia factor | 204753_s_at | 3131 | HLF | −1.767 | 0.3800 | −2.512 |
| immunoglobulin kappa constant | 215176_x_at | 3514 | IGKC | 0.625 | 0.1351 | 0.360 |
| immunoglobulin kappa constant | 214669_x_at | 3514 | IGKC | 0.830 | 0.1806 | 0.476 |
| post-GPI attachment to proteins 1 | 213469_at | 80055 | PGAP1 | −2.146 | 0.4672 | −3.061 |
| hepatic leukemia factor | 204754_at | 3131 | HLF | −2.236 | 0.4954 | −3.207 |
| tryptophanyl-tRNA synthetase | 200629_at | 7453 | WARS | 1.238 | 0.2774 | 0.695 |
| NA | 211645_x_at | NA | NA | 0.616 | 0.1385 | 0.345 |
| chemokine (C—X—C motif) ligand 9 | 203915_at | 4283 | CXCL9 | 0.708 | 0.1655 | 0.384 |
| ATP-binding cassette, sub-family G (WHITE), member 2 (Junior blood group) | 209735_at | 9429 | ABCG2 | −2.461 | 0.5777 | −3.593 |
| chemokine (C-C motif) ligand 5 | 1405_i_at | 6352 | CCL5 | 0.892 | 0.2115 | 0.478 |
| glucuronidase, beta pseudogene 11 | 213502_x_at | 91316 | GUSBP11 | 1.151 | 0.2746 | 0.612 |
| major histocompatibility complex, class II, DP alpha 1 | 211990_at | 3113 | HLA-DPA1 | 1.095 | 0.2620 | 0.582 |
| NA | 217378_x_at | NA | NA | 0.717 | 0.1724 | 0.379 |
| major histocompatibility complex, class II, DQ beta 1 | 209823_x_at | 3119 | HLA-DQB1 | 1.117 | 0.2702 | 0.587 |
| chemokine (C-C motif) ligand 5 | 204655_at | 6352 | CCL5 | 0.906 | 0.2213 | 0.472 |
| low density lipoprotein receptor-related protein 4 | 212850_s_at | 4038 | LRP4 | −2.167 | 0.5297 | −3.205 |
| chemokine (C-C motif) ligand 4 | 204103_at | 6351 | CCL4 | 1.269 | 0.3119 | 0.657 |
| immunoglobulin heavy constant mu | 209374_s_at | 3507 | IGHM | 0.576 | 0.1420 | 0.298 |
| cytochrome b-245, beta polypeptide | 203923_s_at | 1536 | CYBB | 1.247 | 0.3101 | 0.639 |
| immunoglobulin kappa constant | 214768_x_at | 3514 | IGKC | 0.608 | 0.1519 | 0.310 |
| immunoglobulin kappa constant | 216576_x_at | 3514 | IGKC | 0.624 | 0.1566 | 0.317 |

TABLE 37-continued

Summary of genes achieving selection criterion (corrected p-value < 0.05) in multivariate analysis of all patients stratified on HER status

| | | | | | | |
|---|---|---|---|---|---|---|
| proteasome (prosome, macropain) subunit, alpha type, 6 | 208805_at | 5687 | PSMA6 | 2.007 | 0.5088 | 1.010 |
| immunoglobulin kappa constant | 217157_x_at | 3514 | IGKC | 0.867 | 0.2219 | 0.432 |
| charged multivesicular body protein 2B | 202537_s_at | 25978 | CHMP2B | 1.659 | 0.4264 | 0.824 |
| torsin family 3, member A | 218459_at | 64222 | TOR3A | 2.295 | 0.5920 | 1.135 |
| guanylate binding protein 2, interferon-inducible | 202748_at | 2634 | GBP2 | 1.053 | 0.2727 | 0.519 |
| NA | 216401_x_at | NA | NA | 0.667 | 0.1728 | 0.328 |
| immunoglobulin lambda joining 3 | 211798_x_at | 28831 | IGLJ3 | 0.667 | 0.1732 | 0.327 |
| collagen, type XVII, alpha 1 | 204636_at | 1308 | COL17A1 | −2.046 | 0.5370 | −3.099 |
| DEAD (Asp-Glu-Ala-Asp) box helicase 24 | 200702_s_at | 57062 | DDX24 | 2.053 | 0.5392 | 0.996 |
| hepatic leukemia factor | 204755_x_at | 3131 | HLF | −1.812 | 0.4759 | −2.744 |
| perilipin 2 | 209122_at | 123 | PLIN2 | 1.061 | 0.2788 | 0.515 |
| cathepsin C | 201487_at | 1075 | CTSC | 1.150 | 0.3023 | 0.558 |
| immunoglobulin heavy constant alpha 1 | 216510_x_at | 3493 | IGHA1 | 0.547 | 0.1437 | 0.265 |
| adhesion G protein-coupled receptor L3 | 209867_s_at | 23284 | ADGRL3 | −1.890 | 0.4968 | −2.863 |
| mitochondrial assembly of ribosomal large subunit 1 | 203819_s_at | 115416 | MALSU1 | 0.841 | 0.2213 | 0.408 |
| FAT atypical cadherin 4 | 219427_at | 79633 | FAT4 | −2.190 | 0.5779 | −3.322 |
| carbonic anhydrase II | 209301_at | 760 | CA2 | −0.810 | 0.2137 | −1.228 |
| major histocompatibility complex, class II, DM alpha | 217478_s_at | 3108 | HLA-DMA | 1.051 | 0.2793 | 0.503 |
| immunoglobulin heavy locus | 217281_x_at | 3492 | IGH | 0.683 | 0.1819 | 0.327 |
| clusterin-like 1 (retinal) | 206556_at | 27098 | CLUL1 | −1.898 | 0.5058 | −2.890 |

| GENENAME | PROBE ID | HCl | t value | Pval | FDR | bonferroni |
|---|---|---|---|---|---|---|
| guanylate binding protein 1, interferon-inducible | 202269_x_at | 1.220 | 5.507 | 0.0000 | 0.0027 | 0.0027 |
| sulfotransferase family 1E, estrogen-preferring, member 1 | 219934_s_at | −1.724 | −5.265 | 0.0000 | 0.0038 | 0.0076 |
| chemokine (C—X—C motif) ligand 10 | 204533_at | 1.248 | 5.043 | 0.0000 | 0.0048 | 0.0195 |
| immunoglobulin heavy constant gamma 3 (G3m marker) | 211430_s_at | 1.024 | 5.016 | 0.0000 | 0.0048 | 0.0218 |
| chemokine (C—X—C motif) ligand 13 | 205242_at | 1.000 | 4.991 | 0.0000 | 0.0048 | 0.0242 |
| chemokine (C-C motif) ligand 8 | 214038_at | 1.176 | 4.859 | 0.0000 | 0.0049 | 0.0419 |
| immunoglobulin kappa constant | 221651_x_at | 1.454 | 4.854 | 0.0000 | 0.0049 | 0.0427 |
| immunoglobulin kappa constant | 221671_x_at | 1.438 | 4.839 | 0.0000 | 0.0049 | 0.0455 |
| SLAM family member 8 | 219386_s_at | 1.875 | 4.837 | 0.0000 | 0.0049 | 0.0458 |
| immunoglobulin lambda joining 3 | 214677_x_at | 1.006 | 4.793 | 0.0000 | 0.0049 | 0.0549 |
| immunoglobulin lambda constant 1 (Mcg marker) | 215121_x_at | 1.169 | 4.780 | 0.0000 | 0.0049 | 0.0578 |
| immunoglobulin lambda-like polypeptide 3, pseudogene | 215946_x_at | 1.589 | 4.729 | 0.0000 | 0.0049 | 0.0712 |
| absent in melanoma 2 | 206513_at | 2.098 | 4.729 | 0.0000 | 0.0049 | 0.0713 |
| guanylate binding protein 1, interferon-inducible | 202270_at | 1.193 | 4.720 | 0.0000 | 0.0049 | 0.0738 |
| immunoglobulin lambda constant 1 (Mcg marker) | 209138_x_at | 1.053 | 4.707 | 0.0000 | 0.0049 | 0.0777 |
| immunoglobulin lambda variable cluster | 215379_x_at | 1.153 | 4.699 | 0.0000 | 0.0049 | 0.0805 |
| signal transducer and activator of transcription 1, 91 kDa | 209969_s_at | 1.452 | 4.675 | 0.0000 | 0.0049 | 0.0884 |
| bromodomain adjacent to zinc finger domain, 1A | 217985_s_at | 2.843 | 4.662 | 0.0000 | 0.0049 | 0.0932 |
| immunoglobulin kappa constant | 214836_x_at | 1.394 | 4.650 | 0.0000 | 0.0049 | 0.0977 |
| hepatic leukemia factor | 204753_s_at | −1.022 | −4.649 | 0.0000 | 0.0049 | 0.0984 |
| immunoglobulin kappa constant | 215176_x_at | 0.890 | 4.627 | 0.0000 | 0.0051 | 0.1073 |
| immunoglobulin kappa constant | 214669_x_at | 1.184 | 4.594 | 0.0000 | 0.0054 | 0.1223 |

TABLE 37-continued

Summary of genes achieving selection criterion (corrected p-value < 0.05) in multivariate analysis of all patients stratified on HER status

| | | | | | | |
|---|---|---|---|---|---|---|
| post-GPI attachment to proteins 1 | 213469_at | −1.230 | −4.592 | 0.0000 | 0.0054 | 0.1232 |
| hepatic leukemia factor | 204754_at | −1.265 | −4.514 | 0.0000 | 0.0070 | 0.1680 |
| tryptophanyl-tRNA synthetase | 200629_at | 1.782 | 4.464 | 0.0000 | 0.0082 | 0.2047 |
| NA | 211645_x_at | 0.888 | 4.449 | 0.0000 | 0.0084 | 0.2172 |
| chemokine (C—X—C motif) ligand 9 | 203915_at | 1.032 | 4.277 | 0.0000 | 0.0156 | 0.4210 |
| ATP-binding cassette, sub-family G (WHITE), member 2 (Junior blood group) | 209735_at | −1.329 | −4.261 | 0.0000 | 0.0160 | 0.4489 |
| chemokine (C-C motif) ligand 5 | 1405_i_at | 1.307 | 4.218 | 0.0001 | 0.0182 | 0.5269 |
| glucuronidase, beta pseudogene 11 | 213502_x_at | 1.689 | 4.191 | 0.0001 | 0.0195 | 0.5853 |
| major histocompatibility complex, class II, DP alpha 1 | 211990_at | 1.609 | 4.180 | 0.0001 | 0.0196 | 0.6084 |
| NA | 217378_x_at | 1.055 | 4.158 | 0.0001 | 0.0207 | 0.6626 |
| major histocompatibility complex, class II, DQ beta 1 | 209823_x_at | 1.646 | 4.132 | 0.0001 | 0.0221 | 0.7278 |
| chemokine (C-C motif) ligand 5 | 204655_at | 1.339 | 4.093 | 0.0001 | 0.0243 | 0.8423 |
| low density lipoprotein receptor-related protein 4 | 212850_s_at | −1.129 | −4.091 | 0.0001 | 0.0243 | 0.8491 |
| chemokine (C-C motif) ligand 4 | 204103_at | 1.880 | 4.067 | 0.0001 | 0.0257 | 0.9271 |
| immunoglobulin heavy constant mu | 209374_s_at | 0.855 | 4.060 | 0.0001 | 0.0257 | 0.9517 |
| cytochrome b-245, beta polypeptide | 203923_s_at | 1.855 | 4.020 | 0.0001 | 0.0290 | 1.0000 |
| immunoglobulin kappa constant | 214768_x_at | 0.905 | 3.999 | 0.0001 | 0.0306 | 1.0000 |
| immunoglobulin kappa constant | 216576_x_at | 0.931 | 3.982 | 0.0001 | 0.0317 | 1.0000 |
| proteasome (prosome, macropain) subunit, alpha type, 6 | 208805_at | 3.005 | 3.946 | 0.0001 | 0.0353 | 1.0000 |
| immunoglobulin kappa constant | 217157_x_at | 1.302 | 3.905 | 0.0002 | 0.0399 | 1.0000 |
| charged multivesicular body protein 2B | 202537_s_at | 2.495 | 3.892 | 0.0002 | 0.0409 | 1.0000 |
| torsin family 3, member A | 218459_at | 3.455 | 3.877 | 0.0002 | 0.0422 | 1.0000 |
| guanylate binding protein 2, interferon-inducible | 202748_at | 1.588 | 3.862 | 0.0002 | 0.0431 | 1.0000 |
| NA | 216401_x_at | 1.006 | 3.858 | 0.0002 | 0.0431 | 1.0000 |
| immunoglobulin lambda joining 3 | 211798_x_at | 1.006 | 3.851 | 0.0002 | 0.0434 | 1.0000 |
| collagen, type XVII, alpha 1 | 204636_at | −0.994 | −3.811 | 0.0002 | 0.0441 | 1.0000 |
| DEAD (Asp-Glu-Ala-Asp) box helicase 24 | 200702_s_at | 3.109 | 3.807 | 0.0002 | 0.0441 | 1.0000 |
| hepatic leukemia factor | 204755_x_at | −0.879 | −3.806 | 0.0002 | 0.0441 | 1.0000 |
| perilipin 2 | 209122_at | 1.608 | 3.806 | 0.0002 | 0.0441 | 1.0000 |
| cathepsin C | 201487_at | 1.743 | 3.806 | 0.0002 | 0.0441 | 1.0000 |
| immunoglobulin heavy constant alpha 1 | 216510_x_at | 0.828 | 3.805 | 0.0002 | 0.0441 | 1.0000 |
| adhesion G protein-coupled receptor L3 | 209867_s_at | −0.916 | −3.804 | 0.0002 | 0.0441 | 1.0000 |
| mitochondrial assembly of ribosomal large subunit 1 | 203819_s_at | 1.275 | 3.802 | 0.0002 | 0.0441 | 1.0000 |
| FAT atypical cadherin 4 | 219427_at | −1.057 | −3.789 | 0.0003 | 0.0446 | 1.0000 |
| carbonic anhydrase II | 209301_at | −0.391 | −3.788 | 0.0003 | 0.0446 | 1.0000 |
| major histocompatibility complex, class II, DM alpha | 217478_s_at | 1.598 | 3.762 | 0.0003 | 0.0479 | 1.0000 |
| immunoglobulin heavy locus | 217281_x_at | 1.040 | 3.758 | 0.0003 | 0.0479 | 1.0000 |
| clusterin-like 1 (retinal) | 206556_at | −0.907 | −3.753 | 0.0003 | 0.0479 | 1.0000 |

TABLE 38

One-to-one mapping from gene to 'best' probe sets using 'jetset' package

| Platform | Series | GBP1 | HLF | CXCL13 |
|---|---|---|---|---|
| HG-U133A | GSE25066 GSE20271 GSE20194 GSE22093 GSE23988 | 202270_at | 204754_at | 205242_at |

TABLE 38-continued

| One-to-one mapping from gene to 'best' probe sets using 'jetset' package | | | | |
|---|---|---|---|---|
| HG-U133_Plus_2 | GSE16446 | 202270_at | 204754_at | 205242_at |
| U133-X3P | GSE6861 | g12803662_3p_a_at | Hs.250692.0.S4_3p_at | g5453576_3p_at |
| Platform | Series | LRRC23 | SULTIEI | IGKC |
| HG-U133A | GSE25066 | 206076_at | 219934_s_at | 211644_x_at |
|  | GSE20271 | | | |
|  | GSE20194 | | | |
|  | GSE22093 | | | |
|  | GSE23988 | | | |
| HG-U133_Plus_2 | GSE16446 | 206076_at | 222940_at | 211644_x_at |
| U133-X3P | GSE6861 | g5901897_3p_at | Hs.54576.0.S2_3p_at | 214669_3p_x_at |

Association Between the Four-Gene Signature and Stromal TILs

To assess the prognostic value of the four-gene signature on stromal TILs (Box-cox-transformed), we applied a general linear model for the response variable stromal TIL on the four-gene signature and the clinical covariates series (TOP vs. MDACC), age (continuous), cT (0-1-2 vs. 3-4), cN (0 vs. +) and grade (1-2 vs. 3). Results of the general linear model are shown in Table 39.

TABLE 39

General linear model with nonlinear effects - (Box-cox-transformed) Stromal TILs - 4-gene signature

|  | Coefficient | 95% IC | P |
|---|---|---|---|
| Age | 0.00 | −0.03-0.04 | 0.800 |
| cT | | | 0.186 |
| T3-4 vs. T0-1-2 | −0.62 | −1.54-0.30 | |
| cN | | | 0.593 |
| N+ vs. N0 | −0.25 | −1.17-0.67 | |
| Grade | | | 0.299 |
| 3 vs. 1-2 | 0.59 | −0.53-1.71 | |
| 4-gene signature | 6.53 | 4.59-8.48 | <0.001 |
| 4-gene signature - Non linear | −3.18 | −6.13-−0.22 | 0.035 |
| Series | | | 0.770 |
| MDACC vs. Bordet | 0.14 | −0.82-1.10 | |

Figure 45:
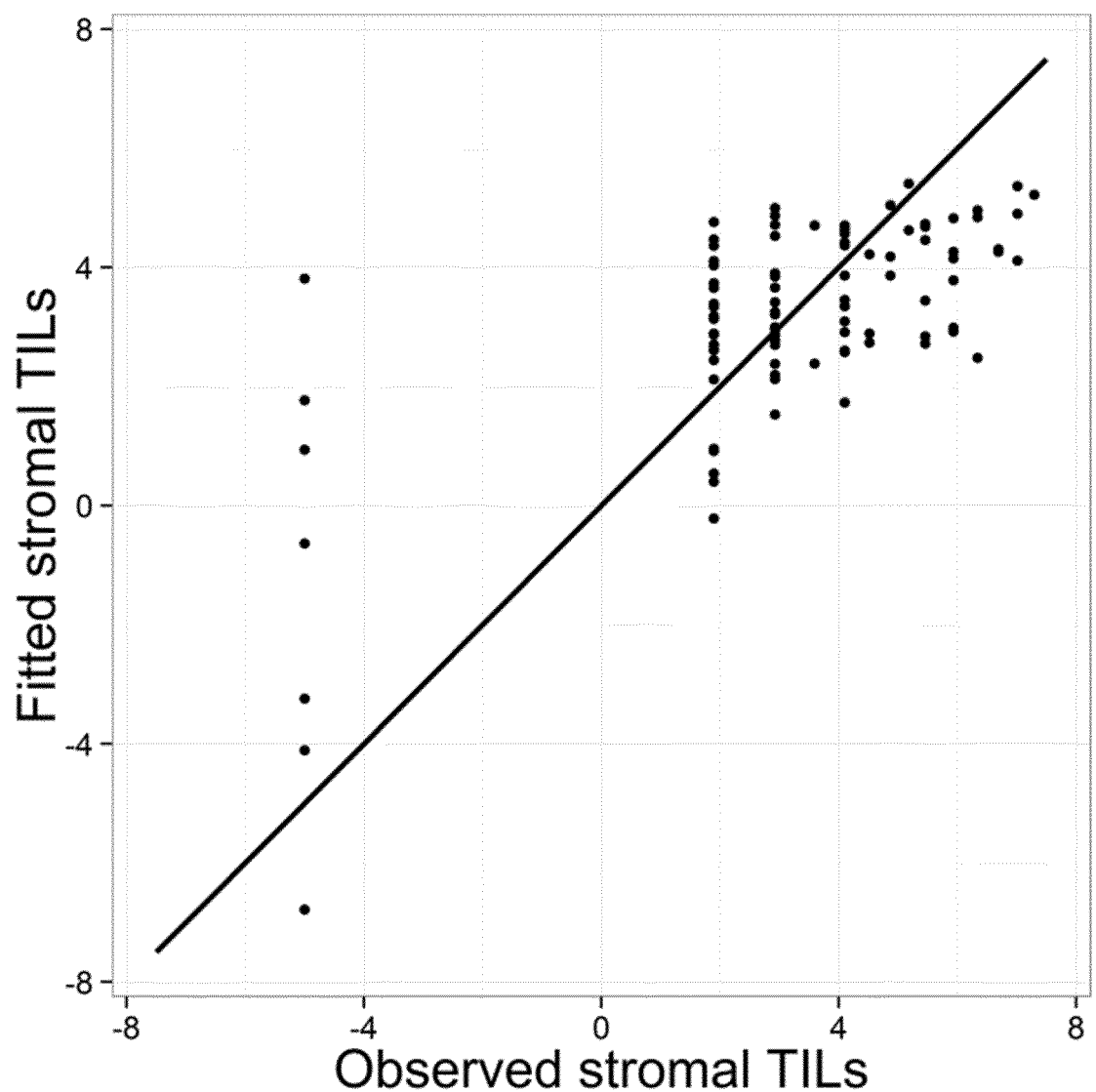

We used restricted cubic splines with 2 degrees of freedom to investigate the non-linear association between stromal TILs and the 4-gene signature. The non-linear effect was found significant. Plot of fitted stromal TILs (Box-cox-transformed) vs. observed stromal TILs (Box-cox-transformed) is shown in FIG. 45.

We computed the root mean squared prediction error (RMSE) using 1 000 repetitions of a ten-fold cross validation in the following way; the training dataset is first randomly split into ten previously obtained blocks of approximately equal size. Each of the ten data blocks is left out once to fit the model, and predictions are computed for the observations in the left-out block with the predict method of the fitted model. Thus, a prediction is obtained for each observation. The observed stromal TILs value and the obtained predictions for all observations are then passed to the prediction loss function cost (RMSE) to estimate the prediction error. This process is replicated 1 000 times and the estimated prediction errors from all replications as well as their average are estimated.

Assessing the Association Between the Four-Gene Signature and Pathological Complete Response in the Validation Set We explored the association between the probability to achieve pathological complete response (pCR) and the four-gene signature in the validation data set, we computed odds ratios (ORs) and 95% CI using a conditional logistic model that included the four-gene signature and the clinical covariates: age (continuous), cT (0-1-2 vs. 3-4), cN (0 vs. +) and grade (1-2 vs. 3) and was stratified on series (TOP vs. MDACC). Results of the conditional logistic model are shown in Table 40.

TABLE 40

Results of the conditional logistic regression assessing the association between the probability to achieve pathological complete response and the four-gene signature

|  | OR | 95% IC | P |
|---|---|---|---|
| Age | 0.98 | 0.95-1.02 | 0.344 |
| cT | | | 0.131 |
| T0-1-2 | 1 | | |
| T3-4 | 0.55 | 0.26-1.19 | |
| cN | | | 0.758 |
| N0 | 1 | | |
| N+ | 0.88 | 0.39-1.99 | |
| Grade | | | 0.046 |
| 1-2 | 1 | | |
| 3 | 3.43 | 1.02-11.48 | |
| One-unit increase in the four-gene signature | 0.96 | 0.30-3.08 | 0.947 | cT, clinical tumor size;
cN, clinical nodal status;
OR, Odds ratio;
CI, confidence interval;
P, p-value.

Univariate Selection (Including One Gene at a Time) with Correction for Multiple Comparisons (Secondary Analysis)

The univariate selection with correction for multiple comparisons procedure includes three steps:

1. To fit a general linear model to model the continuous level of Stromal TILs in the post chemotherapy samples using complete cases. Stromal TILs is transformed using Box-Cox transformation.
2. To correct for multiple comparisons using False Discovery Rate (FDR) method (Bonferroni p-values are reported for information purposes only).
3. To report genes that achieved the selection criterion of a corrected p-value <0-05.

TABLE 41

Summary of univariate selection with correction for multiple comparisons

| | TNBC n = 99 | | All patients n = 113 | |
| --- | --- | --- | --- | --- |
| | Without adjustment | With adjustment | Without adjustment | With adjustment |
| Variables included in addition to the gene expression | | | | |
| Series (TOP vs. MDACC) | X | X | X | X |
| HER2 status (Negative vs. Positive) | | | X | X |
| Age (continuous) | | X | | X |
| cT (0-1-2 vs. 3-4) | | X | | X |
| cN (0 vs. +) | | X | | X |
| Grade (1-2 vs. 3) | | X | | X |
| Number of genes achieving selection criterion† | 79 | 41 | 114 | 60 |
| Results table | Table A13 | Table A14 | Table A15 | Table A16 |

TNBC, Triple Negative Breast Cancer.
†corrected p-value < 0.05

EXAMPLE

The starting biological material is a sample from patient having a TNBC, such as as tumor biopsy, fine needle aspiration or blood sample.

Said sample is taken before any treatment.

mRNA are extracted from said sample by well-known technics by a person skilled in the art.

These mRNA are used to quantify the expression of the 4 genes GBP1, HLF, CXCL13 and SULT1E1 by a RT-PCR technic or similar technics, using 4 pairs of primers corresponding to the 4 genes of interest.

At least one housekeeping gene selected from the group comprising 18S rRNA, ACTB, HPRT1, HSPCB, PPIA, PUM1, RPS13, SDHA and TBP, is used to performed RT-PCR.

The measured expressions of the 4 genes GBP1, HLF, CXCL13 and SULT1E1 are then incorporated in the following equation in order to obtain the genomic predictor:

Genomic predictor=0.288*GBP1 expression+ 0.392*CXCL13 expression −1.027*HLF expression −1.726*SULT1E1 expression Coefficients applied to each of the gene expressions have been determined according to Table 5.

A distant relapse free and overall survival probability is calculated based on an equation that integrates the expression measurements of the 4 genes through the genomic predictor and the patient clinicopathological characteristics such as age, tumour size, tumour grade and tumour stage.

If the predicted survival probabilities are deemed high enough by the treating physician, the patient will receive a NACT.

If the predicted survival probabilities are deemed too low enough by the treating physician, the patient will receive more aggressive treatments (that can either by new experimental treatments in clinical trials or established therapy regimens for early breast cancer).

Another Aspect of the Invention is the Study of HLF (Hepatic Leukemia Factor) Gene.

As previously shown by our unit, treatment with chemotherapeutic agents induced an antitumor immune response in TNBC and this high infiltration with TILs was connected to favourable outcome (Dieci et al., 2014). By large scale study, the prognostic role of TILs in early TNBC patients was confirmed, since the ten-year overall survival rates were 89% and 68% for TNBC with high TILs and low TILs, respectively (Dieci et al., 2015). Another study, performed on primary TNBC patients of international FinHER trial, showed high TIL levels at a time of diagnosis associated with decreased distant recurrence rates (Loi et al., 2014).

In our group, in order to develop a genomic predictor of TILs after neoadjuvant ChT and to validate the possible prognostic value of this tool, post-ChT levels of TILs were quantified in series of TNBC patients that did not achieve pathological complete remission after surgery, and for which a genomic profile was already available. For the analysis, TILs have been evaluated after ChT in 113 samples from TNBC patients; 44 samples from TOP trial of Institut Jules Bordet (Brussels, Belgium) and 69 samples from MD Anderson Cancer Center (Houston, Tex., USA) series. Our biostaticians proceeded to model the continuous level of stromal TILs in the post-ChT samples as a function of gene expression. Analyses led to the selection of four genes sharing a triggered gene expression levels in connection to high stromal TILs. One of these signature genes is HLF (Hepatic Leukemia Factor) that was found in negative relation with stromal TILs presence. In other words, the increasing HLF expression levels within tumor cells decreased the presence of stromal TILs and probably the lymphocytic infiltration in tumor in general.

Gene HLF is located on chromosome 17 (17q22), encodes for proline and acidic-rich (PAR) protein family member, and represents a bZIP (basic leucine zipper) transcription factor, as DBP (Albumin D Box-Binding Protein) and TEF (Thyrotrophic Embryonic Factor). Gene HLF was originally identified in a chromosomal translocation with the gene E2A, linked to acute lymphoblastic leukemia (ALL) (Inaba et al., 1992). This led to its aberrant expression as a fusion protein (E2A-HLF), and to a form of ALL connected to poor prognosis due to the resistance to ChT (Jabbour et al., 2015).

However, high impact was given to HLF in connection to circadian rhythms and the mammalian timing system. Transcription factor HLF, as one of the PAR bZIP proteins involved in circadian behaviour, is a regulatory protein that clearly varies with high amplitudes during circadian rhythms and is accepted as an output regulator of this process. The circadian genes have been implicated in the regulation of cell cycle, stress response and drug toxicity (Waters et al., 2013).

The chronotherapy and circadian rhythms consideration in cancer and metabolism will probably play more important role in drug development and therapeutic efficacy (Ferrell and Chiang, 2015). The potential importance of HLF functional analyses in cancer is underlined by certain studies of fatigue-related safety issues and shift work impact on human body. The rotating night shift work has been associated with increased risk of breast carcinoma (Schernhammer et al., 2001). Additionally, in the example of colon cancer, the improved chronopharmacology in 5-fluorouracil night time administration reduced the therapy toxicity and improved the tumor size reduction (L6vi et al., 2001).

It has been shown that HLF regulates the expression of numerous genes involved in the metabolism of endobiotics and xenobiotics (Gachon et al., 2006). In this study, mouse models with PAR bZIP proteins triple knock-out (for Hlf, Dbp and Tef genes) were hypersensitive to xenobiotics and their early aging was detected as a consequence of the deficiency in xenobiotics detoxification properties. Recent studies with knock-out mice deficient in both alleles of mouse HLF showed that HSCs in these mice become more sensitive to 5-fluorouracil and that HLF is essential for maintaining the function of HSCs (Komorowska et al., 2015). Furthermore, the literature-based data are clearly connecting the HLF expression in cancer with reduced tumor cells apoptosis and improved cancer cell survival (Waters et al., 2013).

Given these previously published data, we decided to focus on HLF functional analysis, in order to study the role of the post-ChT lymphocytic attraction within tumor. For this objective, we decided to downregulate the expression of HLF in TNBC cell lines. Cells used for siHLF experiments were chosen according to literature-based data of HLF expression levels in various available BC cell lines (Kao et al., 2009).

Figure 41A:
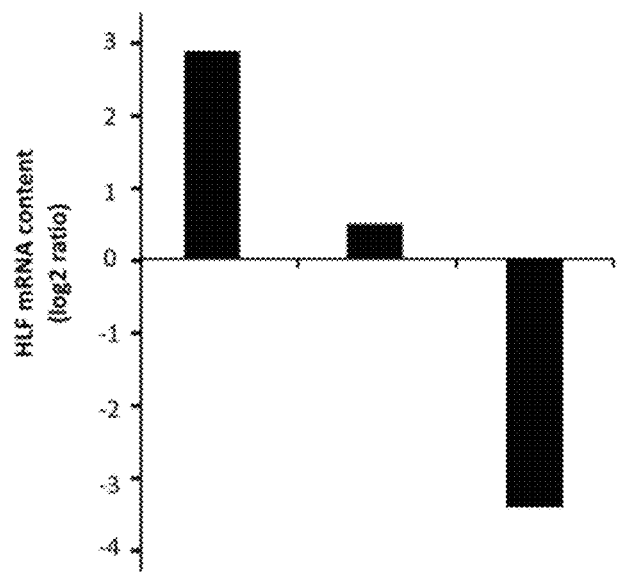
Figure 41B:
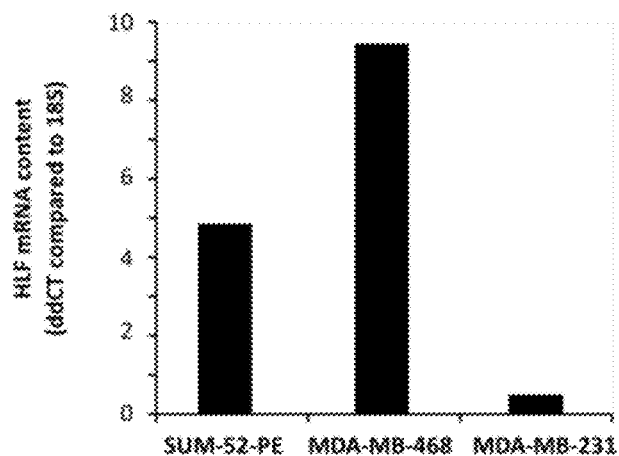
Figure 41C:
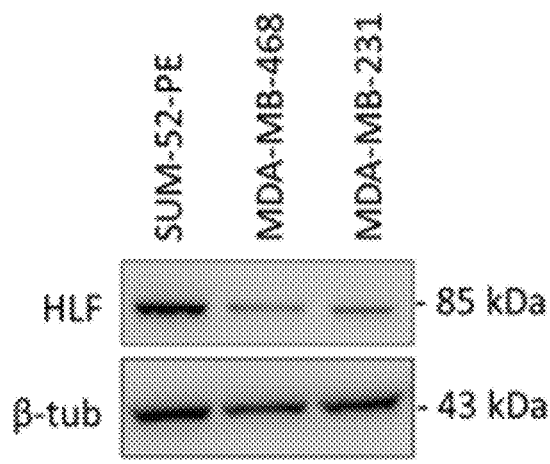

Breast carcinoma cell lines SUM-52-PE, MDA-MB-468 and MDA-MB-231 were chosen for their respective high, moderate, or low, HLF expression levels (FIG. 41A). The HLF mRNA levels were also tested in our laboratory conditions (FIG. 41B) and compared to the ones obtained in literature, and immunoblot of HLF protein expression levels was performed in parallel (FIG. 41C).

According to literature-based and our conditions-based findings of HLF expression levels, we decided to consider both SUM-52-PE and MDA-MB-468 as cell lines with high HLF expression level for downregulation experiments.

Figure 42A:
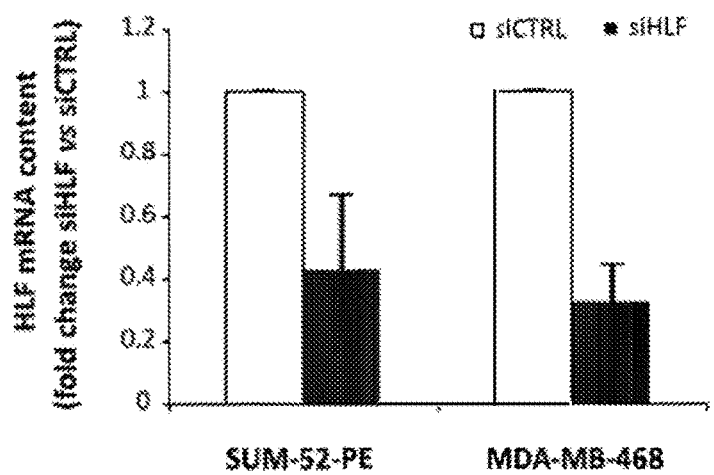

For the initial experiments, the HLF gene expression in TNBC cell lines was inhibited by specific siRNA (ON-TARGETplus HLF siRNA, Dharmacon), using Lipofectamine RNAiMAX transfection agent (FIG. 42A). The CTRL siRNA (ON-TARGETplus Non-targeting siRNA, Dharmacon) was used as a negative control of transfection and further experiments were performed by comparing the HLF-knocked-down effect in siHLF cells vs siCTRL cells.

Figure 42B:
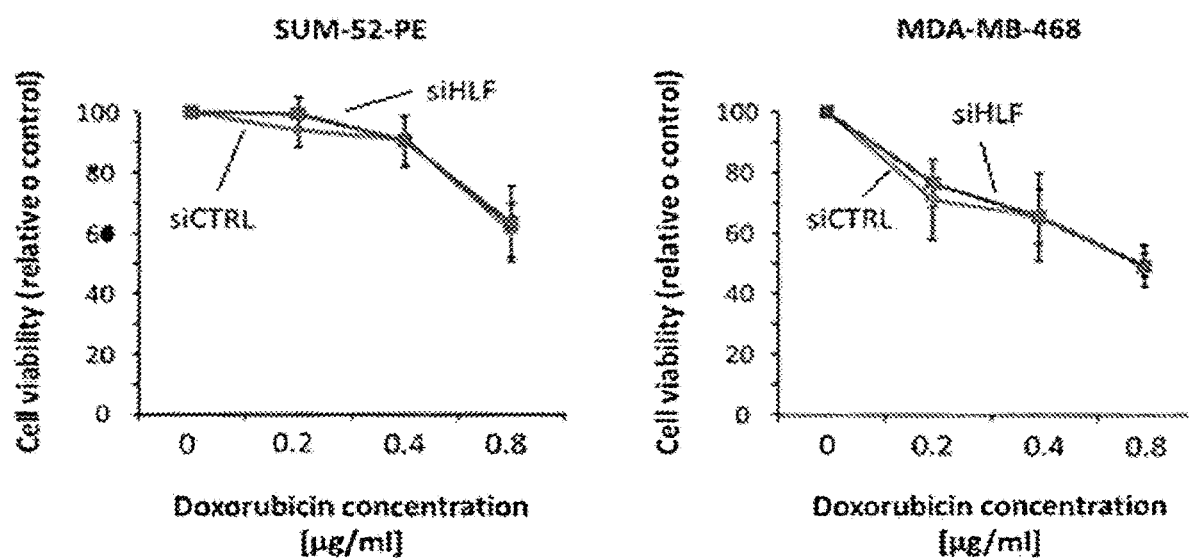

The previous genomic data of our group declared that HLF expression level was reduced in patients' samples with high post-ChT TILs presence. This supports the hypothesis of the low HLF expression levels being connected to ChT-sensitivity of cancer cells, so the first step of our experiments was to verify the possible effect of HLF knock-down on cellular viability under ChT treatment, 24 hours after transient transfection with siHLF and siCTRL. We performed a set of experiments using doxorubicin as a ChT treatment during 48 hours in various concentrations, and cell viability was determined using CellTiter Glow Luminescent Cell Viability Assay (Promega) according to the manufacturer's recommendations. As shown in FIG. 42B, no significant difference in cell viability was detected between siHLF cells, when compared to siCTRL counterparts, in any of tested doxorubicin concentrations. Two other time points (24 h, 72 h) were applied and did not show any further effect (data not shown). Furthermore, the HLF expression level decrease, performed by transient transfection on both cell lines, did not significantly affect cellular viability or morphology (data not shown).

This initial set of siRNA experiments of HLF downregulation has shown unclear results, so for the next experiments of HLF activity in ChT treated cells and to analyze various gene expression levels due to HLF downregulation, we decided to perform the HLF knock-down using CRISPR/Cas9 (Clustered Regularly Interspaced Palindromic Repeats Associated Protein 9) system. The CRISPR/Cas9 is a system of targeted genome editing that works with a principle of short guide RNA sequence that recognizes the target DNA with very limited off-target effect (Barrangou et al., 2015). Subsequently, the endonuclease Cas9 is responsible for target DNA cleavage (DNA flanked by a protospacer-adjacent motif), and the DNA repair of both cleaved parts follows by the machineries of non-homologous end joining or homology-directed repair (Hsu et al., 2014).

Cell lines SUM-52-PE and MDA-MB-468 were transfected by LIPOFECTAMINE® 2000 using plasmid pX278 with HLF-recognizing sequence developed by our collaborators from IGBMC, Strasbourg (FIG. 43; SEQ ID NOs: 5 and 6). The plasmid bears a sequence specific for human HLF gene, and another plasmid was developed for mouse Hlf editing, which is planned to use on murine models, containing the sequences represented by the nucleotide sequences SEQ ID NO: 5, and SEQ ID NO: 6 and their complements, as shown in FIG. 43.

Transfection effectivity of plasmid pX278 carrying the GFP-tag was verified by IF and transfected cells selection in puromycin-containing culture medium was performed for 48 hours, in order to select only clones bearing a knock-down of HLF together with puromycin resistance cassette. Further subcloning of resistant clones was done and the HLF expression levels were tested in each of potentially HLF-knocked-down clones. Three clones for each of SUM-52-PE and MDA-MB-468 cell line were established and can serve as a model for studies of HLF knock-down in stable manner. The analyses of HLF knock-down effect on cells treated with doxorubicin are ongoing, and the preliminary data show the decreasing tendency in cancer cell viability as a direct effect of HLF knock-down. This trend is not yet clear and needs a further confirmation, although it is in line with literature-based information.

Additionally, the microarray-based gene expression analysis of genes affected by HLF expression level decrease is programmed in parallel in those cells carrying the HLF knock-down. Microarray gene expression analysis in HLF transduced cell models suggested the upregulation of cytochrome P450 enzymes, often associated with circadian rhythms and drug metabolism, as well as the upregulation of genes influencing chemical toxicity (Waters et al., 2013). Gene expression analysis in our laboratory aims to compare the genomic profiles of TNBC cells with HLF knock-down vs control cells, and will inform us about the impact of HLF on breast carcinoma cells. The possible implication of HLF downregulation in apoptotic pathways, in drug metabolism, or in genes implicated in lymphocytic attraction will be studied intensively.

Breast mouse cell lines transfections by CRISPR/Cas9 method based plasmid to knock-out mouse HLF are ongoing in our laboratory. In this future project direction, mouse models are intended to be established, in order to be able to study the direct impact of HLF knock-out in the tumor development in vivo and to monitor the lymphocytic infiltration of these tumors. Since the carcinomas of TNBC subtype cannot be treated using ET-based agents or by anti-HER2 targeted therapy, the majority of these tumors are treated by ChT. The presence of TILs in tumor after neoadjuvant ChT is associated with good prognosis and therefore it is of major interest to find out the mechanisms of this lymphocytic infiltration. Potential therapeutic targets, involved in this mechanism, could serve for new therapies development and could improve the prognosis, when combined with standard ChT, applied on TNBC patients. Additionally, the role of potential predictive biomarkers of response to neoadjuvant ChT, such possibly HLF, could be very important, in order to avoid the over-dose of chemotherapeutic agents in potentially non-responding patients, or contrarily, to select those patients with high benefit of ChT in neoadjuvant settings.

| SEQUENCE LISTING |
|---|

SEQ ID NO: 1
*Homo sapiens* guanylate binding protein 1 (GBP1), DNA
NCBI Reference Sequence: NM_002053.2

```
   1    ggagtcagtg atttgaacga agtactttca gtttcatatt actctaaatc cattacaaat
  61    ctgcttagct tctaaatatt tcatcaatga ggaaatccca gccctacaac ttcggaacag
 121    tgaaatatta gtccagggat ccagtgagag acacagaagt gctagaagcc agtgctcgtg
 181    aactaaggag aaaaagaaca gacaagggaa cagcctggac atggcatcag agatccacat
 241    gacaggccca atgtgcctca ttgagaacac taatgggcga ctgatggcga tccagaagc
 301    tctgaagatc ctttctgcca ttacacagcc tatggtggtg gtggcaattg tgggcctcta
 361    ccgcacaggc aaatcctacc tgatgaacaa gctggctgga agaaaaaagg gcttctctct
 421    gggctccacg gtgcagtctc acactaaagg aatctggatg tggtgtgtgc cccaccccaa
 481    gaagccaggc cacatcctag ttctgctgga caccgagggt ctgggagatg tagagaaggg
 541    tgacaaccag aatgactcct ggatcttcgc cctggccgtc ctcctgagca gcaccttcgt
 601    gtacaatagc ataggaacca tcaaccagca ggctatggac caactgtact atgtgacaga
 661    gctgacacat agaatccgat caaaatcctc acctgatgag aatgagaatg aggttgagga
 721    ttcagctgac tttgtgagct tcttcccaga ctttgtgtgg acactgagag atttctccct
 781    ggacttggaa gcagatggac accccctcac accagatgag tacctgacat actcccctga
 841    gctgaagaaa ggtaccagtc aaaaagatga aacttttaac ctgcccagac tctgtatccg
 901    gaaattcttc ccaaagaaaa aatgctttgt ctttgatcgg cccgttcacc gcaggaagct
 961    tgcccagctc gagaaactac aagatgaaga gctggacccc gaatttgtgc aacaagtagc
1021    agacttctgt tcctacatct ttagtaattc caaaactaaa actcttcag gaggcatcca
1081    ggtcaacggg cctcgtctag agagcctggt gctgacctac gtcaatgcca tcagcagtgg
1141    ggatctgccg tgcatggaga acgcagtcct ggccttggcc cagatagaga actcagctgc
1201    agtgcaaaag gctattgccc actatgaaca gcagatgggc cagaaggtgc agctgcccac
1261    agaaaccctc caggagctgc tggacctgca cagggacagt gagagagagg ccattgaagt
1321    cttcatcagg agttccttca aagatgtgga ccatctattt caaaggagt tagcggccca
1381    gctagaaaaa aagcgggatg acttttgtaa acagaatcag gaagcatcat cagatcgttg
1441    ctcagcttta cttcaggtca ttttcagtcc tctagaagaa gaagtgaagg cgggaattta
1501    ttcgaaacca gggggctatc gtctctttgt tcagaagcta aagacctga agaaaaagta
1561    ctatgaggaa ccgaggaagg ggatacaggc tgaagagatt ctgcagacat acttgaaatc
1621    caaggagtct atgactgatg caattctcca gacagaccag actctcacag aaaaagaaaa
1681    ggagattgaa gtggaacgtg tgaaagctga gtctgcacag gcttcagcaa aaatgttgca
1741    ggaaatgcaa agaaagaatg agcagatgat ggaacagaag gagaggagtt atcaggaaca
1801    cttgaaacaa ctgactgaga agatggagaa cgacagggtc cagttgctga agagcaaga
1861    gaggaccctc gctcttaaac ttcaggaaca ggagcaacta ctaaaagagg gatttcaaaa
1921    agaaagcaga ataatgaaaa atgagataca ggatctccag acgaaaatga gacgacgaaa
1981    ggcatgtacc ataagctaaa gaccagagcc ttcctgtcac ccctaaccaa ggcataattg
2041    aaacaatttt gaatttggga acaagcgtca ctacatttga taataattag atcttgcatc
2101    ataacaccaa aagtttataa aggcatgtgg tacaatgatc aaaatcatgt ttttcttaa
2161    aaaaaaaaaa agactgtaaa ttgtgcaaca aagatgcatt tacctctgta tcaactcagg
2221    aaatctcata agctggtacc actcaggaga agtttattct tccagatgac cagcagtaga
```

| | |
|---|---|
| 2281 | caaatggata ctgagcagag tcttaggtaa aagtcttggg aaatatttgg gcattggtct |
| 2341 | ggccaagtct acaatgtccc aatatcaagg acaaccaccc tagcttctta gtgaagacaa |
| 2401 | tgtacagtta tccgttagat caagactaca cggtctatga gcaataatgt gatttctgga |
| 2461 | cattgcccat gtataatcct cactgatgat ttcaagctaa agcaaaccac cttatacaga |
| 2521 | gatctagaat ctctttatgt tctccagagg aaggtggaag aaaccatggg caggagtagg |
| 2581 | aattgagtga taaacaattg ggctaatgaa gaaaacttct cttattgttc agttcatcca |
| 2641 | gattataact tcaatgggac actttagacc attagacaat tgacactgga ttaaacaaat |
| 2701 | tcacataatg ccaaatacac aatgtattta tagcaacgta taatttgcaa agatggactt |
| 2761 | taaaagatgc tgtgtaacta aactgaaata attcaattac ttattattta gaatgttaaa |
| 2821 | gcttatgata gtcttttcta actcttaaca ctcatacttg aaaactttct gagtttcccc |
| 2881 | agaagagaat atgggatttt ttttgacatt tttgactcat ttaataatgc tcttgtgttt |
| 2941 | acctagtata tgtagacttt gtcttatgtg tgaaaagtcc taggaaagtg gttgatgttt |
| 3001 | cttatagcaa ttaaaaatta tttttgaact gaaaatacaa tgtatttcac |

SEQ ID NO: 2
*Homo sapiens* HLF, PAR bZIP transcription factor (HLF), DNA
NCBI Reference Sequence: NM_002126.4

| | |
|---|---|
| 1 | actcttgtca gggccgcggc acatgggcgg ccggatgcgc tgagcccggc gctgcgggc |
| 61 | cgcggagcgc tggggagcag cggccgccgg cgcggggagg ggggtggggt gggacggcgc |
| 121 | accgcctccg gtgctggcac taggggctgg ggtcggcgcg gtgtcttctg cccttctgca |
| 181 | gccgtcgaca tttttttttc tttctttttt tcaattttga acattttgca aaacgagggg |
| 241 | ttcgaggcag gtgagagcat cctgcacgtc gccggggagc ccgcgggcac ttggcgcgct |
| 301 | ctcctgggac cgtctgcact ggaaacccga aagtttttt ttaatatata tttttatgca |
| 361 | gatgtattta taaagatata agtaattttt ttcttccctt ttctccaccg ccttgagagc |
| 421 | gagtacttt ggcaaaggac ggaggaaaag ctcagcaaca ttttaggggg cggttgtttc |
| 481 | tttcttattt ctttttttaa ggggaaaaaa tttgagtgca tcgcgatgga gaaaatgtcc |
| 541 | cgaccgctcc ccctgaatcc caccttatc ccgcctccct acggcgtgct caggtccctg |
| 601 | ctggagaacc cgctgaagct ccccccttcac cacgaagacg catttagtaa agataaagac |
| 661 | aaggaaaaga agctggatga tgagagtaac agcccgacgg tccccccagtc ggcattcctg |
| 721 | gggcctacct tatgggacaa aacccttccc tatgacggag atactttcca gttggaatac |
| 781 | atggacctgg aggagttttt gtcagaaaat ggcattcccc ccagcccatc tcagcatgac |
| 841 | cacagccctc accctcctgg gctgcagcca gcttcctcgg ctgcccctc ggtcatggac |
| 901 | ctcagcagcc gggcctctgc acccctcac cctggcatcc catctccgaa ctgtatgcag |
| 961 | agccccatca gaccaggtca gctgttgcca gcaaaccgca atacaccaag tcccattgat |
| 1021 | cctgacacca tccaggtccc agtgggttat gagccagacc cagcagatct tgccctttcc |
| 1081 | agcatccctg gccaggaaat gtttgaccct cgcaaacgca agttctctga ggaagaactg |
| 1141 | aagccacagc ccatgatcaa gaaagctcgc aaagtcttca tccctgatga cctgaaggat |
| 1201 | gacaagtact gggcaaggcg cagaaagaac aacatggcag ccaagcgctc ccgcgacgcc |
| 1261 | cggaggctga aagagaacca gatcgccatc cgggcctcgt tcctggagaa ggagaactcg |
| 1321 | gccctccgcc aggaggtggc tgacttgagg aaggagctgg gcaaatgcaa gaacatactt |
| 1381 | gccaagtatg aggccaggca cgggcccctg taggatggca tttttgcagg ctggctttgg |

-continued

| | SEQUENCE LISTING |
|---|---|
| 1441 | aatagatgga cagtttgttt cctgtctgat agcaccacac gcaaaccaac ctttctgaca |
| 1501 | tcagcacttt accagaggca taaacacaac tgactcccat tttggtgtgc atctgtgtgt |
| 1561 | gtgtgcgtgt atatgtgctt gtgctcatgt gtgtggtcag cggtatgtgc gtgtgcgtgt |
| 1621 | tcctttgctc ttgccatttt aaggtagccc tctcatcgtc ttttagttcc aacaaagaaa |
| 1681 | ggtgccatgt ctttactaga ctgaggagcc ctctcgcggg tctcccatcc cctccctcct |
| 1741 | tcactcctgc ctcctcagct ttgcttcatg ttcgagctta cctactcttc caggactctc |
| 1801 | tgcttggatt cactaaaaag ggccctggta aaatagtgga tctcagtttt taagagtaca |
| 1861 | agctcttgtt tctgtttagt ccgtaagtta ccatgctaat gaggtgcaca caataactta |
| 1921 | gcactactcc gcagctctag tcctttataa gttgctttcc tcttacttcc agttttggtg |
| 1981 | ataatcgtct tcaaattaaa gtgctgttta gatttattag atcccatatt tacttactgc |
| 2041 | tatctactaa gtttcctttt aattctacca accccagata agtaagagta ctattaatag |
| 2101 | aacacagagt gtgttttgc actgtctgta cctaaagcaa taatcctatt gtacgctaga |
| 2161 | gcatgctgcc tgagtattac tagtggacgt aggatatttt ccctacctaa gaatttcact |
| 2221 | gtcttttaaa aaacaaaaag taaagtaatg catttgagca tggccagact attccctagg |
| 2281 | acaaggaagc agagggaaat gggaggtcta aggatgaggg gttaatttat cagtacatga |
| 2341 | gccaaaaact gcgtcttgga ttagcctttg acattgatgt gttcggtttt gttgttcccc |
| 2401 | ttccctcaca ccctgcctcg cccccacttt tctagttaac ttttttccata tccctcttga |
| 2461 | cattcaaaac agttacttaa gattcagttt tcccactttt tggtaatata tatattttg |
| 2521 | tgaattatac tttgttgttt ttaaaaagaa aatcagttga ttaagttaat aagttgatgt |
| 2581 | tttctaaggc cctttttcct agtggtgtca ttttttgaatg cctcataaat taatgattct |
| 2641 | gaagcttatg tttcttattc tctgtttgct tttgaacgta tgtgctctta taaagtggac |
| 2701 | ttctgaaaaa tgaatgtaaa agacactggt gtatctcaga aggggatggt gttgtcacaa |
| 2761 | actgtggtta atccaatcaa tttaaatgtt tactatagac caaaggaga gattattaaa |
| 2821 | tcgtttaatg tttatacaga gtaattatag gaagttcttt tttgtacagt atttttcaga |
| 2881 | tataaatact gacaatgtat tttggaagac atatattata tatagaaaag aggagaggaa |
| 2941 | aactattcca tgttttaaaa ttatatagca aagatatata ttccaatg ttgtacagag |
| 3001 | aagaagtgct tgggggtttt tgaagtcttt aatattttaa gccctatcac tgacacatca |
| 3061 | gcatgttttc tgctttaaat taaaatttta tgacagtatc gaggcttgtg atgacgaatc |
| 3121 | ctgctctaaa atacacaagg agctttcttg tttcttatta ggcctcagaa agaagtcagt |
| 3181 | taacgtcacc caaaagcaca aaatggattt tagtcaaata tttattggat gatacagtgt |
| 3241 | tttttaggaa aagcatctgc cacaaaaatg ttcacttcga aattctgagt tcctggaatg |
| 3301 | gcacgttgct gccagtgccc cagacagttc ttttctaccc tgcgggcccg cacgttttat |
| 3361 | gaggttgata tcggtgctat gtgtttggtt tataatttga tagatgtttg actttaaaga |
| 3421 | tgattgttct tttgtttcat taagttgtaa aatgtcaaga aattctgctg ttacgacaaa |
| 3481 | gaaacatttt acgctagatt aaaatatcct ttcatcaatg ggattttcta gtttcctgcc |
| 3541 | ttcagagtat ctaatccttt aatgatctgg tggtctcctc gtcaatccat cagcaatgct |
| 3601 | tctctcatag tgtcatagac ttgggaaacc caaccagtag gatatttcta caaggtgttc |
| 3661 | attttgtcac aagctgtaga taacagcaag agatggggt gtattggaat tgcaatacat |
| 3721 | tgttcaggtg aataataaaa tcaaaaactt ttgcaatctt aagcagagat aaataaaaga |

```
3781   tagcaatatg agacacaggt ggacgtagag ttggccttttt tacaggcaaa gaggcgaatt
3841   gtagaattgt tagatggcaa tagtcattaa aaacatagaa aaatgatgtc tttaagtgga
3901   gaattgtgga aggattgtaa catggaccat ccaaatttat ggccgtatca aatggtagct
3961   gaaaaaacta tatttgagca ctggtctctc ttggaattag atgtttatat caaatgagca
4021   tctcaaatgt tttctgcaga aaaaaataaa aagattctaa taaaatgtat tctcttgtgt
4081   gccaggagag gtttcagaaa cctacctcgt cttacaaatt taaacactttt ggagtctgta
4141   caggtgcctt atatgtaggt cattgtcacg atacacacac acgaacactc cctctggact
4201   ggctgcctct ccatccaggg cagttaacta gcaaacaagg cagatctgct tcatggagcg
4261   ggaggccatg gcttgactct gagtgatttg ggtcaaccgg agtcagacgc atgtctgcac
4321   gctgcagcta ttatgagagt ccctttgtca tttttcacct tttcatccta agcatctttc
4381   agagattaat tatttggcca ttaacaatga atccaaatca tatcatactg acatcatcta
4441   gacatgattt ggaaggaaca gcttaggacc tcctgatgag gtcacattgt tgtttctttt
4501   aactagactt ggcaaagaaa ggcaaaaatt gaccagccta tcttttctgct ggtgctgcct
4561   taaggaggta gtttgttgag gggagggctg tagatcatta cttctttctc ttcaggaagt
4621   ggccactttg aaccattcaa ataccacatt aggcaagact gtgataggcc ttttgtcttc
4681   aaatacaaca ggcctccact gacccatccc tcaaagcaga aggacccttt gaggagagta
4741   cagatgggat tccacagtgg ggtgggtgga atggaaacct gtactagacc acccagaggt
4801   tccttctaac ccactggttt ggtggggaac tcacagtaat tccaaatgta caatcagatg
4861   tctagggtct gttttcggaa gaagcaagaa ttatcagtgg cacccctcccc actgcccccca
4921   gtgtaaaaca atagacattc tgtgaaatgc aaagctattc tttggttttt ctagtagttt
4981   atctcatttt accctattct tcctttaagg aaaactcaat ctttatcaca gtcaattaga
5041   gcgatcccaa ggcatgggac caggcctgct tgcctatgtg tgatggcaat tggagatctg
5101   gatttagcac tggggtctca gcaccctgca ggtgtctgag actaagtgat ctgccctcca
5161   ggtggcgatc accttctgct cctaggtacc cccactggca aggccaaggt ctcctccacg
5221   ttttttctgc aattaataat gtcatttaaa aaatgagcaa agccttatcc gaatcggata
5281   tagcaactaa agtcaataca ttttgcagga ggctaagtgt aagagtgtgt gtgtgtgtgt
5341   gtgcgtgcat gtgtgtgtgt gtgtatgtgt gtgaataagt cgacataaag tctttaattt
5401   tgagcacctt accaaacata acaataatcc attatccttt tggcaacacc acaaagatcg
5461   catctgttaa acaggtacaa gttgacatga ggttagttta attgtacacc atgatattgg
5521   tggtatttat gctgttaagt ccaaaccttt atctgtctgt tattcttaat gttgaataaa
5581   ctttgaattt tttcctttca aaaaaaa
```

SEQ ID NO: 3
*Homo sapiens* C-X-C motif chemokine ligand 13 (CXCL13), DNA
NCBI Reference Sequence: NM_006419.2

```
  1   gagaagatgt ttgaaaaaac tgactctgct aatgagcctg gactcagagc tcaagtctga
 61   actctacctc cagacagaat gaagttcatc tcgacatctc tgcttctcat gctgctggtc
121   agcagcctct ctccagtcca aggtgttctg gaggtctatt acacaagctt gaggtgtaga
181   tgtgtccaag agagctcagt ctttatccct agacgcttca ttgatcgaat tcaaatcttg
241   ccccgtggga atggttgtcc aagaaaagaa atcatagtct ggaagaagaa caagtcaatt
301   gtgtgtgtgg accctcaagc tgaatggata caaagaatga tggaagtatt gagaaaaaga
```

```
 361   agttcttcaa ctctaccagt tccagtgttt aagagaaaga ttccctgatg ctgatatttc
 421   cactaagaac acctgcattc ttcccttatc cctgctctgg attttagttt tgtgcttagt
 481   taaatctttt ccaggaaaaa gaacttcccc atacaaataa gcatgagact atgtaaaaat
 541   aaccttgcag aagctgatgg ggcaaactca agcttcttca ctcacagcac cctatataca
 601   cttggagttt gcattcttat tcatcaggga ggaaagtttc tttgaaaata gttattcagt
 661   tataagtaat acaggattat tttgattata tacttgttgt ttaatgttta aaatttctta
 721   gaaaacaatg gaatgagaat ttaagcctca aatttgaaca tgtggcttga attaagaaga
 781   aaattatggc atatattaaa agcaggcttc tatgaaagac tcaaaaagct gcctgggagg
 841   cagatggaac ttgagcctgt caagaggcaa aggaatccat gtagtagata tcctctgctt
 901   aaaaactcac tacggaggag aattaagtcc tacttttaaa gaatttcttt ataaaattta
 961   ctgtctaaga ttaatagcat tcgaagatcc ccagacttca tagaatactc agggaaagca
1021   tttaagggt gatgtacaca tgtatccttt cacacatttg ccttgacaaa cttctttcac
1081   tcacatcttt ttcactgact ttttttgtgg ggggcggggc cggggggact ctggtatcta
1141   attctttaat gattcctata aatctaatga cattcaataa agttgagcaa acatttact
1201   taaaaaaaaa aaaaaaaaa
```

SEQ ID NO: 4
Homo sapiens sulfotransferase family 1E member 1 (SULT1E1), DNA
NCBI Reference Sequence: NM_005420.2

```
   1   caaatgcaga agtggttctc atctttttt gcagcttaag atctgccttg gtatttgaag
  61   agatataaac tagatcaatt tctttcacag gatcaactaa acagtgtacc acaatgaatt
 121   ctgaacttga ctattatgaa aagtttgaag aagtccatgg gattctaatg tataaagatt
 181   ttgtcaaata ttgggataat gtggaagcgt tccaggcaag accagatgat cttgtcattg
 241   ccacctaccc taaatctggt acaacctggg ttagtgaaat tgtgtatatg atctataaag
 301   agggtgatgt ggaaaagtgc aaagaagatg taattttaa tcgaataccg ttcctggaat
 361   gcagaaaaga aaacctcatg aatggagtaa acaattaga tgagatgaat ctcctagaa
 421   ttgtgaagac tcatttgcca cctgaacttc ttcctgcctc attttgggaa aaggattgta
 481   agataatcta tctttgccgg aatgcaaagg atgtggctgt ttcctttat tatttctttc
 541   taatggtggc tggtcatcca aatcctggat cctttccaga gtttgtggag aaattcatgc
 601   aaggacaggt tccttatggt tcctggtata acatgtaaa atcttggtgg gaaaagggaa
 661   agagtccacg tgtactattt cttttctacg aagacctgaa agaggatatc agaaaagagg
 721   tgataaaatt gatacatttc tggaaagga agccatcaga ggagcttgtg acaggatta
 781   tacatcatac ttcgttccaa gagatgaaga acaatccatc cacaaattac acaacactgc
 841   cagacgaaat tatgaaccag aaattgtcgc ccttcatgag aaagggaatt acaggagact
 901   ggaaaaatca ctttacagta gccctgaatg aaaaatttga taacattat gagcagcaaa
 961   tgaaggaatc tacactgaag tttcgaactg agatctaaga aggtctttct ttacttaaca
1021   tatctgatat taaagatttc ttttcattat tctccacttt ttcttatttt agattgctag
1081   aaaagacata atcatggatt atgttgacat tttctttta aatttttgtt taacttttt
1141   tttttttttt tgagacagag tctcactctg ttgcctaggc tggaggacag tggcacaatc
1201   atggctgatt gcagcctgga cctccttgac tcaattgatc ctcccatctc agcctcccaa
1261   gtagctagga ctacagacat gtgcaaccat gtttggctaa ttttttttaat gttttttgt
```

SEQUENCE LISTING

```
1321   agagatgagg  tcttattata  ttgtccaggc  tggtcttgaa  ttcctgggct  caagcttccc 1381   aagtagctgc  aacaacaggc  acacaccacc  atgctcaact  aattttattt  ctattttttg 1441   tatagacagg  ggcttgctat  agtgtccagg  ctggtctgaa  acccttgagc  tcaagtgatc 1501   ttcccacacc  agcctcccaa  aatactggga  ttacaggctt  gagcctccat  gcctggccca 1561   ggtaacatgt  ttattgagct  gtacatgcat  atgagaaata  agaaactttt  ttttcctact 1621   atcatctctt  aaattttgtt  ttcttttttct tttgcttcct  cttcttcttt  tctattttttt 1681   ataaatatca  tgcacaacta  taacctatgg  gaatgatgta  gtaacacaga  ttattcatct 1741   tgttagagtt  gtattaaaaa  taaacaagca  tttcaaatta  aaaaaaaaaa  aaaaaaaaaa 1801   aaaaa
```

FIGURES

FIGS. 1a and 1b: Participants' flow chart in the training phase

FIG. 2: Box plots of raw data

FIG. 3: Density plots of raw data

FIG. 4: Box plots after separate frozen normalization

FIG. 5: Density plots after separate frozen normalization

FIG. 6: Box plots after cross-platform normalization

FIG. 7: Density plots after cross-platform normalization

FIG. 8: Histograms of stromal TIL in TOP samples, MDACC samples and overall

Figure 9:
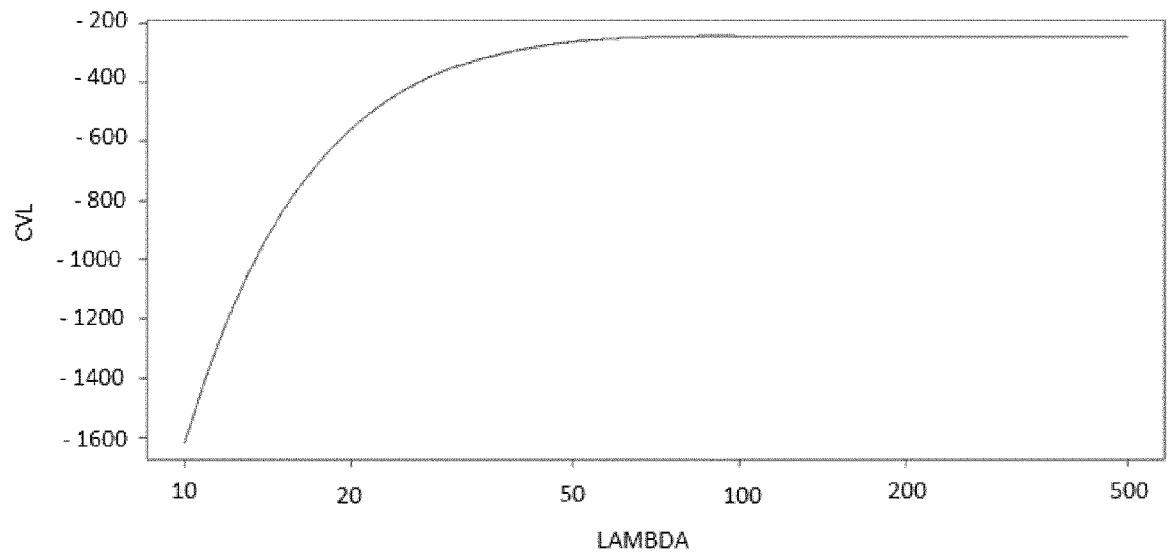

FIG. 9: Cross validated likelihood as a function of the tuning parameter

Figure 10:
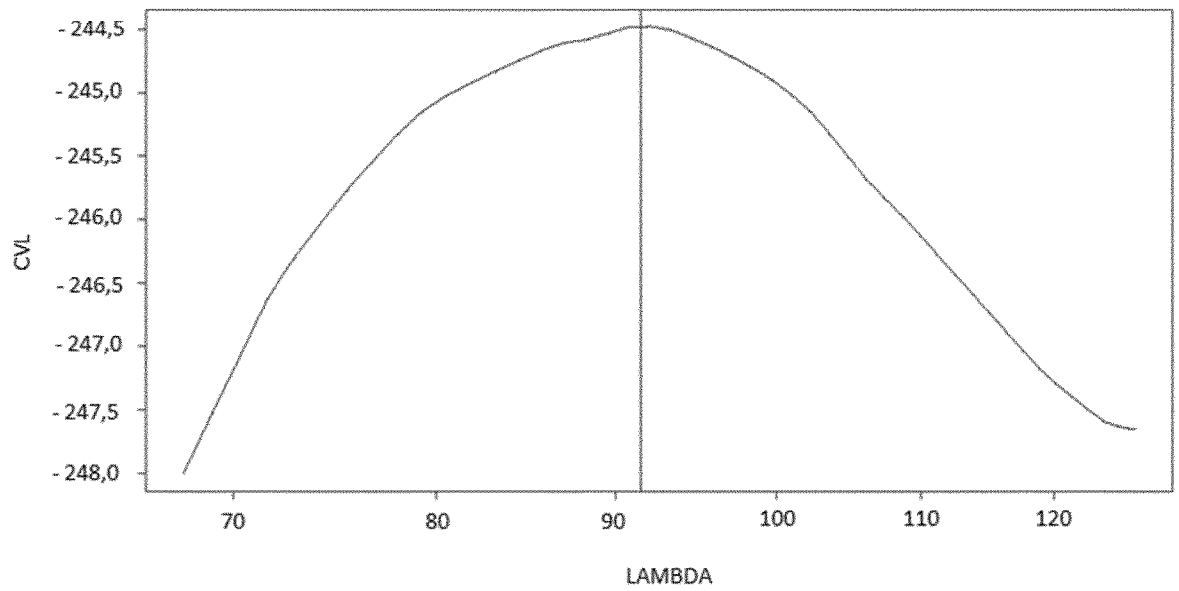
Figure 24:
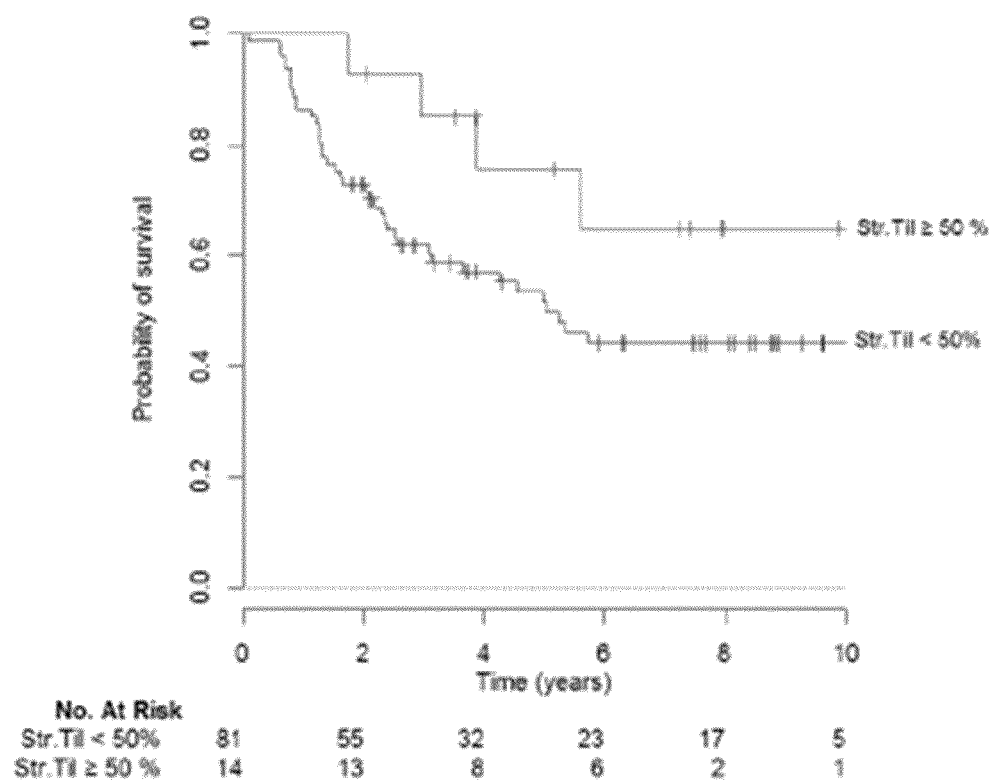

FIG. 10: Cross validated likelihood as a function of the tuning parameter in the neighborhood of the maxima FIG. 11: Histograms of the genomic predictor in TOP samples, MDACC sample and overall FIG. 12: Histograms of the transformed genomic predictor in TOP samples, MDACC sample and overall FIG. 13: Check for non-log-linear effect of the predictor on distant relapse-free survival FIG. 14: Check for non-log-linear effect of the predictor on overall survival FIG. 15: Distant relapse-free survival of different risk groups—TER FIG. 16: Distant relapse-free survival of different risk groups—MED FIG. 17: Distant relapse-free survival of different risk groups—COX FIG. 18: Overall survival of different risk groups—TER FIG. 19: Overall survival of different risk groups—MED FIG. 20: Overall survival of different risk groups—COX FIG. 21: Spearman pairwise correlation of genes—Training FIG. 22: Profiles of stromal TIL—Grey lines: individual profiles—Green line: mean profile FIG. 23: Check for non-log-linear effect of stromal TIL on distant relapse-free survival FIG. 24: Kaplan-Meier distant-relapse free survival curves according to stromal TIL cut-off (50%)

FIG. 25: Check for non-log-linear effect of stromal TIL on overall survival

Figure 26:
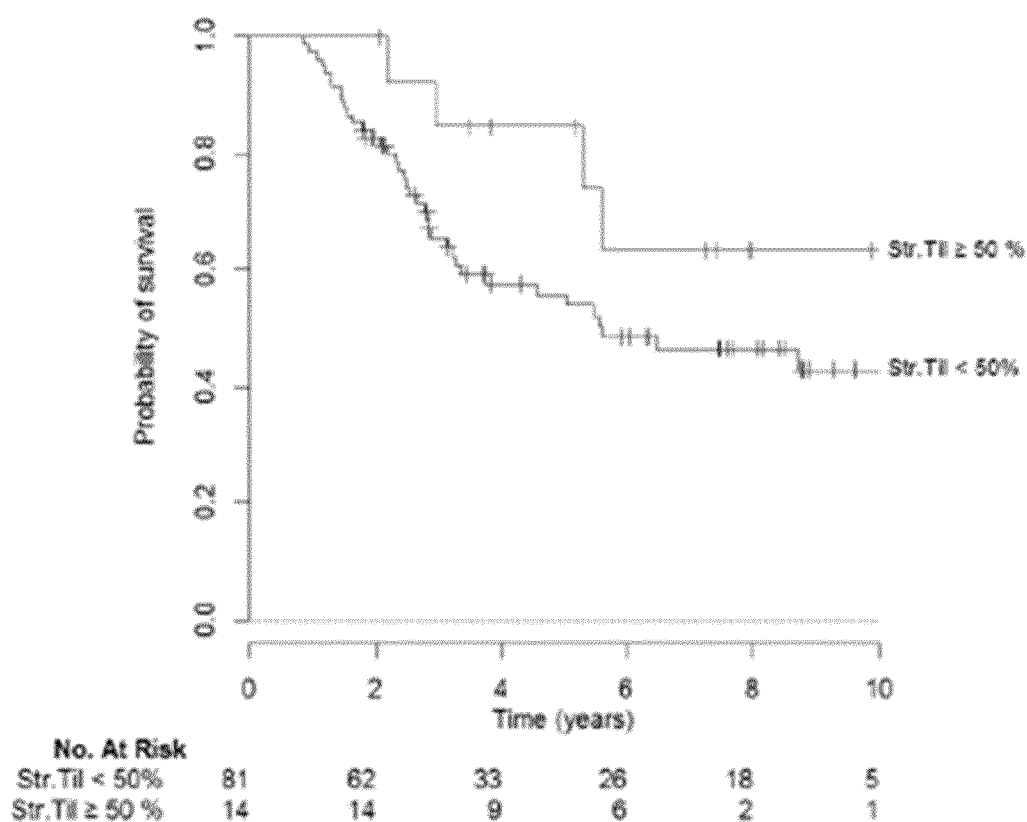

FIG. 26: Kaplan-Meier overall survival curves according to stromal TIL cut-off (50%)

FIG. 27: Participants' flow chart of the validation dataset

FIG. 28: Histograms of the genomic predictor in the validation dataset

FIG. 29: Histograms of the transformed genomic predictor in the validation dataset FIG. 30: Check for non-log-linear effect of the genomic predictor on distant relapse-free survival—Validation dataset—Patients achieving pCR FIG. 31: Check for non-log-linear effect of the genomic predictor on distant relapse-free survival—Validation dataset FIG. 32: Distant relapse-free survival of different risk groups—No pCR—TER FIG. 33: Distant relapse-free survival of different risk groups—No pCR—MED FIG. 34: Distant relapse-free survival of different risk groups—No pCR—COX FIG. 35: Distant relapse-free survival of different risk groups—All patients—TER FIG. 36: Distant relapse-free survival of different risk groups—All patients—MED FIG. 37: Distant relapse-free survival of different risk groups—All patients—COX FIG. 38: Spearman pairwise correlation of genes—Validation FIG. 39: Histograms of the genomic predictor—Training vs. validation FIG. 40: Histograms of the transformed genomic predictor—Training vs. validation FIG. 41: Comparison of HLF expression levels in three breast carcinoma cell lines Literature microarray-based log 2 ratio of HLF mRNA levels, compared to "universal reference RNA" that represents a mixture of RNAs of 11 well described BC cell lines, on SUM-52-PE, MDA-MB-468 and MD-MB-231 cell lines (A) (Kao et al., 2009). HLF mRNA content showed as a ddCT with 18S expression levels as an internal control in our laboratory conditions (B). Western blot of HLF protein expression on three cell lines. Beta-tubulin was used as loading control. Used antibodies: rabbit monoclonal anti-HLF (Genetex), mouse monoclonal anti-β-tubulin (Sigma Aldrich). (C)

FIG. 42: Cell lines SUM-52-PE and MDA-MB-468 with HLF siRNA knock-down Cell lines SUM-52-PE and MDA-MB-468 were transfected with siRNA specific for HLF (or non-targeting control). The HLF mRNA expression level was tested for each experiment and was summarized in one graph. The amount of 18S mRNA was used as internal reference for normalizing qPCR. (A). Cell viability was tested between siHLF and siCTRL cells when treated with doxorubicin (B).

FIG. 43: Plasmid for CRISPR/Cas9 human HLF targeted genome editing (comprising the sequences SEQ ID NOs: 5 and 6)

The structure of plasmid pX278 (carrying the GFP-tag) for CRISPR/Cas9 human HLF targeted genome editing designed by Bernardo Reina San Martin, IGBMC, Strasbourg.

FIG. 44: Effect of changing the tuning parameter on the values of fitted regression coefficients FIG. 45: Fitted stromal TILs (Box-cox-transformed) vs. observed stromal TILs (Box-cox-transformed)

The invention claimed is:

1. A method of treating a patient with triple negative breast cancer (TNBC) comprising:
   measuring mRNA quantity resulting from expression from genes GBP1, HLF, CXCL13 and SULT1E1 in a sample taken from a biopsy from a tumor of the patient before neoadjuvant chemotherapy;
   determining a genomic predictor score of more than or equal to 0.51 based on the measured mRNA quantity according to formula:

Genomic predictor score=0.288*GBP1 expression+ 0.392*CXCL13 expression−1.027*HLF expression−1.726*SULT1E1 expression; and treating the patient with a neoadjuvant chemotherapy (NACT).

2. The method according to claim 1, wherein the method allowing measurement of mRNA quantity is selected from the group consisting of micro array, PCR, RT-PCR, and Affymetrix gene array.

3. The method according to claim 1, wherein the four genes corresponding to GBP1 gene, HLF gene, CXCL13 gene and SULT1E1 gene are respectively represented by the nucleotide sequences SEQ ID NO: 1, SEQ ID NO: 2, SEQ ID NO: 3, and SEQ ID NO: 4.

* * * * *